United States Patent
Nicholson et al.

(10) Patent No.: US 12,065,650 B2
(45) Date of Patent: Aug. 20, 2024

(54) HETEROLOGOUS BIOSYNTHESIS OF NODULISPORIC ACID

(71) Applicant: VICTORIA LINK LIMITED, Wellington (NZ)

(72) Inventors: Matthew Joseph Nicholson, Canterbury (NZ); Sarah Adeline Kessans, Christchurch (NZ); Emily Jane Parker, Wellington (NZ); Leyla Yolanda Bustamante Rodriguez, Prebbleton (NZ); David Barry Scott, Palmerston North (NZ); Kyle Cornelius Van de Bittner, Wellington (NZ); Craig John Van Dolleweerd, Prebbleton (NZ)

(73) Assignee: Massey University, Palmerston (NZ)

( * ) Notice: Subject to any disclaimer, the term of this patent is extended or adjusted under 35 U.S.C. 154(b) by 0 days.

(21) Appl. No.: 17/816,630

(22) Filed: Aug. 1, 2022

(65) Prior Publication Data

US 2023/0365976 A1     Nov. 16, 2023

Related U.S. Application Data

(62) Division of application No. 16/651,065, filed as application No. PCT/IB2018/057528 on Sep. 28, 2018, now Pat. No. 11,453,882.

(30) Foreign Application Priority Data

Sep. 29, 2017 (AU) ................................ 2017903956

(51) Int. Cl.
| | |
|---|---|
| *C12N 15/52* | (2006.01) |
| *A01N 63/30* | (2020.01) |
| *A01N 63/50* | (2020.01) |
| *C12N 15/80* | (2006.01) |
| *C12P 17/18* | (2006.01) |

(52) U.S. Cl.
CPC ............. *C12N 15/52* (2013.01); *A01N 63/30* (2020.01); *A01N 63/50* (2020.01); *C12N 15/80* (2013.01); *C12P 17/18* (2013.01)

(58) Field of Classification Search
CPC ...... C12N 15/52; C12N 15/80; C12N 9/0071; C12N 9/1085; A01N 63/30; A01N 63/50; C12P 17/18; C12P 17/182; C12P 17/188; C12Y 114/00; C12Y 205/01
See application file for complete search history.

(56) References Cited

U.S. PATENT DOCUMENTS

2007/0218461 A1    9/2007   Bryan et al.

OTHER PUBLICATIONS

International Search Report and Written Opinion corresponding to International Patent Application No. PCT/IB2018/057528 mailed Dec. 13, 2018.
Nicholson M.J et al. "Molecular Cloning and Functional Analysis of Gene Clusters for the Biosynthesis ofindole-Diterpenes in Penicillium crustosum and P. janthinellum", Toxins, 2015, vol. 7, pp. 2701-2722, DOI: 1O.33990/toxins7082701 Abstract, Results, Discussion.
Bills, G.F. et al "*Hypoxylon pulicicidum* sp. nov. (Ascomycota, Xylariales), a Pantropical Insecticide-Producing Endophyte" PLoS One. 2012; 7(10): e46687, DOI: 10. 1371/journal.pone.0046687 Abstract, Figure 1, Table 1, p. 16, "Morphology and Culture Studies" and "Fermentation for Detection ofNodulisporic Acids".
Protein Sequence, Hypoxylon pulicicidum strain MF5954 hypothetical protein, cytochrome P450 oxygenase (nodW). Genbank MG 182145.1 (Accession No. MGI82145), Published: I (A) Simplest MIDAS format (B) Extended MIDAS format (C) Fully-enabled MIDAS format

HETEROLOGOUS BIOSYNTHESIS OF NODULISPORIC ACID

RELATED APPLICATIONS

The present patent application is a divisional of U.S. patent application Ser. No. 16/651,065 filed Mar. 26, 2020, which is a 35 U.S.C. 371 U.S. National Phase application of International Patent Application No. PCT/IB2018/057528, which was filed Sep. 28, 2018, claiming the benefit of priority to Australian Patent Application No. 2017903956 filed on Sep. 29, 2017. The entire text of the aforementioned applications is incorporated herein by reference in its entirety.

REFERENCE TO AN ELECTRONIC SEQUENCE LISTING

The contents of the electronic sequence listing (sequence-listing.xml; Size: 118,571 bytes; and Date of Creation: Aug. 1, 2022) is herein incorporated by reference in its entirety.

FIELD OF THE INVENTION

This invention generally relates to novel polypeptides that catalyze at least one biochemical reaction leading to the production of a nodulisporic acid (NA), polynucleotides encoding such polypeptides, methods of making such polypeptides and polynucleotides, and methods of using such polypeptides and polynucleotides to produce at least one NA by heterologous expression in a permissive host.

BACKGROUND

Filamentous fungi produce a diverse repertoire of interesting and useful chemical compounds. Members of one such class of compounds, the indole diterpenes (IDTs), are of particular interest due to their wide range of chemical diversity and concomitant bioactivities, which include anti-MRSA, (Ogata, M.; Ueda, J.; Hoshi, M.; Hashimoto, J.; Nakashima, T.; Anzai, K.; Takagi, M.; Shin-ya, K. *J. Antibiot. (Tokyo)* 2007, 60 (10), 645-648), anti-cancer (anti-H1N1, insecticidal and tremorgenic[6] activities. NAs (FIG. 1) are a group of notably bioactive quasi-paspaline-like IDTs produced by *Hypoxylon pulicicidum*, formerly classified as *Nodulisporium* sp. Nodulisporic acid A (NAA) 10 is of particular significance because it exhibits highly potent insecticidal activity against blood-feeding arthropods while exhibiting no observable adverse effects on mammals.

NAs are especially difficult to biosynthesize from the natural producer, *H. pulicicidum*. Reported NA biosynthesis methods require that *H. pulicicidum* be grown for 21 days in complete darkness in highly nutrient rich media. Due to the difficulty of NAA 10 biosynthesis in *H. pulicicidum*, obtaining useful quantities of NAA 10 using published fermentations methods is challenging, and production of commercial quantities of NAA 10 essentially unachievable. Accordingly, attempts have been made to chemically synthesize NAA 10 resulting in mechanisms for the synthesis of nodulisporic acid F (NAF) 5a and nodulisporic acid D 7a, but full synthesis of NAA 10 has not been achieved.[12] Consequently there is a need in the art for new methods of NAA 10 synthesis and/or biosynthesis that will provide useful quantities of NAA 10.

It is an object of the present invention to provide a polynucleotide encoding at least one enzyme in the NAA 10 biosynthesis pathway of *H. pulicicidum* and/or to provide a method of using such a vector to produce at least one indole diterpene compound that is a NA and/or to produce a precursor to NAA 10 in a heterologous host and/or to at least provide the public with a useful choice.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE INVENTION

In one aspect the invention relates to an isolated polypeptide comprising an amino acid sequence selected from the group consisting of NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or a functional variant or fragment thereof.

In another aspect the invention relates to an isolated polynucleotide encoding a polypeptide comprising an amino acid sequence selected from the group consisting of NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or a functional variant or fragment thereof.

In another aspect the invention relates to an isolated polynucleotide comprising at least 70% nucleic acid sequence identity to a nucleic acid sequence selected from the group consisting of nodW cDNA (SEQ ID NO:2), nodW genomic DNA (SEQ ID NO:1), nodR cDNA (SEQ ID NO:5), nodR genomic DNA (SEQ ID NO:4), nodX cDNA (SEQ ID NO:8), nodX genomic DNA (SEQ ID NO:7), nodM cDNA (SEQ ID NO:11), nodM genomic DNA (SEQ ID NO:10), nodB cDNA (SEQ ID NO:14), nodB genomic DNA (SEQ ID NO:13), nodO cDNA (SEQ ID NO:17), nodO genomic DNA (SEQ ID NO:16), nodJ cDNA (SEQ ID NO:20), nodJ genomic DNA (SEQ ID NO:19), nodC cDNA (SEQ ID NO:23), nodC genomic DNA (SEQ ID NO:22), nodY1 cDNA (SEQ ID NO:26), nodY1 genomic DNA (SEQ ID NO:25), nodD2 cDNA (SEQ ID NO:29), nodD2 genomic DNA (SEQ ID NO:28), nodD1 cDNA (SEQ ID NO:32), nodD1 genomic DNA (SEQ ID NO:31), nodY2 cDNA (SEQ ID NO:35), nodY2 genomic DNA (SEQ ID NO:34), nodZ cDNA (SEQ ID NO:38), nodZ genomic DNA (SEQ ID NO:37), nodS cDNA (SEQ ID NO:49), nods genomic DNA (SEQ ID NO:48), nodI cDNA (SEQ ID NO:55), and nodI genomic DNA (SEQ ID NO:54).

In another aspect the invention relates to a transcription unit (TU) comprising at least one isolated polynucleotide according to the invention.

In another aspect the invention relates to a vector that encodes an isolated polypeptide according to the invention.

In another aspect the invention relates to a vector comprising an isolated nucleic acid sequence or a TU according to the invention.

In another aspect the invention relates to an isolated host cell comprising an isolated polypeptide, isolated polynucleotide, TU and/or vector according to the invention.

In another aspect the invention relates to a method of making at least one NA comprising heterologously expressing at least one polypeptide, isolated nucleic acid sequence, TU or vector according to the invention in an isolated host cell.

In another aspect the invention relates to at least one NA made by a method of the invention.

In another aspect the present invention relates to an isolated polypeptide or functional fragment or variant thereof from *Hypoxylon* spp. that catalyzes a biochemical reaction in the biosynthetic pathway leading from 3-geranylgeranyl indole (GGI) 2 to NAA 10.

In another aspect the present invention relates to an isolated polynucleotide encoding at least one polypeptide or functional variant or fragment thereof from *Hypoxylon* spp. that catalyzes a biochemical reaction in the biosynthetic pathway leading from GGI 2 to NAA 10.

In another aspect the invention relates to a method of making at least one *Hypoxylon* spp. polypeptide or functional variant or fragment thereof comprising heterologously expressing an isolated nucleic acid sequence or vector according to the invention in an isolated host cell.

In another aspect the invention relates to a method of making at least one NA comprising heterologously expressing in an isolated host cell, at least one polypeptide that catalyzes a biochemical reaction in the biosynthetic pathway leading from GGI 2 to NAA 10.

In another aspect the invention relates to an isolated host cell that expresses at least one heterologous polypeptide that catalyzes the transformation of a substrate in the biosynthetic pathway leading from GGI 2 to the formation of NAA 10.

In another aspect the invention relates to an isolated host cell that produces by heterologous expression, at least one polypeptide involved in the biosynthetic pathway leading from GGI 2 to NAA 10.

In another aspect the invention relates to a method of producing at least one NA comprising contacting a carbohydrate comprising substrate with a recombinant cell transformed with a nucleic acid that results in an increased level of activity of a polypeptide selected from the group consisting of NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or a functional variant or fragment thereof compared to the cell prior to transformation, such that the substrate is metabolized to at least one NA.

In another aspect the invention relates to an isolated strain of *Hypoxylon pulicicidum* that comprises at least one heterologous nucleic acid sequence encoding an enzyme in a biosynthetic pathway leading to NAA 10.

In another aspect the invention relates to an isolated strain of *Hypoxylon pulicicidum* that expresses at least two different GGPPS enzymes.

In another aspect the invention relates to an isolated strain of *Hypoxylon pulicicidum* that comprises a genetic modification that leads to an increased biosynthesis of NAA 10.

In another aspect the invention relates to a method of making NAA 10 comprising expressing at least one heterologous nucleic acid sequence in *Hypoxylon pulicicidum*, wherein the at least one heterologous nucleic acid sequence encodes an enzyme in a biosynthetic pathway leading to NAA 10.

Various embodiments of the different aspects of the invention as discussed above are also set out below in the detailed description of the invention, but the invention is not limited thereto.

Other aspects of the invention may become apparent from the following description which is given by way of example only and with reference to the accompanying drawings.

BRIEF DESCRIPTION OF THE DRAWINGS

The invention will now be described with reference to the figures in the accompanying drawings.

DETAILED DESCRIPTION OF THE INVENTION

Definitions

Figure 1:
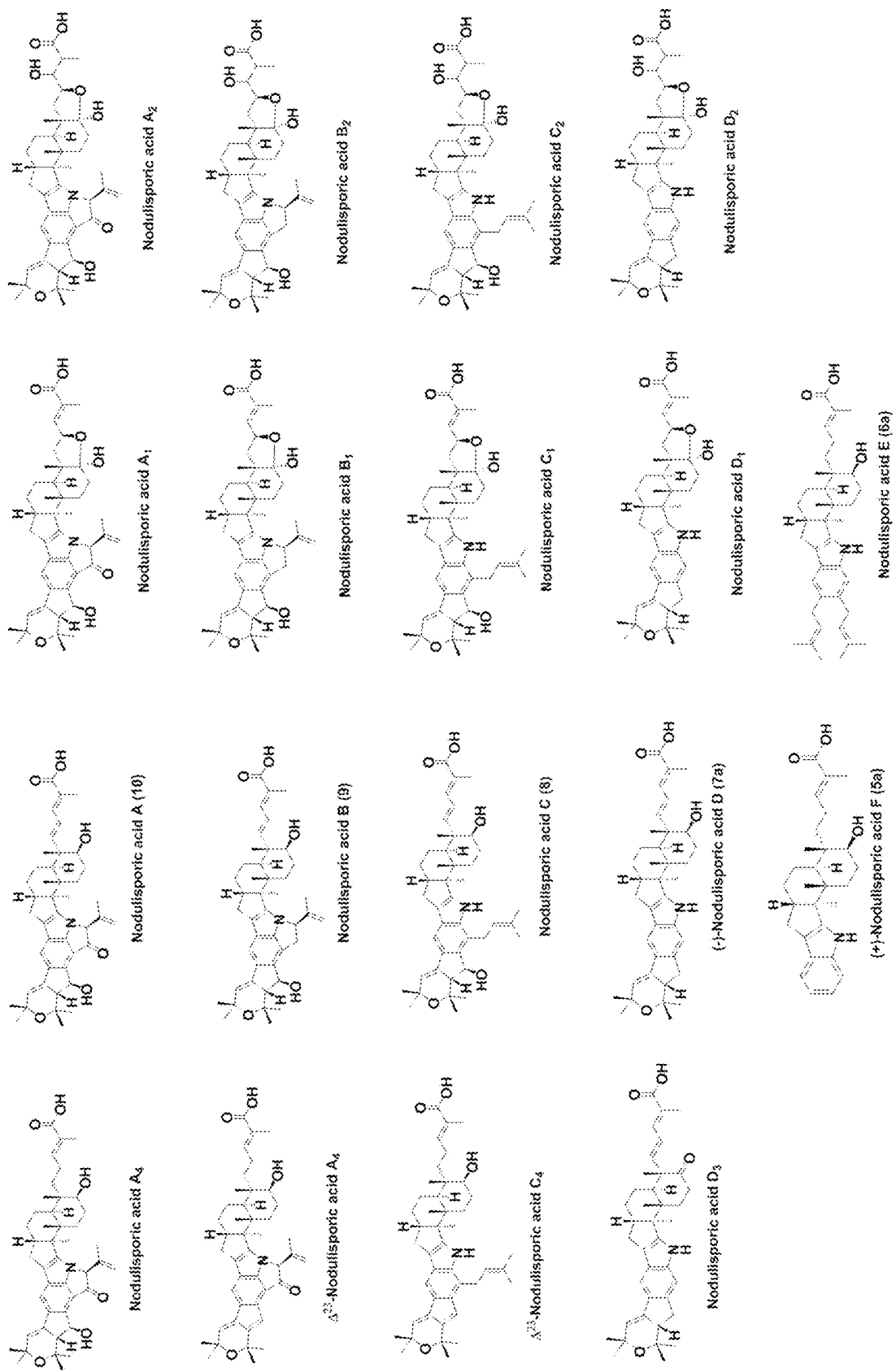
FIG. 1: Collection of known nodulisporic acids (NAs).

The term "comprising" as used in this specification and claims means "consisting at least in part of"; that is to say when interpreting statements in this specification and claims which include "comprising", the features prefaced by this term in each statement all need to be present but other features can also be present. Related terms such as "comprise" and "comprised" are to be interpreted in similar manner.

The term "consisting essentially of" as used herein means the specified materials or steps and those that do not materially affect the basic and novel characteristic(s) of the claimed invention.

The term "consisting of" as used herein means the specified materials or steps of the claimed invention, excluding any element, step, or ingredient not specified in the claim.

The terms "recognition site" and "restriction site" are used interchangeably herein and mean the same thing. These terms as used herein with reference to a restriction enzyme mean the nucleic acid sequence or sequences of a polynucleotide that define the binding site on the polynucleotide for a given restriction enzyme.

The term "indole diterpene (IDT) compound" or "indole diterpenoid" refers to any compound derived from an indole containing precursor, preferably indole-3-glycerol phosphate 1b, and geranylgeranyl pyrophosphate (GGPP) 1a.

In some embodiments an IDT compound is selected from the group consisting of GGI 2, emindole SB 4a, and NAF 5a.

The term "genetic construct" refers to a polynucleotide molecule, usually double-stranded DNA, which has been conjugated to another polynucleotide molecule. In one non-limiting example a genetic construct is made by inserting a first polynucleotide molecule into a second polynucleotide molecule, for example by restriction/ligation as known in the art. In some embodiments, a genetic construct comprises a single polynucleotide module, at least two polynucleotide modules, or a series of multiple polynucleotide modules assembled into a single contiguous polynucleotide molecule (also referred to herein as a "multigene construct"), but not limited thereto.

The term "genetic construct" refers to a polynucleotide molecule, usually double-stranded DNA, which has been conjugated to another polynucleotide molecule. In one non-limiting example a genetic construct is made by inserting a first polynucleotide molecule into a second polynucleotide molecule, for example by restriction/ligation as known in the art. In some embodiments, a genetic construct comprises a single polynucleotide module, at least two polynucleotide modules, or a series of multiple polynucleotide modules assembled into a single contiguous polynucleotide molecule (also referred to herein as a "multigene construct"), but not limited thereto.

A genetic construct may contain the necessary elements that permit transcription of a polynucleotide molecule, and, optionally, for translating the transcript into a polypeptide. A polynucleotide molecule comprised in and/or by the gene construct may be derived from the host cell, or may be derived from a different cell or organism and/or may be a recombinant polynucleotide. Once inside the host cell the genetic construct may become integrated in the host chromosomal DNA. The genetic construct may be linked to a vector.

The term "transcription unit" (TU) as used herein refers to a polynucleotide comprising a sequence of nucleotides that code for a single RNA molecule including all the nucleotide sequences necessary for transcription of the single RNA molecule, including a promoter, an RNA-coding sequence, and a terminator, but not limited thereto.

The term "transcription unit module" (TUM) as used herein refers to a polynucleotide comprising a sequence of nucleotides that encode a single RNA molecule, or parts thereof; or that encode a protein coding sequence (CDS), or parts thereof; or that encode sequence elements, or parts thereof, that control transcription of that RNA molecule; or that encode sequence elements or parts thereof that control translation of the CDS. Such sequence elements may include, but are not limited to, promoters, untranslated regions (UTRs), terminators, polyadenylation signals, ribosome binding sites, transcriptional enhancers and translational enhancers.

The term "multigene construct" as used herein means a genetic construct that is a polynucleotide comprising at least two TUs.

The term "marker" as used herein means a nucleic acid sequence in a polynucleotide that encodes a selectable marker or scorable marker.

The term "selectable marker" as used herein refers to a TU, which when introduced into a cell, confers at least one trait on the cell that allows the cell to be selected based on the presence or absence of that trait. In one embodiment the cell is selected based on survival under conditions that kill cells not comprising the at least one selectable marker.

The term "scorable marker" as used herein refers to a TU, which when introduced into a cell, confers at least one trait on the cell that allows the cell to be scored based on the presence or absence of that trait. In one embodiment the cell comprising the TU is scored by identifying the cell phenotypically from a plurality of cells.

The term "genetic element" as used herein refers to any polynucleotide sequence that is not a TU or does not form part of a TU. Such polynucleotide sequences may include, but are not limited to origins of replication for plasmids and viruses, centromeres, telomeres, repeat sequences, sequences used for homologous recombination, site-specific recombination sequences, and sequences controlling DNA transfer between organisms.

The term "vector" as used herein refers to any type of polynucleotide molecule that may be used to manipulate genetic material so that it can be amplified, replicated, manipulated, partially replicated, modified and/or expressed, but not limited thereto. In some embodiments a vector may be used to transport a polynucleotide comprised in that vector into a cell or organism.

The term "source vector" as used herein refers to a vector into which polynucleotide sequences of interest can be cloned. In some embodiments the polynucleotide sequences are TUs and TUMs as described herein. In some embodiments a source vector is selected from the group consisting of plasmids, bacterial artificial chromosomes (BACs), phage artificial chromosomes (PACs), yeast artificial chromosomes (YACs), bacteriophage, phagemids, and cosmids. In some embodiments, a source vector comprising a polynucleotide sequence of interest is termed an entry clone. In some embodiments the entry clone can serve as a shuttle or destination vector for receiving further polynucleotide sequences.

The term "shuttle vector" as used herein refers to a vector into which polynucleotide sequences of interest can be cloned and from which they can be manipulated. In some embodiments the polynucleotide sequences are TUs and TUMs as described herein. In some embodiments a shuttle vector is selected from the group consisting of plasmids, BACs, PACs, YACs, bacteriophage, phagemids, and cosmids. In some embodiments, a shuttle vector comprising a polynucleotide sequence of interest can serve as a destination vector for receiving further polynucleotide sequences.

The term "destination vector" as used herein refers to a vector into which polynucleotide sequences of interest can be cloned. In some embodiments the polynucleotide sequences are TUs and TUMs as described herein. In some embodiments a destination vector is selected from the group consisting of plasmids, BACs, PACs, YACs, bacteriophage, phagemids, and cosmids. In some embodiments, a destination vector comprising a polynucleotide sequence of interest is an entry clone. In some embodiments the entry clone can serve as a destination vector for receiving further polynucleotide sequences.

The term "polynucleotide(s)," as used herein, means a single or double-stranded deoxyribonucleotide or ribonucleotide polymer of any length, and include as non-limiting examples, coding and non-coding sequences of a gene, sense and antisense sequences, exons, introns, genomic DNA, cDNA, pre-mRNA, mRNA, rRNA, siRNA, miRNA, tRNA, ribozymes, recombinant polynucleotides, isolated and purified naturally occurring DNA or RNA sequences, synthetic RNA and DNA sequences, nucleic acid probes, primers, fragments, genetic constructs, vectors and modified polynucleotides. Reference to nucleic acids, nucleic acid molecules, nucleotide sequences and polynucleotide sequences is to be similarly understood.

The term "gene" as used herein refers to gene the biologic unit of heredity, self-reproducing and located at a definite position (locus) on a particular chromosome. In one embodiment the particular chromosome is a eukaryotic or bacterial chromosome. The term bacterial chromosome is used interchangeably herein with the term bacterial genome.

The term "gene cluster" as used herein refers to a group of genes located closely together on the same chromosome whose products play a coordinated role in a specific aspect of cellular primary or secondary metabolism. In one example a gene cluster comprises a group of CDSs the products of which all participate in a series of biochemical reactions that comprise the biosynthetic pathway or array that produces a given metabolite, particularly a secondary metabolite.

The term "secondary metabolite" as used herein refers to compounds that are not involved in primary metabolism, and therefore differ from the more prevalent macromolecules such as proteins and nucleic acids that make up the basic machinery of life.

The terms "under conditions wherein the . . . enzyme is active" and "under conditions wherein the . . . enzymes are active", and grammatical variations thereof when used in reference to enzyme activity mean that the enzyme will perform it's expected function; e.g., a restriction endonuclease will cleave a nucleic acid at an appropriate restriction site, and a DNA ligase will covalently join two polynucleotides together.

The term "endogenous" as used herein refers to a constituent of a cell, tissue or organism that originates or is produced naturally within that cell, tissue or organism. An "endogenous" constituent may be any constituent including but not limited to a polynucleotide, a polypeptide including a non-ribosomal polypeptide, a fatty acid or a polyketide, but not limited thereto.

The term "exogenous" as used herein refers to any constituent of a cell, tissue or organism that does not originate or is not produced naturally within that cell, tissue or organism. An exogenous constituent may be, for example, a polynucleotide sequence that has been introduced into a cell, tissue or organism, or a polypeptide expressed in that cell, tissue or organism from that polynucleotide sequence.

"Naturally occurring" as used herein with reference to a polynucleotide sequence according to the invention refers to a primary polynucleotide sequence that is found in nature. A synthetic polynucleotide sequence that is identical to a wild polynucleotide sequence is, for the purposes of this disclosure, considered a naturally occurring sequence. What is important for a naturally occurring polynucleotide sequence is that the actual sequence of nucleotide bases that comprise the polynucleotide is found or known from nature.

For example, a wild type polynucleotide sequence is a naturally occurring polynucleotide sequence, but not limited thereto. A naturally occurring polynucleotide sequence also refers to variant polynucleotide sequences as found in nature that differ from wild type. For example, allelic variants and naturally occurring recombinant polynucleotide sequences due to hybridization or horizontal gene transfer, but not limited thereto.

"Non-naturally occurring" as used herein with reference to a polynucleotide sequence according to the invention refers to a polynucleotide sequence that is not found in nature. Examples of non-naturally occurring polynucleotide sequences include artificially produced mutant and variant polynucleotide sequences, made for example by point mutation, insertion, or deletion, but not limited thereto. Non-naturally occurring polynucleotide sequences also include chemically evolved sequences. What is important for a non-naturally occurring polynucleotide sequence according to the invention is that the actual sequence of nucleotide bases that comprise the polynucleotide is not found or known from nature.

The term, "wild type" when used herein with reference to a polynucleotide refers to a naturally occurring; non-mutant form of a polynucleotide. A mutant polynucleotide means a polynucleotide that has sustained a mutation as known in the art, such as point mutation, insertion, deletion, substitution, amplification or translocation, but not limited thereto.

The term, "wild type" when used herein with reference to a polypeptide refers to a naturally occurring, non-mutant form of a polypeptide. A wild type polypeptide is a polypeptide that is capable of being expressed from a wild type polynucleotide.

The term "coding sequence" or "open reading frame" (ORF) refers to the sense strand of a genomic DNA sequence or a cDNA sequence that is capable of producing a transcription product and/or a polypeptide under the control of appropriate regulatory sequences. The CDS is identified by the presence of a 5' translation start codon and a 3' translation stop codon. When inserted into a genetic construct or an expression cassette, a "coding sequence" (CDS) is capable of being expressed when it is operably linked to a promoter sequence and/or other regulatory elements.

"Operably-linked" means that the sequence to be expressed is placed under the control of regulatory elements.

"Regulatory elements" as used herein refers to any nucleic acid sequence element that controls or influences the expression of a polynucleotide insert from a vector, genetic construct or expression cassette and includes promoters, transcription control sequences, translation control sequences, origins of replication, tissue-specific regulatory elements, temporal regulatory elements, enhancers, polyadenylation signals, repressors and terminators. Regulatory elements can be "homologous" or "heterologous" to the polynucleotide insert to be expressed from a genetic construct, expression cassette or vector as described herein. When a genetic construct, expression cassette or vector as described herein is present in a cell, a regulatory element can be "endogenous", "exogenous", "naturally occurring" and/or "non-naturally occurring" with respect to cell.

The term "noncoding region" refers to untranslated sequences that are upstream of the translational start site and downstream of the translational stop site. These sequences are also referred to respectively as the 5' UTR and the 3' UTR. These regions include elements required for transcription initiation and termination and for regulation of translation efficiency.

Terminators are sequences, which terminate transcription, and are found in the 3' untranslated ends of genes downstream of the translated sequence. Terminators are important determinants of mRNA stability and in some cases have been found to have spatial regulatory functions.

The term "promoter" refers to nontranscribed cis-regulatory elements upstream of the coding region that regulate the transcription of a polynucleotide sequence. Promoters comprise cis-initiator elements which specify the transcription initiation site and conserved boxes. In one non-limiting example, bacterial promoters may comprise a "Pribnow box" (also known as the −10 region), and other motifs that are bound by transcription factors and promote transcription. Promoters can be homologous or heterologous with respect to polynucleotide sequence to be expressed. When the polynucleotide sequence is to be expressed in a cell, a promoter may be an endogenous or exogenous promoter. Promoters can be constitutive promoters, inducible promoters or regulatable promoters as known in the art.

"Homologous" as used herein with reference to polynucleotide regulatory elements, means a polynucleotide regulatory element that is a native and naturally-occurring polynucleotide regulatory element. A homologous polynucleotide regulatory element may be operably linked to a polynucleotide of interest such that the polynucleotide of interest can be expressed from a TU, genetic element or vector according to the invention.

"Homologous" as used herein with reference to polynucleotide or polypeptide in a host organism means that the polynucleotide or polypeptide is a native and naturally-occurring polynucleotide or polypeptide within that host organism. A homologous polynucleotide may be operably linked to a homologous or heterologous regulatory element so that a homologous polypeptide may be expressed from a TU, genetic element or vector comprising the homologous polynucleotide as described herein.

"Introduced Homologous" as used herein with reference to polynucleotide or polypeptide in a host organism means that the polynucleotide or polypeptide is a native and naturally-occurring polynucleotide or polynucleotide within that host organism that has been introduced into the organism by experimental techniques. A introduced homologous polynucleotide may be operably linked to a homologous or heterologous regulatory element so that a homologous polypeptide may be expressed from a TU, genetic element or vector comprising the homologous polynucleotide as described herein.

"Heterologous" as used herein with reference to polynucleotide regulatory elements, means a polynucleotide regulatory element that is not a native and naturally-occurring polynucleotide regulatory element. A heterologous polynucleotide regulatory element is not normally associated with the CDS to which it is operably linked. A heterologous regulatory element may be operably linked to a polynucleotide of interest such that the polynucleotide of interest can be expressed from a, vector, genetic construct or expression cassette according to the invention. Such promoters may include promoters normally associated with other genes, ORFs or coding regions, and/or promoters isolated from any other bacterial, viral, eukaryotic, or mammalian cell.

"Heterologous" as used herein with reference to a polynucleotide or polypeptide in a host organism means a polynucleotide or polypeptide that is not a native and naturally-occurring polynucleotide or polypeptide in that host organism. A heterologous polynucleotide may be operably linked to a heterologous or homologous regulatory element so that a heterologous polypeptide may be expressed from a TU, genetic element or vector comprising the heterologous polynucleotide as described herein.

The terms "heterologously expressing" and "heterologous expression" mean the expression of a heterologous polypeptide in a host cell.

A "biochemical reaction in the biosynthetic pathway leading from GGI 2 to NAA 10" means one of the specific reactions catalyzed by one of the specific enzymes involved in transforming the substrate molecule GGI 2 through the following intermediates: mono-expoxidized GGI 3a, emindole SB 4a, NAF 5a, NAE 6a, NAD 7a, NAC 8, NAB 9, to NAA 10, and does not include similar enzymes within a host cell that may have similar functions but that do not act on the particular named intermediates above.

A "functional variant or fragment thereof" of a polypeptide is a subsequence of the polypeptide that performs a function that is required for the biological activity or binding of that polypeptide and/or provides the three dimensional structure of the polypeptide. The term may refer to a polypeptide, an aggregate of a polypeptide such as a dimer or other multimer, a fusion polypeptide, a polypeptide fragment, a polypeptide variant, or functional polypeptide derivative thereof that is capable of performing the polypeptide activity.

"Isolated" as used herein with reference to polynucleotide or polypeptide sequences describes a sequence that has been removed from its natural cellular environment. An isolated molecule may be obtained by any method or combination of methods as known and used in the art, including biochemical, recombinant, and synthetic techniques. The polynucleotide or polypeptide sequences may be prepared by at least one purification step.

"Isolated" when used herein in reference to a cell or host cell describes to a cell or host cell that has been obtained or removed from an organism or from its natural environment and is subsequently maintained in a laboratory environment as known in the art. The term encompasses single cells, per se, as well as cells or host cells comprised in a cell culture and can include a single cell or single host cell.

The term "isolated host cell" as used herein with reference to a fungal host cell encompasses single cells of unicellular fungi and the hyphae and mycelia of filamentous fungi including septate and non-septate forms.

The term "recombinant" refers to a polynucleotide sequence that is removed from sequences that surround it in its natural context and/or is recombined with sequences that are not present in its natural context. A "recombinant" polypeptide sequence is produced by translation from a "recombinant" polynucleotide sequence.

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the polypeptides useful in the invention have biological activities that are the same or similar to those of a corresponding wild type molecule; i.e., the parent polypeptides or polynucleotides.

In certain embodiments, variants of the polypeptides described herein have biological activities that are similar, or that are substantially similar to their corresponding wild type molecules. In certain embodiments the similarities are similar activity and/or binding specificity.

In certain embodiments, variants of polypeptides described herein have biological activities that differ from their corresponding wild type molecules. In certain embodiments the differences are altered activity and/or binding specificity.

The term "variant" with reference to polynucleotides and polypeptides encompasses all forms of polynucleotides and polypeptides as defined herein.

Variant polynucleotide sequences preferably exhibit at least 50%, at least 60%, preferably at least 70%, preferably at least 71%, preferably at least 72%, preferably at least 73%, preferably at least 74%, preferably at least 75%, preferably at least 76%, preferably at least 77%, preferably at least 78%, preferably at least 79%, preferably at least 80%, preferably at least 81%, preferably at least 82%, preferably at least 83%, preferably at least 84%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, and preferably at least 99% identity to a sequence of the present invention. Identity is found over a comparison window of at least 8 nucleotide positions, preferably at least 10 nucleotide positions, preferably at least 15 nucleotide positions, preferably at least 20 nucleotide positions, preferably at least 27 nucleotide positions, preferably at least 40 nucleotide positions, preferably at least 50 nucleotide positions, preferably at least 60 nucleotide positions, preferably at least 70 nucleotide positions, preferably at least 80 nucleotide positions, preferably over the entire length of a polynucleotide used in or identified according to a method of the invention.

Polynucleotide variants also encompass those which exhibit a similarity to one or more of the specifically identified sequences that is likely to preserve the functional equivalence of those sequences and which could not reasonably be expected to have occurred by random chance.

Polynucleotide sequence identity and similarity can be determined readily by those of skill in the art.

Variant polynucleotides also encompasses polynucleotides that differ from the polynucleotide sequences described herein but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also included in the invention. A skilled artisan will be aware of methods for making phenotypically silent amino acid substitutions (see, e.g., Bowie et al., 1990, Science 247, 1306).

The term "variant" with reference to polypeptides also encompasses naturally occurring, recombinantly and synthetically produced polypeptides. Variant polypeptide sequences preferably exhibit at least 35%, preferably at least 40%, preferably at least 50%, preferably at least 60%, preferably at least 70%, preferably at least 71%, preferably at least 72%, preferably at least 73%, preferably at least 74%, preferably at least 75%, preferably at least 76%, preferably at least 77%, preferably at least 78%, preferably at least 79%, preferably at least 80%, preferably at least 81%, preferably at least 82%, preferably at least 83%, preferably at least 84%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, and preferably at least 99% identity to a sequence of the present invention. Identity is found over a comparison window of at least 2 amino acid positions, preferably at least 3 amino acid positions, preferably at least 4 amino acid positions, preferably at least 5 amino acid positions, preferably at least 7 amino acid positions, preferably at least 10 amino acid positions, preferably at least 15 amino acid positions, preferably at least 20 amino acid positions, preferably over the entire length of a polypeptide used in or identified according to a method of the invention.

Polypeptide variants also encompass those which exhibit a similarity to one or more of the specifically identified sequences that is likely to preserve the functional equivalence of those sequences and which could not reasonably be expected to have occurred by random chance.

Polypeptide sequence identity and similarity can be determined readily by those of skill in the art.

A variant polypeptide includes a polypeptide wherein the amino acid sequence differs from a polypeptide herein by one or more conservative amino acid or non-conservative substitutions, deletions, additions or insertions which do not affect the biological activity of the peptide.

Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine.

Analysis of evolved biological sequences has shown that not all sequence changes are equally likely, reflecting at least in part the differences in conservative versus non-conservative substitutions at a biological level. For example, certain amino acid substitutions may occur frequently, whereas others are very rare. Evolutionary changes or substitutions in amino acid residues can be modelled by a scoring matrix also referred to as a substitution matrix. Such matrices are used in bioinformatics analysis to identify relationships between sequences and are known to the skilled worker.

Other variants include peptides with modifications which influence peptide stability. Such analogs may contain, for example, one or more non-peptide bonds (which replace the peptide bonds) in the peptide sequence. Also included are analogs that include residues other than naturally occurring L-amino acids, e.g. D-amino acids or non-naturally occurring synthetic amino acids, e.g. beta or gamma amino acids and cyclic analogs.

Substitutions, deletions, additions or insertions may be made by mutagenesis methods known in the art. A skilled worker will be aware of methods for making phenotypically silent amino acid substitutions. See for example Bowie et al., 1990, Science 247, 1306.

A polypeptide as used herein can also refer to a polypeptide that has been modified during or after synthesis, for example, by biotinylation, benzylation, glycosylation, phosphorylation, amidation, by derivatization using blocking/protecting groups and the like. Such modifications may increase stability or activity of the polypeptide.

The terms "modulate(s) expression", "modulated expression" and "modulating expression" of a polynucleotide or polypeptide, are intended to encompass the situation where genomic DNA corresponding to a polynucleotide to be expressed according to the invention is modified thus leading to modulated expression of a polynucleotide or polypeptide of the invention. Modification of the genomic DNA may be through genetic transformation or other methods known in the art for inducing mutations. The "modulated expression" can be related to an increase or decrease in the amount of messenger RNA and/or polypeptide produced and may also result in an increase or decrease in the activity of a polypeptide due to alterations in the sequence of a polynucleotide and polypeptide produced.

The terms "modulate(s) activity", "modulated activity" and "modulating activity" of a polynucleotide or polypeptide, are intended to encompass the situation where genomic DNA corresponding to a polynucleotide to be expressed according to the invention is modified thus leading to modulated expression of a polynucleotide or modulated expression or activity of polypeptide of the invention. Modification of the genomic DNA may be through genetic transformation or other methods known in the art for inducing mutations. The "modulated activity" can be related to an increase or decrease in the amount of messenger RNA and/or polypeptide produced and may also result in an increase or decrease in the functional activity of a polypeptide due to alterations in the sequence of a polynucleotide and polypeptide produced.

It is intended that reference to a range of numbers disclosed herein (for example 1 to 10) also incorporates reference to all related numbers within that range (for example, 1, 1.1, 2, 3, 3.9, 4, 5, 6, 6.5, 7, 8, 9 and 10) and also any range of rational numbers within that range (for example 2 to 8, 1.5 to 5.5 and 3.1 to 4.7) and, therefore, all sub-ranges of all ranges expressly disclosed herein are expressly disclosed. These are only examples of what is specifically intended and all possible combinations of numerical values between the lowest value and the highest value enumerated are to be considered to be expressly stated in this application in a similar manner.

DETAILED DESCRIPTION

Figure 2:
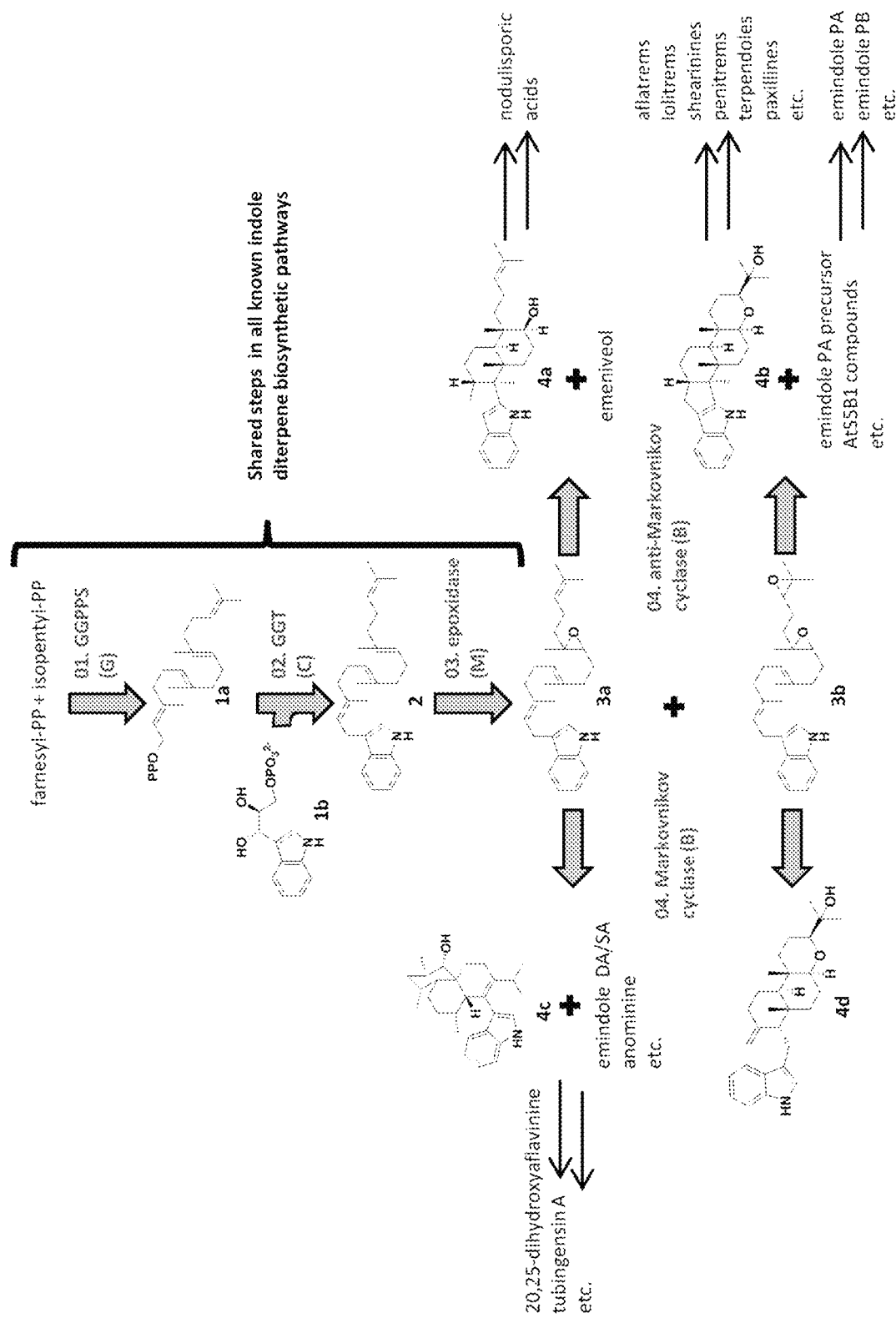
FIG. 2: Branch points in the biosynthetic pathway of indole diterpenes (IDTs) that give rise to the diverse array of IDT structures. Arrows represent enzymatic steps in IDT biosynthesis.
Figure 3:
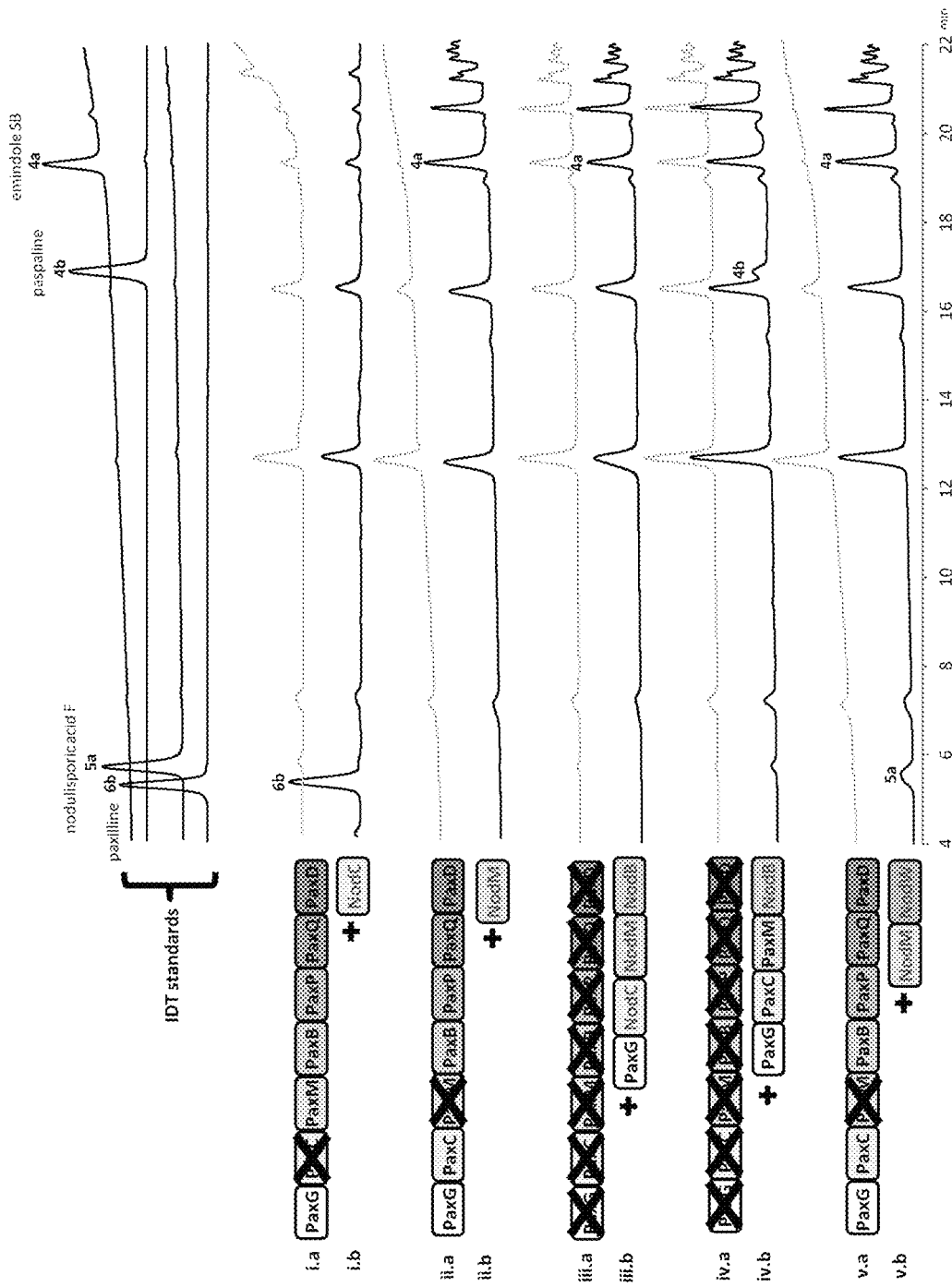
FIG. 3: HPLC analysis (271 nm) of extracts of *P. paxilli* knockout (KO) strains (in gray (••••••)) expressing different *H. pulicicidum* (Nod) enzymes and/or *P. paxilli* (Pax) enzymes (in black (-)). A black X covers the enzyme(s) that are not expressed in the *P. paxilli* KO strains (traces i.a, ii.a, iii.a, iv.a, and v.a). The enzyme(s) that have been newly expressed in the *P. paxilli* KO strain are depicted below the corresponding KO strain and next to their UV traces (i.b, ii.b, iii.b, iv.b, and v.b). Notably there is a compound that elutes at the same retention time as emindole SB 4a, but emindole SB 4a is only present in three traces (ii.b, iii.b, and v.b) as confirmed by corresponding 406.31±0.01 m/z EICs (FIGS. 5, 6, and 9). Traces correspond to fungal extracts as follows: i.a=PN2290, i.b=pKV27:PN2690, ii.a=PN2257, ii.b=pKV63:PN2257, iii.a=PN2250, iii.b=pSK66:PN2250, iv.a=PN2250, iv.b=pKV74:PN2250, v.a=PN2257, v.b=pKV64:PN2257.
Figure 4:
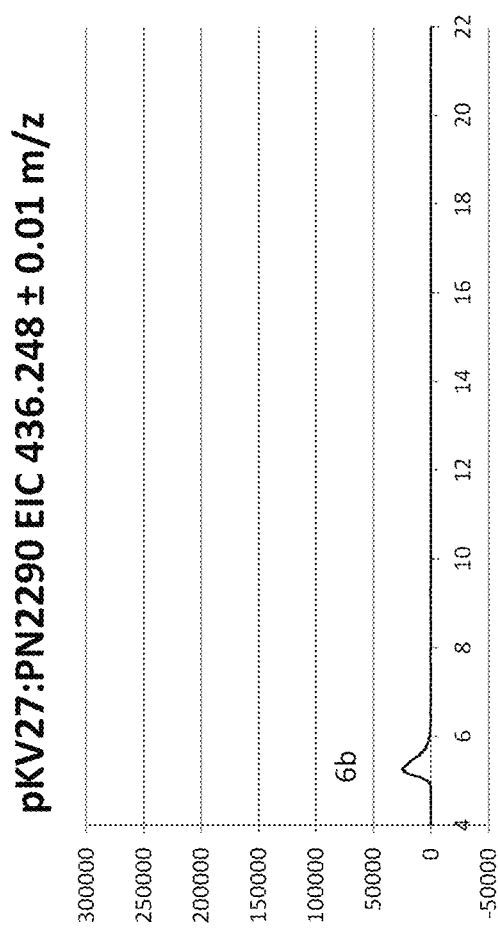
FIG. 4: Extracted ion chromatogram for pKV27:PN2290 (nodC:ΔpaxC) showing MS peak for paxilline 6b (5.3 min, 436.248±0.01 m z).
Figure 5:
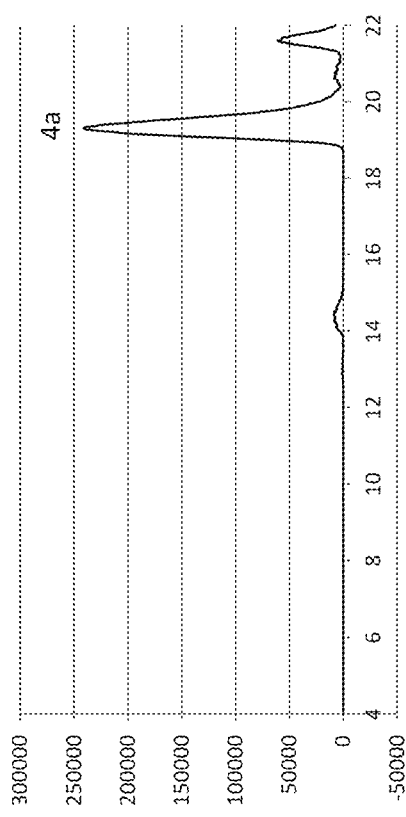
FIG. 5: Extracted ion chromatograms for pKV63:PN2257 (nodM:ΔpaxM) showing MS peak for emindole SB 4a (19.3 min, 406.31±0.01 m z) but not paspaline 4b (17.6 min, 422.305±0.01 m z).
Figure 5:
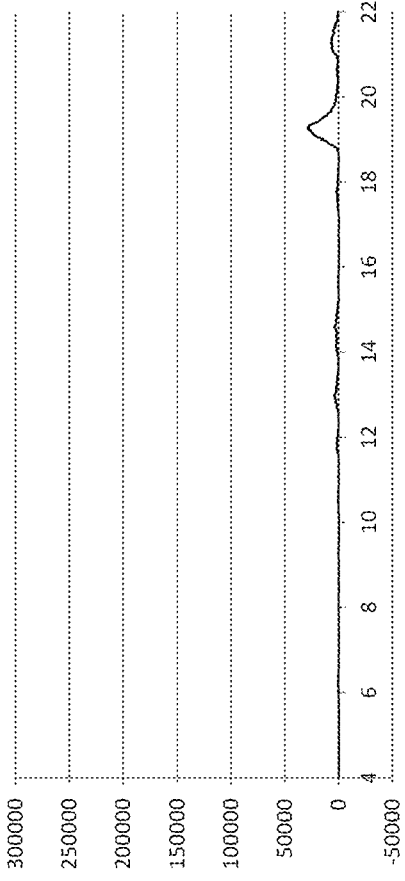
Figure 6:
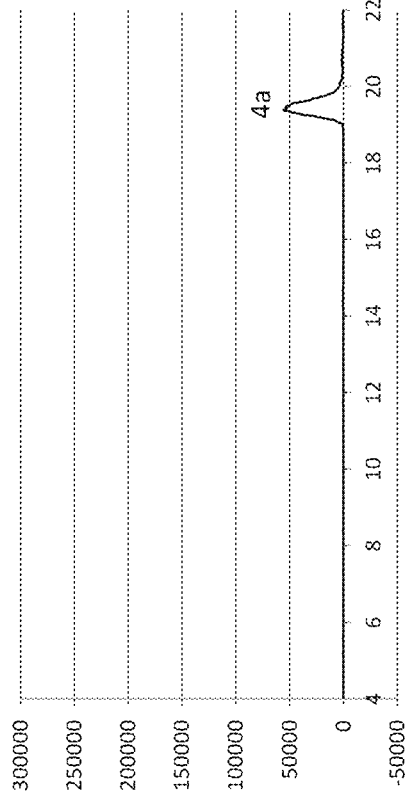
FIG. 6: Extracted ion chromatograms for pSK66:PN2250 (paxG, nodC, nodM, and nodB:ΔPAX cluster) showing MS peak for emindole SB 4a (19.3 min, 406.31±0.01 m z) but not paspaline 4b (17.6 min, 422.305±0.01 m z).
Figure 6:
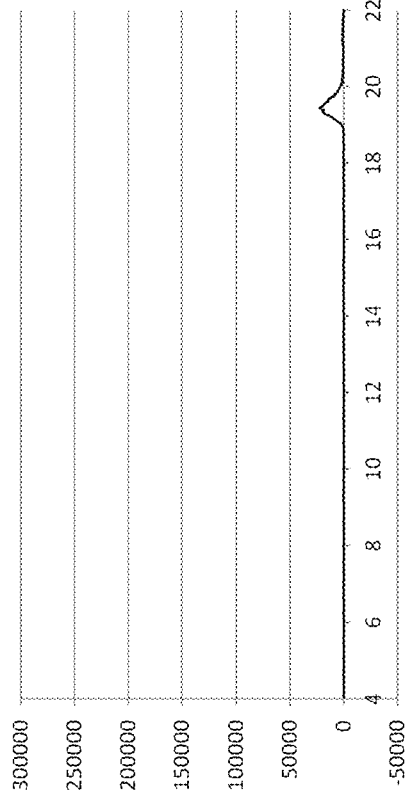
Figure 7:
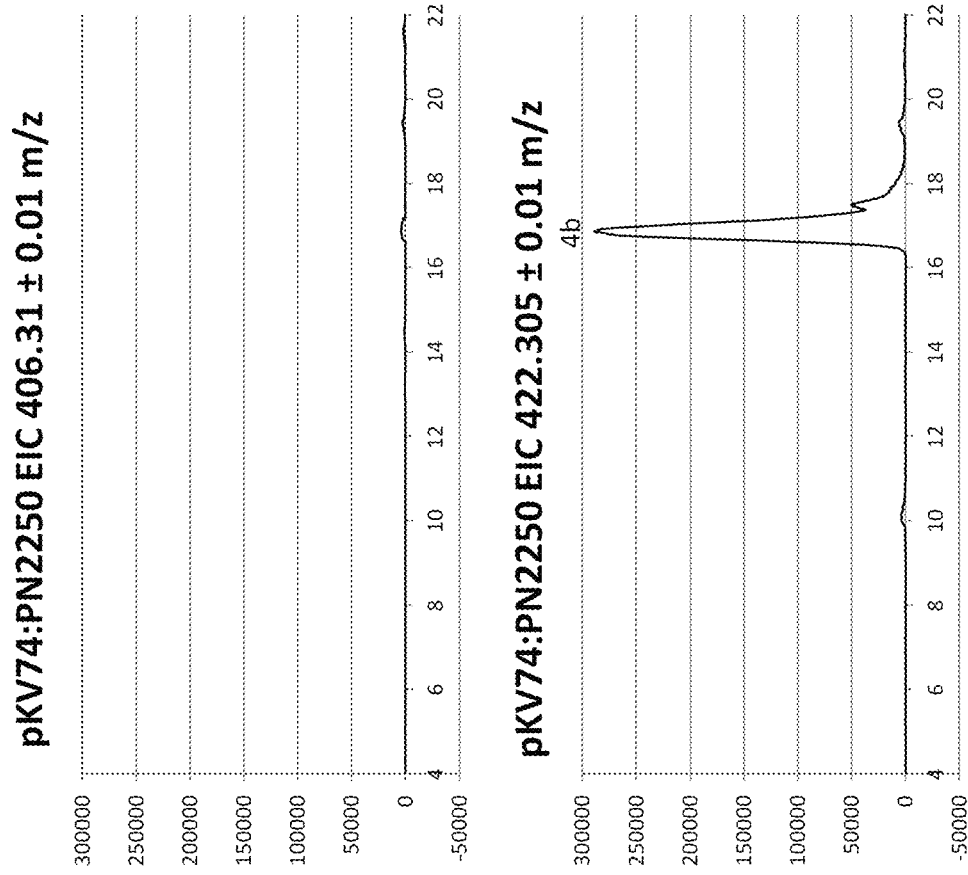
FIG. 7: Extracted ion chromatogram for pKV74:PN2250 (paxG, paxC, paxM, nodB:ΔPAX cluster) showing MS peak for paspaline 4b (17.6 min, 422.305±0.01 m z) but not emindole SB 4a (19.3 min, 406.31±0.01 m z).
Figure 8:
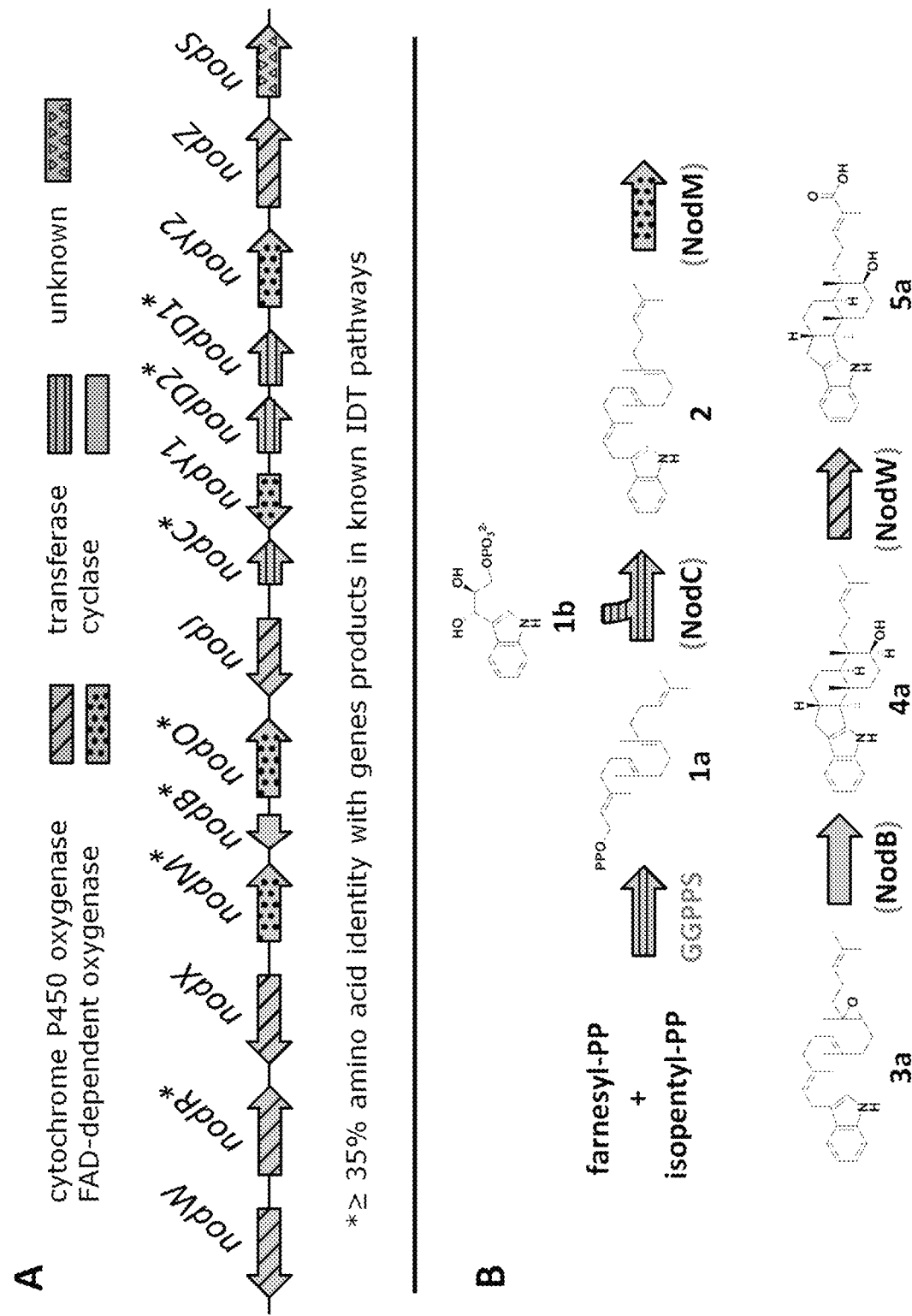
FIG. 8: Depiction of the predicted NA gene cluster from *H. pulicicidum* (A) and the NAF 5a biosynthetic pathway (B). Arrows represent individual genes and arrow decorations represent gene function. Figure is not to exact scale and does not include exon/intron structure. Notably the gene cluster lacks a GGPPS responsible for the first secondary-metabolic step in IDT synthesis.
Figure 9:
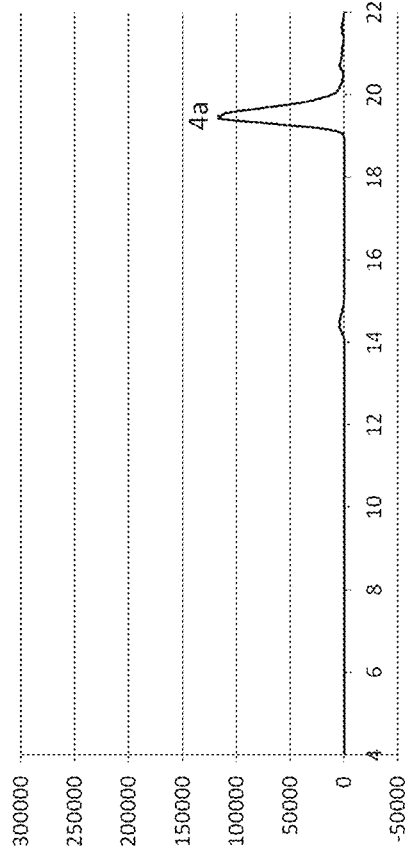
FIG. 9: Extracted ion chromatograms for pKV64:PN2257 (nodM and nodW:ΔpaxM) showing MS peaks for emindole SB 4a (19.3 min, 406.31±0.01 m z) and NAF 5a (6.2 min, 436.284±0.01 m z).
Figure 9:
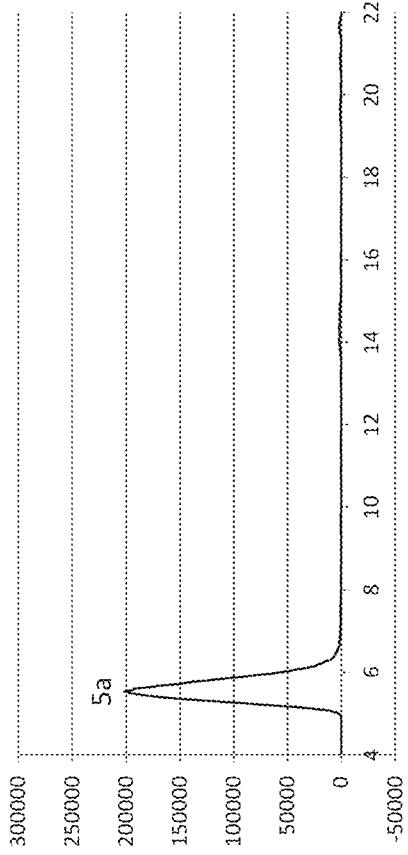
Figure 10:
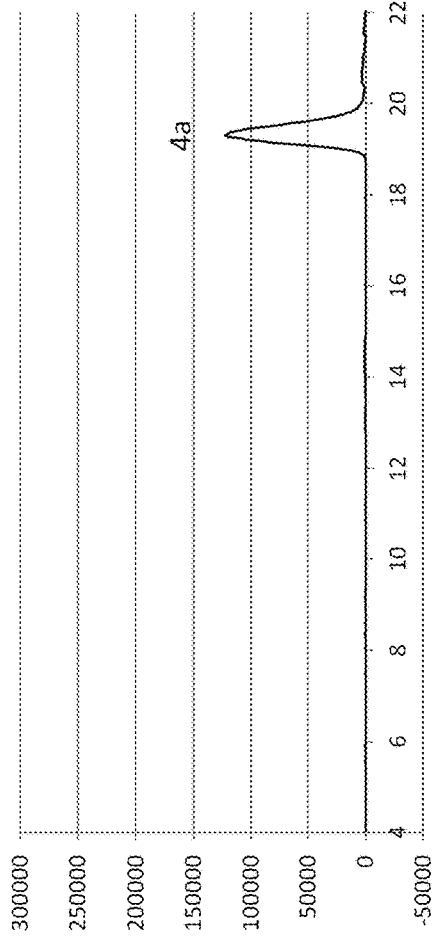
FIG. 10: Extracted ion chromatograms for pSK68: PN2250 (paxG, nodC, nodM, nodB, and nodW: ΔPAX cluster) showing MS peaks for emindole SB 4a (19.3 min, 406.31±0.01 m z) and NAF 5a (6.2 min, 436.284±0.01 m z).
Figure 10:
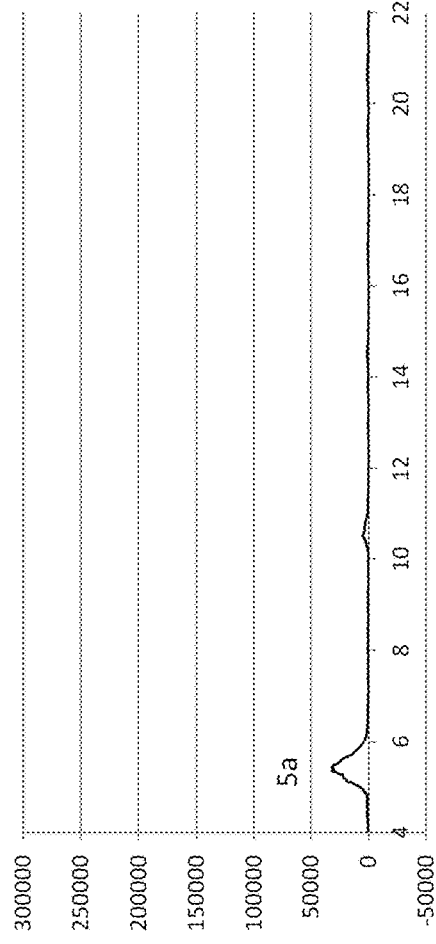

Since the identification of the biosynthetic pathway for the IDT paxilline 6b in *Penicillium paxilli*, gene functionality in seven other IDT biosynthetic pathways has been elucidated. These IDT pathways share homologous genes that encode enzymes for the first three steps in IDT biosynthesis (FIG. 2): (I) a geranylgeranyl pyrophosphate synthase (GGPPS), converts farnesyl pyrophosphate and isopentyl pyrophosphate into GGPP 1a, (II) a geranylgeranyl transferase (GGT), catalyzes the indole condensation of GGPP 1a and indole-3-glycerol phosphate 1b to make GGI 2, and (III) a regioselective flavin adenine dinucleotide (FAD) dependent epoxidase, creates the single and/or double epoxidized-GGI products 3a/3b. At the fourth enzymatic step, involving IDT cyclization, the pathways diverge into four key branches giving rise to mono/di-oxygenated anti-Markovnikov-derived cyclic cores like emindole SB 4a and paspaline 4b, or mono/di-oxygenated Markovnikov-derived cyclic cores like aflavinine 4c and the emindole DB 4d. These cyclic cores are often further modified with decorative enzymes that create the bioactive diversity seen across IDTs.

NAs are bioactive IDTs produced by *Hypoxylon pulicicidum*, with NAA 10 being of particular significance due to its highly potent insecticidal activity against blood-feeding arthropods and lack of mammalian toxicity. However, as described herein, the production of NAA 10 by direct synthesis has not been achieved, and the biosynthetic production of this compound in quantities that would be useful at even a small scale commercial level would be difficult to achieve, if at all.

Accordingly, the present invention generally relates to a series of isolated genes from the fungus, *H. pulicicidum*, which combined, form a gene cluster that mediates the production of NAs, and to the use of that gene cluster to direct the heterologous expression of NAs in an isolated host cell, preferably an isolated fungal cell. Using a recently developed technique for manipulating gene sequences termed the Modular Idempotent DNA Assembly System (MIDAS), the inventors have reconstituted the biosynthetic pathway for NAF 5a from *H. pulicicidum* in an alternate fungal host, *Penicillium paxilli*. The MIDAS platform and method of using the MIDAS platform are described herein, and related patent application AU2017903955, the entirety of which is incorporated herein by reference.

The inventors analyzed the genomic sequence of *H. pulicicidum* and identified a cluster comprising 15 predicted coding sequences (CDSs): nodW cDNA (SEQ ID NO:2) and genomic DNA (SEQ ID NO:1), nodR cDNA (SEQ ID NO:5) and genomic DNA (SEQ ID NO:4), nodX cDNA (SEQ ID NO:8) and genomic DNA (SEQ ID NO:7), nodM cDNA (SEQ ID NO:11) and genomic DNA (SEQ ID NO:10), nodB cDNA (SEQ ID NO:14) and genomic DNA (SEQ ID NO:13), nodO cDNA (SEQ ID NO:17) and genomic DNA (SEQ ID NO:16), nodJ cDNA (SEQ ID NO:20) and genomic DNA (SEQ ID NO: 19), nodC cDNA (SEQ ID NO:23) and genomic DNA (SEQ ID NO:22), nodY1 cDNA (SEQ ID NO:26) and genomic DNA (SEQ ID NO:25), nodD2 cDNA (SEQ ID NO:29) and genomic DNA (SEQ ID NO:28), nodD1 cDNA (SEQ ID NO:32) and genomic DNA (SEQ ID NO:31), nodY2 cDNA (SEQ ID NO:35) and genomic DNA (SEQ ID NO:34), nodZ cDNA (SEQ ID NO:38) and genomic DNA (SEQ ID NO:37), nodS cDNA (SEQ ID NO:49) and genomic DNA (SEQ ID NO:48), nodI cDNA (SEQ ID NO:55) and genomic DNA (SEQ ID NO:54) that are expected to encode enzymes necessary for the biosynthesis of NAA 10.

The boundaries of this cluster were determined by identifying flanking genes that have high similarity and syntenic organisation compared with an equivalent genomic locus in another *Hypoxylon* strain that does not produce nodulisporic acids. Details of these predicted genes in the cluster and their proposed function are shown in Table 1. Seven of the cluster genes are homologous to those found in other IDT biosynthetic gene clusters (Tables 2-6). The protein product of the seven predicted genes that are homologous to IDT biosynthesis genes from other fungi have at least 35% amino acid identity to their homologues in the PAX cluster of *P. paxilli*, the JAN cluster of *P. janthinellum*, and/or the PEN cluster of *P. crustosum* and include a GGT (NodC (SEQ ID NO:24)), two FAD-dependent oxidases (NodM (SEQ ID NO:12) and NodO (SEQ ID NO:18)), an IDT cyclase (NodB (SEQ ID NO:15)), two prenyl transferases (NodD2 (SEQ ID NO:30), and NodD1 (SEQ ID NO:33)), and one cytochrome P450 oxygenase (NodR (SEQ ID NO:6)). The other seven putative ORFs were predicted to encode four cytochrome P450 oxygenases (NodW (SEQ ID NO:3), NodX (SEQ ID NO:9), NodJ (SEQ ID NO:21), and NodZ (SEQ ID NO:39)), a pair of paralogous FAD-dependent oxygenases (NodY1 (SEQ ID NO:27), and NodY2 (SEQ ID NO:36)), and two gene products that may be involved in NA biosynthesis with unknown functions (NodS (SEQ ID NO:50), and NodI (SEQ ID NO:56)). Similar to the TER gene cluster from *Chaunopycnis alba* (*Tolypocladium album*) responsible for terpendole biosynthesis, the NOD cluster does not appear to contain a secondary metabolite-specific GGPPS gene. Notably, the inventors identified only one GGPPS-encoding gene in the genome of *H. pulicicidum* and the amino acid sequence of its predicted protein product, its exon/intron structure, and its location outside of the identified cluster strongly suggest that it is responsible for primary metabolic function similar to ggs1 in *P. paxilli*.

To confirm the function of gene products and directly establish their respective roles in NAA 10 biosynthesis the inventors constructed a series of plasmids harbouring various combinations of these genes, which they then transformed into in appropriate *P. paxilli* hosts (Table 7) for heterologous production of NAA 10 precursors. Accordingly, CDSs of the *H. pulicicidum* genes of interest were amplified (see Table 8 for primers) and cloned into a MIDAS Level-1 destination vector, pML1 (Table 9). At MIDAS Level-2, the cloned CDSs were placed under the control of heterologous promoter (ProUTR) and transcriptional terminator (UTRterm) modules to generate full-length TUs (Table 10), which were then used to generate the multi-gene plasmids (Table 11). The inventors used a repertoire of *P. paxilli* knockout strains (Table 7) to carry out functional complementations and pathway reconstitution to determine the functions of genes in the NOD cluster. Following transformation of *P. paxilli* hosts with multi-gene plasmids, the inventors determined the chemical phenotypes of the transformants initially by normal-phase thin-layer chromatography (TLC, results not shown) and subsequently by reversed-phase liquid chromatography-mass spectrometry (LC-MS) analysis of fungal extracts. The inventors purified the newly expressed metabolites, as determined by high resolution mass spectrometry (HRMS), by semi-preparative reversed-phase high-performance liquid chromatography (HPLC) and subjected compounds to nuclear magnetic resonance (NMR) spectroscopic analysis ($^1$H, $^{13}$C, and HSQC, HMBC, COSY) for final identification.

Using this methodology, the inventors identified that nodC (cDNA (SEQ ID NO:23) and genomic DNA (SEQ ID NO:22)) is a functional ortholog of paxC (cDNA (SEQ ID NO:43) and genomic DNA (SEQ ID NO:42)), and that NodC (SEQ ID NO:24) mediates the production of GGI 2, the second step in IDT biosynthesis, in *H. pulicicidum* (FIG. 3, trace i.b, FIG. 4). NodC (SEQ ID NO:24) shares 52.3% amino acid sequence identity with PaxC (SEQ ID NO:44) from *P. paxilli* (Table 2). The inventors also identified that nodM (cDNA (SEQ ID NO:11) and genomic DNA (SEQ ID NO:10)), is a homolog of paxM (cDNA (SEQ ID NO:46) and genomic DNA (SEQ ID NO:45)), and that NodM (SEQ ID NO:12) is a GGI 2 mono-epoxidase that catalyzes the production of monoepoxidized-GGI 3a (FIG. 3, trace ii.b, FIG. 5). NodM (SEQ ID NO:12) shares 48.6% sequence identity with PaxM (SEQ ID NO:47) from *P. paxilli* (Table 3). Notably, the inventors showed that NodM (SEQ ID NO: 12) is specifically a mono-epoxidase, unlike PaxM (SEQ ID NO:47), which is a mono- or di-epoxidase. The inventors further confirmed that NodB (SEQ ID NO:15) from *H. pulicicidum* acts as the IDT cyclase that cyclizes the monoepoxidized-GGI product 3a to form emindole SB 4a (FIG. 3, trace iii.b, FIG. 6) and that nodB (cDNA (SEQ ID NO:14) and genomic DNA (SEQ ID NO:13)) is a functional ortholog of paxB (cDNA (SEQ ID NO:52) and genomic DNA (SEQ ID NO:51)) from *P. paxilli* (FIG. 3, trace iv.b, FIG. 7). NodB (SEQ ID NO:15) from *H. pulicicidum* shares 63% identity with PaxB (SEQ ID NO:53) from *P. paxilli* (Table 4).

The dedicated NAA 10 core is NAF 5a, generated by oxidation of the terminal methyl carbon, C5", of emindole SB 4a (FIG. 8B). Accordingly the inventors confirmed the identity of this oxidase as a P450 oxygenase encoded by *H. pulicicidum* nodW (cDNA (SEQ ID NO:2) and genomic DNA (SEQ ID NO: 1)) by co-expression of nodW (cDNA (SEQ ID NO:2) and genomic DNA (SEQ ID NO:1)) with nodM (cDNA (SEQ ID NO:11) and genomic DNA (SEQ ID NO:10)) into a paxM (cDNA (SEQ ID NO:46) and genomic DNA (SEQ ID NO:45)) deletion background (PN2257) resulting in the production of NAF 5a (FIG. 3, trace v.b, FIG. 9).

To confirm that only five genes are essential for the production of NAF 5a in *P. paxilli*, and to establish that no other *P. paxilli* IDT genes from the PAX cluster in the paxM KO strain (PN2257) were contributing to NAF 5a production, the inventors assembled a multigene construct comprising paxG (genomic DNA (SEQ ID NO:40)) from *P. paxilli*, and nodC (genomic DNA (SEQ ID NO:22)), nodM (genomic DNA (SEQ ID NO:10)), nodB (genomic DNA (SEQ ID NO:13)), and nodW (genomic DNA (SEQ ID NO:1)) from *H. pulicicidum*. This multigene construct was transformed into a *P. paxilli* PAX gene cluster knockout strain (PN2250). As expected, expression of the five genes showed that NAF 5a was produced (FIG. 10) and indicated that these five genes are indeed required to biosynthesize NAF 5a.

Based on the work described herein the inventors disclose the use of heterologous expression to identify the first five steps that deliver the NAA 10 core compound, NAF 5a. In particular, the inventors have confirmed the function of four previously unknown genes from *H. pulicicidum*: nodC (cDNA (SEQ ID NO:23) and genomic DNA (SEQ ID NO:22)), nodM (cDNA (SEQ ID NO:11) and genomic DNA (SEQ ID NO:10)), nodB (cDNA (SEQ ID NO:14) and genomic DNA (SEQ ID NO:13)), and nodW (cDNA (SEQ ID NO:2) and genomic DNA (SEQ ID NO:1)), and discovered a second filamentous fungal species, *H. pulicicidum*, that does not appear to have a secondary metabolic GGPPS gene but can still produce IDTs. Without wishing to be bound by theory, the inventors believe that *H. pulicicidum* relies upon its primary metabolic GGPPSs to provide the GGPP for IDT synthesis. The lack of a secondary-metabolic GGPPS may explain why *H. pulicicidum* produces such low quantities of NAs. The low quantities of NAs produced by *H. pulicicidum* is a challenge for both resolving the biosynthetic details and for usage of the compounds or their derivatives. Using the efficient gene reassembly of MIDAS and heterologous expression in *P. paxilli* the inventors have overcome both these issues. Furthermore, the inventors demonstrated that *P. paxilli*, with its far more favourable growth conditions, is a suitable host for heterologous expression studies, which enabled the inventors to confirm the function of genes more quickly and easily than would have been possible had they relied on the biosynthetic machinery of *H. pulicicidum*.

Elucidation of the biosynthetic routes for heterologous production of NAF 5a in *P. paxilli* provides a reasonable expectation of success in being able to fully identify the gene products from *H. pulicicidum* that are responsible for the 'decoration' steps that lead to the production of fully functionalized NAA 10. This reasonable expectation comes from the identification, by the inventors, of the nucleic acid CDSs that are predicted to encode the enzymes required for prenylation to form nodulisporic acid E 6a, and for oxidations, to form nodulisporic acid D 7a. Each of these nucleic acid sequences has been putatively identified from the *H. pulicicidum* biosynthetic gene cluster described herein. Overall, the inventors work described herein confirms that heterologous expression of IDT genes in a heterologous host is a viable method that can be employed to produce natural products that are difficult to obtain in other ways, and that could be useful across many industries.

Polypeptides

Accordingly, in one aspect the invention relates to an isolated polypeptide comprising an amino acid sequence selected from the group consisting of SEQ ID NO: NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or a functional variant or fragment thereof.

Preferably the functional variant or fragment thereof comprises at least 70%, preferably at least 75%, preferably at least 80%, preferably at least 85%, preferably at least 90%, preferably at least 95%, preferably at least 99% amino acid sequence identity to an amino acid sequence selected from the group consisting of SEQ ID NO: NodW (SEQ ID NO:3), NodR (SEQ ID NO:6), NodX (SEQ ID NO:9), NodM (SEQ ID NO:12), NodB (SEQ ID NO: 15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56).

Preferably the isolated polypeptide comprising NodW (SEQ ID NO:3) or a functional variant or fragment thereof has oxygenase activity, preferably cytochrome P450 oxygenase activity.

Preferably the isolated polypeptide comprising NodR (SEQ ID NO:6) or a functional variant or fragment thereof has oxygenase activity, preferably cytochrome P450 oxygenase activity.

Preferably the isolated polypeptide comprising NodX (SEQ ID NO:9) or a functional variant or fragment thereof has oxygenase activity, preferably cytochrome P450 oxygenase activity.

Preferably the isolated polypeptide comprising NodM (SEQ ID NO:12) or a functional variant or fragment thereof has oxygenase activity, preferably FAD-dependent oxygenase activity.

Preferably the isolated polypeptide comprising NodB (SEQ ID NO:15) or a functional variant or fragment thereof has cyclase activity, preferably IDT cyclase activity.

Preferably the isolated polypeptide comprising NodO (SEQ ID NO:18) or a functional variant or fragment thereof has oxygenase activity, preferably FAD-dependent oxygenase activity.

Preferably the isolated polypeptide comprising NodJ (SEQ ID NO:21) or a functional variant or fragment thereof has oxygenase activity, preferably cytochrome P450 oxygenase activity.

Preferably the isolated polypeptide comprising NodC (SEQ ID NO:24) or a functional variant or fragment thereof has transferase activity, preferably GGT activity.

Preferably the isolated polypeptide comprising NodY1 (SEQ ID NO:27) or a functional variant or fragment thereof has oxygenase activity, preferably FAD-dependent oxygenase activity.

Preferably the isolated polypeptide comprising NodD2 (SEQ ID NO:30) or a functional variant or fragment thereof has transferase activity, preferably prenyl transferase activity.

Preferably the isolated polypeptide comprising NodD1 (SEQ ID NO:33) or a functional variant or fragment thereof has transferase activity, preferably prenyl transferase activity.

Preferably the isolated polypeptide comprising NodY2 (SEQ ID NO:36) or a functional variant or fragment thereof has oxygenase activity, preferably FAD-dependent oxygenase activity.

Preferably the isolated polypeptide comprising NodZ (SEQ ID NO:39) or a functional variant or fragment thereof has oxygenase activity, preferably cytochrome P450 oxygenase activity.

In one embodiment the isolated polypeptide comprises SEQ ID NO: NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or a functional variant or fragment thereof.

In one embodiment the isolated polypeptide consists essentially of SEQ ID NO: NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or a functional variant or fragment thereof.

In one embodiment the isolated polypeptide consists of SEQ ID NO: NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or a functional variant or fragment thereof.

Polynucleotides

In another aspect the invention relates to an isolated polynucleotide encoding a polypeptide comprising an amino acid sequence selected from the group consisting of SEQ ID NO: NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or a functional variant or fragment thereof.

Preferably the functional variant or fragment thereof comprises at least 70%, preferably at least 75%, preferably at least 80%, preferably at least 85%, preferably at least 90%, preferably at least 95%, preferably at least 99% amino acid sequence identity to an amino acid sequence selected from the group consisting of SEQ ID NO: NodW (SEQ ID NO:3), NodR (SEQ ID NO:6), NodX (SEQ ID NO:9), NodM (SEQ ID NO:12), NodB (SEQ ID NO:15), NodO (SEQ ID NO: 18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) a functional variant or fragment thereof.

Preferably the isolated polynucleotide encodes a polypeptide comprising NodW (SEQ ID NO:3) or a functional variant or fragment thereof having oxygenase activity, preferably cytochrome P450 oxygenase activity.

Preferably the isolated polynucleotide encodes a polypeptide comprising NodR (SEQ ID NO:6) or a functional variant or fragment thereof having oxygenase activity, preferably cytochrome P450 oxygenase activity.

Preferably the isolated polynucleotide encodes a polypeptide comprising NodX (SEQ ID NO:9) or a functional variant or fragment thereof having oxygenase activity, preferably cytochrome P450 oxygenase activity.

Preferably the isolated polynucleotide encodes a polypeptide comprising NodM (SEQ ID NO:12) or a functional variant or fragment thereof having oxygenase activity, preferably FAD-dependent oxygenase activity.

Preferably the isolated polynucleotide encodes a polypeptide comprising NodB (SEQ ID NO:15) or a functional variant or fragment thereof having cyclase activity, preferably IDT cyclase activity.

Preferably the isolated polynucleotide encodes a polypeptide comprising NodO (SEQ ID NO:18) or a functional variant or fragment thereof having oxygenase activity, preferably FAD-dependent oxygenase activity.

Preferably the isolated polynucleotide encodes a polypeptide comprising NodJ (SEQ ID NO:21) or a functional variant or fragment thereof having oxygenase activity, preferably cytochrome P450 oxygenase activity.

Preferably the isolated polynucleotide encodes a polypeptide comprising NodC (SEQ ID NO:24) or a functional variant or fragment thereof having transferase activity, preferably GGT activity.

Preferably the isolated polynucleotide encodes a polypeptide comprising NodY1 (SEQ ID NO:27) or a functional variant or fragment thereof having oxygenase activity, preferably FAD-dependent oxygenase activity.

Preferably the isolated polynucleotide encodes a polypeptide comprising NodD2 (SEQ ID NO:30) or a functional variant or fragment thereof having transferase activity, preferably prenyl transferase activity.

Preferably the isolated polynucleotide encodes a polypeptide comprising NodD1 (SEQ ID NO:33) or a functional variant or fragment thereof having transferase activity, preferably prenyl transferase activity.

Preferably the isolated polynucleotide encodes a polypeptide comprising NodY2 (SEQ ID NO:36) or a functional variant or fragment thereof having oxygenase activity, preferably FAD-dependent oxygenase activity.

Preferably the isolated polynucleotide encodes a polypeptide comprising NodZ (SEQ ID NO:39) or a functional variant or fragment thereof having oxygenase activity, preferably cytochrome P450 oxygenase activity.

In one embodiment the isolated polynucleotide encodes a polypeptide comprising NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or a functional variant or fragment thereof.

In one embodiment the isolated polynucleotide encodes a polypeptide consisting essentially of NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or a functional variant or fragment thereof.

In one embodiment the isolated polynucleotide encodes a polypeptide consisting of NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or a functional variant or fragment thereof.

In another aspect the invention relates to an isolated polynucleotide comprising at least 70% nucleic acid sequence identity to a nucleic acid sequence selected from the group consisting of nodW cDNA (SEQ ID NO:2), nodW genomic DNA (SEQ ID NO:1), nodR cDNA (SEQ ID NO:5), nodR genomic DNA (SEQ ID NO:4), nodX cDNA (SEQ ID NO:8), nodX genomic DNA (SEQ ID NO:7), nodM cDNA (SEQ ID NO:11), nodM genomic DNA (SEQ ID NO:10), nodB cDNA (SEQ ID NO:14), nodB genomic DNA (SEQ ID NO:13), nodO cDNA (SEQ ID NO:17), nodO genomic DNA (SEQ ID NO:16), nodJ cDNA (SEQ ID NO:20), nodJ genomic DNA (SEQ ID NO:19), nodC cDNA (SEQ ID NO:23), nodC genomic DNA (SEQ ID NO:22), nodY1 cDNA (SEQ ID NO:26), nodY1 genomic DNA (SEQ ID NO:25), nodD2 cDNA (SEQ ID NO:29), nodD2 genomic DNA (SEQ ID NO:28), nodD1 cDNA (SEQ ID NO:32), nodD1 genomic DNA (SEQ ID NO:31), nodY2 cDNA (SEQ ID NO:35), nodY2 genomic DNA (SEQ ID NO:34), nodZ cDNA (SEQ ID NO:38), nodZ genomic DNA (SEQ ID NO:37), nodS cDNA (SEQ ID NO:49), nodS genomic DNA (SEQ ID NO:48), nodI cDNA (SEQ ID NO:55), and nodI genomic DNA (SEQ ID NO:54).

Preferably the isolated polynucleotide comprises at least 75%, preferably at least 80%, preferably at least 85%, preferably at least 90%, preferably at least 95%, preferably at least 99% nucleic acid sequence identity to a nucleic acid sequence selected from the group consisting of SEQ ID NO: nodW cDNA (SEQ ID NO:2), nodW genomic DNA (SEQ ID NO:1), nodR cDNA (SEQ ID NO:5), nodR genomic DNA (SEQ ID NO:4), nodX cDNA (SEQ ID NO:8), nodX genomic DNA (SEQ ID NO:7), nodM cDNA (SEQ ID NO:11), nodM genomic DNA (SEQ ID NO:10), nodB cDNA (SEQ ID NO:14), nodB genomic DNA (SEQ ID NO:13), nodO cDNA (SEQ ID NO:17), nodO genomic DNA (SEQ ID NO:16), nodJ cDNA (SEQ ID NO:20), nodJ genomic DNA (SEQ ID NO:19), nodC cDNA (SEQ ID NO:23), nodC genomic DNA (SEQ ID NO:22), nodY1 cDNA (SEQ ID NO:26), nodY1 genomic DNA (SEQ ID NO:25), nodD2 cDNA (SEQ ID NO:29), nodD2 genomic DNA (SEQ ID NO:28), nodD1 cDNA (SEQ ID NO:32), nodD1 genomic DNA (SEQ ID NO:31), nodY2 cDNA (SEQ ID NO:35), nodY2 genomic DNA (SEQ ID NO:34), nodZ cDNA (SEQ ID NO:38), nodZ genomic DNA (SEQ ID NO:37), nodS cDNA (SEQ ID NO:49), nodS genomic DNA (SEQ ID NO:48), nodI cDNA (SEQ ID NO:55), and nodI genomic DNA (SEQ ID NO:54).

In one embodiment the isolated polynucleotide comprises a nucleic acid sequence selected from the group consisting of nodW cDNA (SEQ ID NO:2), nodW genomic DNA (SEQ ID NO:1), nodR cDNA (SEQ ID NO:5), nodR genomic DNA (SEQ ID NO:4), nodX cDNA (SEQ ID NO:8), nodX genomic DNA (SEQ ID NO:7), nodM cDNA (SEQ ID NO:11), nodM genomic DNA (SEQ ID NO:10), nodB cDNA (SEQ ID NO:14), nodB genomic DNA (SEQ ID NO:13), nodO cDNA (SEQ ID NO:17), nodO genomic DNA (SEQ ID NO:16), nodJ cDNA (SEQ ID NO:20), nodJ genomic DNA (SEQ ID NO:19), nodC cDNA (SEQ ID NO:23), nodC genomic DNA (SEQ ID NO:22), nodY1 cDNA (SEQ ID NO:26), nodY1 genomic DNA (SEQ ID NO:25), nodD2 cDNA (SEQ ID NO:29), nodD2 genomic DNA (SEQ ID NO:28), nodD1 cDNA (SEQ ID NO:32), nodD1 genomic DNA (SEQ ID NO:31), nodY2 cDNA (SEQ ID NO:35), nodY2 genomic DNA (SEQ ID NO:34), nodZ cDNA (SEQ ID NO:38), nodZ genomic DNA (SEQ ID NO:37), nodS cDNA (SEQ ID NO:49), nodS genomic DNA (SEQ ID NO:48), nodI cDNA (SEQ ID NO:55), and nodI genomic DNA (SEQ ID NO:54).

In one embodiment the isolated polynucleotide consists essentially of a nucleic acid sequence selected from the group consisting of nodW cDNA (SEQ ID NO:2), nodW genomic DNA (SEQ ID NO:1), nodR cDNA (SEQ ID NO:5), nodR genomic DNA (SEQ ID NO:4), nodX cDNA (SEQ ID NO:8), nodX genomic DNA (SEQ ID NO:7), nodM cDNA (SEQ ID NO:11), nodM genomic DNA (SEQ ID NO:10), nodB cDNA (SEQ ID NO:14), nodB genomic DNA (SEQ ID NO:13), nodO cDNA (SEQ ID NO:17), nodO genomic DNA (SEQ ID NO:16), nodJ cDNA (SEQ ID NO:20), nodJ genomic DNA (SEQ ID NO:19), nodC cDNA (SEQ ID NO:23), nodC genomic DNA (SEQ ID NO:22), nodY1 cDNA (SEQ ID NO:26), nodY1 genomic DNA (SEQ ID NO:25), nodD2 cDNA (SEQ ID NO:29), nodD2 genomic DNA (SEQ ID NO:28), nodD1 cDNA (SEQ ID NO:32), nodD1 genomic DNA (SEQ ID NO:31), nodY2 cDNA (SEQ ID NO:35), nodY2 genomic DNA (SEQ ID NO:34), nodZ cDNA (SEQ ID NO:38), nodZ genomic DNA (SEQ ID NO:37), nodS cDNA (SEQ ID NO:49), nodS genomic DNA (SEQ ID NO:48), nodI cDNA (SEQ ID NO:55), and nodI genomic DNA (SEQ ID NO:54).

In one embodiment the isolated polynucleotide consists of a nucleic acid sequence selected from the group consisting of nodW cDNA (SEQ ID NO:2), nodW genomic DNA (SEQ ID NO:1), nodR cDNA (SEQ ID NO:5), nodR genomic DNA (SEQ ID NO:4), nodX cDNA (SEQ ID NO:8), nodX genomic DNA (SEQ ID NO:7), nodM cDNA (SEQ ID NO:11), nodM genomic DNA (SEQ ID NO:10), nodB cDNA (SEQ ID NO:14), nodB genomic DNA (SEQ ID NO:13), nodO cDNA (SEQ ID NO:17), nodO genomic DNA (SEQ ID NO:16), nodJ cDNA (SEQ ID NO:20), nodJ genomic DNA (SEQ ID NO:19), nodC cDNA (SEQ ID NO:23), nodC genomic DNA (SEQ ID NO:22), nodY1 cDNA (SEQ ID NO:26), nodY1 genomic DNA (SEQ ID NO:25), nodD2 cDNA (SEQ ID NO:29), nodD2 genomic DNA (SEQ ID NO:28), nodD1 cDNA (SEQ ID NO:32), nodD1 genomic DNA (SEQ ID NO:31), nodY2 cDNA (SEQ ID NO:35), nodY2 genomic DNA (SEQ ID NO:34), nodZ cDNA (SEQ ID NO:38), nodZ genomic DNA (SEQ ID NO:37), nodS cDNA (SEQ ID NO:49), nodS genomic DNA (SEQ ID NO:48), nodI cDNA (SEQ ID NO:55), and nodI genomic DNA (SEQ ID NO:54).

The nucleic acid molecules of the invention or otherwise described herein are preferably isolated. They can be isolated from a biological sample using a variety of techniques known to those of ordinary skill in the art. By way of example, such polynucleotides can be isolated through use of the polymerase chain reaction (PCR) as known in the art. The nucleic acid molecules of the invention can be amplified using primers, as defined herein, derived from the polynucleotide sequences of the invention.

Further methods for isolating polynucleotides include use of all, or portions of, a polynucleotide of the invention as hybridization probes. The technique of hybridizing labeled polynucleotide probes to polynucleotides immobilized on solid supports such as nitrocellulose filters or nylon membranes, can be used to screen genomic or cDNA libraries. Similarly, probes may be coupled to beads and hybridized to the target sequence. Isolation can be effected using known art protocols such as magnetic separation. The choice of appropriately stringent hybridization and wash conditions is believed to be within the skill of those in the art.

Polynucleotide fragments may be produced by techniques well-known in the art such as restriction endonuclease digestion and oligonucleotide synthesis.

A partial polynucleotide sequence may be used as a probe, in methods well-known in the art to identify the corresponding full length polynucleotide sequence in a sample. Such methods include PCR-based methods, 5'RACE and hybridization-based method, computer/database-based methods as known in the art. Detectable labels such as radioisotopes, fluorescent, chemiluminescent and bioluminescent labels may be used to facilitate detection. Inverse PCR also permits acquisition of unknown sequences, flanking the polynucleotide sequences disclosed herein, starting with primers based on a known region as known and used in the art. The method uses several restriction enzymes to generate a suitable fragment in the known region of a gene. The fragment is then circularized by intramolecular ligation and used as a PCR template. Divergent primers are designed from the known region. In order to physically assemble full-length clones, standard molecular biology approaches can be utilized as known in the art. Primers and primer pairs which allow amplification of polynucleotides of the invention, also form a further aspect of this invention.

Variants (including orthologues) may be identified by the methods described. Variant polynucleotides may be identified using PCR-based methods as known in the art. Typically, the polynucleotide sequence of a primer, useful to amplify variants of polynucleotide molecules by PCR, may be based on a sequence encoding a conserved region of the corresponding amino acid sequence.

Further methods for identifying variant polynucleotides include use of all, or portions of the specified polynucleotides as hybridization probes to screen genomic or cDNA libraries as described above. Typically probes based on a sequence encoding a conserved region of the corresponding amino acid sequence may be used. Hybridization conditions may also be less stringent than those used when screening for sequences identical to the probe.

In another aspect the invention relates to a TU comprising at least one isolated polynucleotide as described herein. In one embodiment the TU is comprised in vector, preferably an expression vector. In one embodiment the vector is selected from the group consisting of plasmids, BACs, (PACs), YACs, bacteriophage, phagemids, and cosmids. Preferably the vector is a plasmid.

In another aspect the invention relates to a vector that encodes an isolated polypeptide or functional variant or fragment thereof according to the invention.

In another aspect the invention relates to a vector comprising an isolated nucleic acid sequence according to the invention.

In one embodiment the isolated nucleic acid sequence is comprised in a TU.

In one embodiment the vector is selected from the group consisting of plasmids, BACs, PACs, YACs, bacteriophage, phagemids, and cosmids. Preferably the vector is a plasmid. In one embodiment the vector is an expression vector.

A TU comprising a polynucleotide of the invention can be incorporated into any suitable vector capable of expressing that polynucleotide or, where applicable, an encoded polypeptide of the invention in vitro or in a host cell. Preferably the vector is an expression vector. Examples of suitable expression vectors include, but not limited to, plasmid DNA vectors, viral DNA vectors (such as adenovirus and adeno-associated virus), or viral RNA vectors (such as a retroviral vectors). In some embodiments the plasmid and/or phage vectors may be selected from the following vectors or variants thereof including pUC18, pU19, Mp18, Mp19, ColE1, PCR1 and pKRC; lambda gt10 and M13 plasmids such as pBR322, pACYC184, pT127, RP4, p1J101, SV40 and BPV. Also included are vectors such as, but not limited to, cosmids, YACS, BACs shuttle vectors such as pSA3, PAT28 transposons (such as described in U.S. Pat. No. 5,792,294) and the like.

Suitable viral vectors include, but are not limited to vectors derived from adenovirus (AV); adeno-associated virus (AAV); retroviruses (e.g., lentiviruses (LV), Rhabdoviruses, murine leukemia virus); herpes virus, and the like. Viral vectors employed herein can be appropriately modified by pseudotyping with envelope proteins or other surface antigens from other viruses, or by substituting different viral capsid proteins, as known and used in the art.

In one embodiment the expression vector comprises at least one, preferably at least two, preferably at least three, preferably at least four, preferably at least five, preferably at least six, preferably at least seven, preferably at least eight, preferably at least nine, preferably at least 10 isolated polynucleotides as described herein.

In one embodiment the expression vector comprises at least one, preferably at least two, preferably at least three, preferably at least four, preferably at least five, preferably at least six, preferably at least seven, preferably at least eight, preferably at least nine, preferably at least 10 TUs as described herein.

In one embodiment the vector is a component in a cloning system. In one embodiment the cloning system is useful for making a gene construct comprising at least one TU.

In one embodiment the vector is comprised in a vector set, the vector set being part of a cloning system. In one embodiment the cloning system is useful for making a gene construct comprising at least one TU.

In one embodiment the cloning system is useful for making a gene construct comprising at least one TU.

In one embodiment the gene construct is a multigene construct comprising at least two TUs. In one embodiment the multigene construct comprises at least three, preferably at least four, preferably at least five, preferably at least six, preferably at least seven, preferably at least eight, preferably at least nine, preferably at least ten TUs.

The TUs described herein may comprise one or more of the disclosed polynucleotide sequences and/or polynucleotides encoding the disclosed polypeptides, of the invention. The TU can constructed to drive expression of at least one polypeptide involved in the biosynthesis of NAA 10, either in vitro or in vivo. In one embodiment, the TU comprises a polynucleotide of the invention operatively linked to 5' or 3' untranslated regulatory sequences. The design of a particular TU will depend on various factors including the host cells in which the operatively linked polynucleotide is to be expressed and the desired level of polynucleotide expression.

Likewise, the selection of various promoters, enhancers and/or other genetic elements for a TU will depend on various factors including the host cells and expression levels discussed above. In one embodiment, the TU comprises a homologous promoter operatively linked to a polynucleotide of the invention. In another embodiment, the expression cassette comprises a heterologous promoter operatively linked to a polynucleotide of the invention. In one embodiment, the homologous or heterologous promoter is an inducible, repressible or regulatable promoter. A suitable promoter may be chosen and used under the appropriate conditions to direct high-level expression of a polynucleotide of the invention. Many such elements are described in the literature and are available through commercial suppliers.

By way of example only, promoters useful in the expression cassettes can be any suitable eukaryotic or prokaryotic promoter. In one embodiment, the eukaryotic promoter can be a eukaryotic RNA polymerase I (pol I), RNA polymerase II (pol II), or RNA polymerase III (pol III). Expression levels of an operably linked polynucleotide in a particular cell type will be determined by the nearby presence (or absence) of specific gene regulatory sequences (e.g., enhancers, silencers and the like). Any suitable promoter/enhancer combination (see: Eukaryotic Promoter Data Base EPDB) can be used to drive expression of a polynucleotide of the invention.

Additional promoters useful in expression cassettes include ß-lactamase, alkaline phosphatase, tryptophan, and tac promoter systems which are all well known in the art. Yeast promoters include 3-phosphoglycerate kinase, enolase, hexokinase, pyruvate decarboxylase, glucokinase, and glyceraldehydrate-3-phosphanate dehydrogenase but are not limited thereto.

Prokaryotic promoters useful in expression cassettes include constitutive promoters as known in the art (such as the int promoter of bacteriophage lamda and the bla promoter of the beta-lactamase gene sequence of pBR322) and regulatable promoters (such as lacZ, recA and gal). A ribosome binding site upstream of the CDS may also be required for expression.

Enhancers useful in a TU include SV40 enhancer, cytomegalovirus early promoter enhancer, globin, albumin, insulin and the like.

In one embodiment, a TU may be driven by a T3, T7 or SP6 cytoplasmic expression system.

The choice of a particular promoter/enhancer/cell type combination for protein expression is within the ordinary skill of those in the art of molecular biology (see, for example, Sambrook et al. (1989) which is incorporated herein by reference).

In another aspect the invention relates to an isolated host cell comprising an isolated polypeptide, isolated polynucleotide, TU and/or isolated vector according to the invention.

In one embodiment the isolated host cell is a prokaryotic or eukaryotic cell. Prokaryotes most commonly employed as host cells are strains of *Escherichia coli* (*E. coli*). Other prokaryotic hosts include *Pseudomonas, Bacillus, Serratia, Klebsiella, Streptomyces, Listeria, Salmonella* and Mycobacteria but are not limited thereto.

In one embodiment the eukaryotic cell is an animal cell, a plant cell, a fungal cell or a protist cell. In one embodiment the animal cell is an insect cell or a mammalian cell. In one embodiment the fungal cell is a single cell of a unicellular fungal host strain. In one embodiment the fungal cell comprises fungal hyphae or the mycelia of a fungal host strain. In one embodiment the fungal cell, hyphae or mycelia of the fungal host strain are from the genus *Aspergillus, Trichoderma, Neurospora, Fusarium, Mortierella, Chrysosporium, Candida, Geotrichum, Yarrowia, Eremothecium, Trichoplusia, Ashbya, Hansenula, Pichia, Kluveromyces, Schizzosaccharomyces, Monascus, Talaromyces, Cryptonectria, Endothia, Tolypocladium, Hypocrea, Gibberella, Acremonium, Agaricus, Pleurotus, Penicillium, Volvariella, Flammulina, Lentinula, Auricularia, Ganoderma, (Rhizo)mucor, Riopus,* or *Saccharomyces*, preferably *Penicillium, Aspergillus, Saccharomyces, Pichia, Tricoplusia,* and *Spondoptera*. Preferably the fungal cell is from *Saccharomyces*. Preferably the fungal hyphae or mycelia is from *Penicillium*, preferably *P. paxilli*.

In another aspect the invention relates to a method of making at least one NA comprising heterologously expressing at least one polypeptide, isolated nucleic acid sequence, TU or vector according to the invention in an isolated host cell.

In one embodiment the NA is selected from the group of NAs depicted in FIG. 1. Preferably the NA is NAF 5a or NAA 10, preferably NAA 10.

In one embodiment the polypeptide is a polypeptide or functional variant or fragment according to the invention.

Specifically contemplated as embodiments within this aspect of the invention are various embodiments set out herein with regards to any other aspect of the invention that relate to heterologous expression (including choice of appropriate regulatory sequences), expression cassettes, genetic elements, TUs, multigene constructs, host cells, and vectors.

In a particular embodiment, heterologous expression of the polypeptide comprises expression of at least one polynucleotide according to the invention or at least one TU encoding at least one polypeptide of the invention, from at least one vector as described herein in an isolated fungal host cell or in the mycelia of an isolated fungal strain as described herein. In one embodiment the polypeptide is NodR (SEQ ID NO:6) NodX (SEQ ID NO:9), or NodZ (SEQ ID NO:39), preferably the polypeptide is an enzyme that catalyzes a biological transformation from NAB 9 to NAA 10. In one embodiment the fungal cell or strain is a cell or strain of *Penicillium*, preferably *P. paxilli*.

In one embodiment the TU is comprised in a multigene construct comprising at least two, at least three, at least four, at least five, at least six, at least seven, at least eight, at least nine and/or at least 10 polynucleotides encoding polypeptides according to the invention.

In another aspect the invention relates to at least one NA made by a method of the invention. In one embodiment the NA is selected from the group of NAs depicted in FIG. 1. Preferably the NA is NAF 5a or NAA 10, preferably NAA 10.

In another aspect the present invention relates to an isolated polypeptide or functional variant or fragment thereof from *Hypoxylon* spp. that catalyzes a biochemical reaction in the biosynthetic pathway leading from GGI 2 to NAA 10.

In another aspect the present invention relates to an isolated polynucleotide encoding at least one polypeptide from *Hypoxylon* spp. that catalyzes a biochemical reaction in the biosynthetic pathway leading from GGI 2 to NAA 10.

In one embodiment the isolated polypeptide is an oxygenase, preferably a cytochrome P450 oxygenase or a FAD-dependent oxygenase. Preferably the cytochrome P450 oxygenase is NodW (SEQ ID NO:3), NodR (SEQ ID NO:6), NodX (SEQ ID NO:9), NodJ (SEQ ID NO:21), or NodZ (SEQ ID NO:39). Preferably the FAD dependent oxygenase is NodM (SEQ ID NO:12), NodO (SEQ ID NO:18), NodY1 (SEQ ID NO:27), or NodY2 (SEQ ID NO:36). In one embodiment the isolated polypeptide is a transferase, preferably a GGT, or a prenyl transferase. Preferably the GGT is NodC (SEQ ID NO:24). Preferably the prenyl transferases are NodD1 (SEQ ID NO:33), or NodD2 (SEQ ID NO:30). In one embodiment the isolated polypeptide is a IDT cyclase. Preferably the IDT cyclase is NodB (SEQ ID NO: 15). In one embodiment the isolated polypeptide is NodS (SEQ ID NO:50). In one embodiment the isolated polypeptide is NodI (SEQ ID NO:56).

In one embodiment the isolated polypeptide catalyzes a biochemical reaction in the biosynthetic pathway leading from GGI 2 to NAF 5a. Preferably the isolated polypeptide is a GGT, a FAD-dependent oxygenase, an IDT cyclase, or a cytochrome P450 oxygenase. Preferably the GGT is NodC (SEQ ID NO:24). Preferably the FAD-dependent oxygenase is NodM (SEQ ID NO:12). Preferably the IDT cyclase is NodB (SEQ ID NO:15). Preferably the cytochrome P450 oxygenase is NodW (SEQ ID NO:3).

In one embodiment the isolated polypeptide or functional variant or fragment thereof is encoded by a nucleic acid according to the invention.

In another aspect the invention relates to a method of making at least one *Hypoxylon* spp. polypeptide or functional variant or fragment thereof comprising heterologously expressing an isolated nucleic acid sequence, TU or vector according to the invention in an isolated host cell.

In one embodiment the at least one *Hypoxylon* spp. polypeptide is a polypeptide according to the invention as contemplated herein for any other aspect of the invention.

In one embodiment the at least one *Hypoxylon* spp. polypeptide is a polypeptide comprising an amino acid sequence of SEQ ID NO: NodW (SEQ ID NO:3) or a functional variant or fragment thereof. Preferably the polypeptide consists essentially or consists of SEQ ID NO: NodW (SEQ ID NO:3). In one embodiment the isolated host cell comprises fungal mycelia of the genus *Penicillium*, preferably *P. paxilli*.

Specifically contemplated for this aspect of the invention are various embodiments set out for any other aspect of the invention that relate to the heterologous expression (including choice of appropriate regulatory sequences), genetic elements, TUs, multigene constructs, host cells, and vectors.

In another aspect the invention relates to a method of making at least one NA comprising heterologously expressing in an isolated host cell, at least one polypeptide that catalyzes a biochemical reaction in the biosynthetic pathway leading from GGI 2 to NAA 10.

In one embodiment the at least one polypeptide is an oxygenase, preferably a cytochrome P450 oxygenase or a FAD-dependent oxygenase. Preferably the cytochrome P450 oxygenase is NodW (SEQ ID NO:3), NodR (SEQ ID NO:6), NodX (SEQ ID NO:9), NodJ (SEQ ID NO:21), or NodZ (SEQ ID NO:39). Preferably the FAD dependent oxygenase is NodM (SEQ ID NO: 12), NodO (SEQ ID NO:18), NodY1 (SEQ ID NO:27), or NodY2 (SEQ ID NO:36). In one embodiment the isolated polypeptide is a transferase, preferably a GGT, or a prenyl transferase. Preferably the GGT is NodC (SEQ ID NO:24). Preferably the prenyl transferases are NodD1 (SEQ ID NO:33), or NodD2 (SEQ ID NO:30). In one embodiment the isolated polypeptide is a IDT cyclase. Preferably the IDT cyclase is NodB (SEQ ID NO:15). In one embodiment the isolated polypeptide is NodS (SEQ ID NO:50). In one embodiment the isolated polypeptide is NodI (SEQ ID NO:56).

In one embodiment the at least one polypeptide catalyzes a biochemical reaction in the biosynthetic pathway leading from GGI 2 to NAF 5a. Preferably at least one polypeptide is a GGT, a FAD-dependent oxygenase, an IDT cyclase, or a cytochrome P450 oxygenase. Preferably the GGT is NodC (SEQ ID NO:24). Preferably the FAD-dependent oxygenase is NodM (SEQ ID NO:12). Preferably the IDT cyclase is NodB (SEQ ID NO:15). Preferably the cytochrome P450 oxygenase is NodW (SEQ ID NO:3).

In one embodiment the least one polypeptide comprises the amino acid sequence of SEQ ID NO: NodW (SEQ ID NO:3) or a functional variant or fragment thereof. Preferably the polypeptide consists essentially or consists of SEQ ID NO: NodW (SEQ ID NO:3). In one embodiment the isolated host cell comprises fungal mycelia of the genus *Penicillium*, preferably *P. paxilli*.

Specifically contemplated for this aspect of the invention are various embodiments set out for any other aspect of the invention that relate to the heterologous expression (including choice of appropriate regulatory sequences), genetic elements, TUs, multigene constructs, host cells, and vectors.

In another aspect the invention relates to an isolated host cell that expresses at least one heterologous polypeptide that catalyzes the transformation of a substrate in the biosynthetic pathway leading to the formation of NAA 10.

In one embodiment at least one heterologous polypeptide catalyzes the transformation of a substrate in the biosynthetic pathway leading to the formation of NAF 5a.

In one embodiment the substrate is selected from the group consisting of GGPP 1a, indole-3-glycerol phosphate 1b, GGI 2, mono-epoxidized GGI 3a, emindole SB 4a, NAF 5a, NAE 6a, NAD 7a, NAC 8, and NAB 9.

In one embodiment the transformation is selected from the group consisting of a condensation, an oxidation, or a cyclization.

In one embodiment the substrates that are transformed are GGPP 1a and indole-3-glycerol phosphate 1b, and the transformation is a condensation.

In one embodiment the substrate that is transformed is GGI 2 and the transformation is an oxidation.

In one embodiment the substrate that is transformed is mono-epoxidized GGI 3a and the transformation is a cyclization.

In one embodiment the substrate that is transformed is emindole SB 4a and the transformation is an oxidation.

In one embodiment the substrate that is transformed is NAF 5a and the transformation is a condensation.

In one embodiment the substrate that is transformed is NAE 6a and the transformation is an oxidation.

In one embodiment the substrate that is transformed is NAD 7a and the transformations are an oxidation and a condensation.

In one embodiment the substrate that is transformed is NAC 8 and the transformation is an oxidation.

In one embodiment the substrate that is transformed is NAB 9 and the transformation is an oxidation.

In another aspect the invention relates to an isolated host cell that produces, by heterologous expression, at least one polypeptide involved in the biosynthetic pathway leading to NAA 10.

In one embodiment the at least one polypeptide catalyzes a biochemical reaction in the biosynthetic pathway leading from GGI 2 to NAF 5a. Preferably at least one polypeptide is a GGT, a FAD-dependent oxygenase, an IDT cyclase, or a cytochrome P450 oxygenase. Preferably the GGT is NodC (SEQ ID NO:24). Preferably the FAD-dependent oxygenase is NodM (SEQ ID NO:12). Preferably the IDT cyclase is NodB (SEQ ID NO: 15). Preferably the cytochrome P450 oxygenase is NodW (SEQ ID NO:3).

In some embodiments specifically contemplated for this aspect of the invention, the at least one polypeptide is a polypeptide involved in the biosynthetic pathway leading to NAA 10 as defined herein for any other aspect of the invention.

In one embodiment at least one polypeptide is a polypeptide or functional variant or fragment thereof of the invention. In one embodiment the polypeptide or functional variant or fragment thereof is encoded by a nucleic acid sequence of the invention.

In one embodiment the at least one polypeptide is involved in the biosynthetic pathway leading to NAF 5a. In one embodiment the least one polypeptide comprises the amino acid sequence of SEQ ID NO: NodW (SEQ ID NO:3) or a functional variant or fragment thereof. Preferably the polypeptide consists essentially or consists of SEQ ID NO: NodW (SEQ ID NO:3). In one embodiment the isolated host cell comprises fungal mycelia of the genus *Penicillium*, preferably *P. paxilli*.

Specifically contemplated for this aspect of the invention are various embodiments set out for any other aspect of the invention that relate to the heterologous expression (including choice of appropriate regulatory sequences), genetic elements, TUs, multigene constructs, host cells, and vectors.

In another aspect the invention relates to a method of producing at least one NA comprising contacting a carbohydrate comprising substrate with a recombinant cell transformed with a nucleic acid that results in an increased level or activity of a polypeptide selected from the group consisting of NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or a functional variant or fragment thereof compared to the cell prior to transformation, such that the substrate is metabolized to at least one NA.

In one embodiment the nucleic acid encodes at least one polypeptide that catalyzes a biochemical reaction in the biosynthetic pathway leading from GGI 2 to NAF 5a, preferably that catalyzes the biochemical reaction that leads from emindole SB 4a to NAF 5a.

In one embodiment the recombinant host cell is an isolated host cell of the invention as described herein.

In one embodiment the carbohydrate is comprised in a culture media. In one embodiment the culture media is CDYE or a variation thereof that supports the growth of the recombinant cell.

In one embodiment the nucleic acid encodes least one polypeptide that is an oxygenase, preferably a cytochrome P450 oxygenase or a FAD-dependent oxygenase. Preferably the cytochrome P450 oxygenase is NodW (SEQ ID NO:3), NodR (SEQ ID NO:6), NodX (SEQ ID NO:9), NodJ (SEQ ID NO:21), or NodZ (SEQ ID NO:39). Preferably the FAD dependent oxygenase is NodM (SEQ ID NO:12), NodO (SEQ ID NO:18), NodY1 (SEQ ID NO:27), or NodY2 (SEQ ID NO:36). In one embodiment the isolated polypeptide is a transferase, preferably a GGT, or a prenyl transferase. Preferably the GGT is NodC (SEQ ID NO:24). Preferably the prenyl transferases are NodD1 (SEQ ID NO:33), or NodD2 (SEQ ID NO:30). In one embodiment the isolated polypeptide is a IDT cyclase. Preferably the IDT cyclase is NodB (SEQ ID NO: 15). In one embodiment the isolated polypeptide is NodS (SEQ ID NO:50). In one embodiment the isolated polypeptide is NodI (SEQ ID NO:56).

In one embodiment the nucleic acid encodes at least one GGT, FAD-dependent oxygenase, IDT cyclase, or cytochrome P450 oxygenase. In one embodiment the nucleic acid codes at least two, preferably at least three, preferably all four of the GGT, FAD-dependent oxygenase, IDT cyclase, or cytochrome P450 oxygenase. Preferably the GGT is NodC (SEQ ID NO:24). Preferably the FAD-dependent oxygenase is NodM (SEQ ID NO:12). Preferably the IDT cyclase is NodB (SEQ ID NO:15). Preferably the cytochrome P450 oxygenase is NodW (SEQ ID NO:3).

In one embodiment a polypeptide selected from the group consisting of NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or a functional variant or fragment thereof comprises the amino acid sequence of a NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or functional variant or fragment thereof of the invention.

In one embodiment the polypeptide comprises the amino acid sequence of NodW (SEQ ID NO:3) or a functional variant or fragment thereof. Preferably the polypeptide consists essentially or consists of SEQ ID NO: NodW (SEQ ID NO:3). In one embodiment the isolated host cell comprises fungal mycelia of the genus Penicillium, preferably P. paxilli.

Specifically contemplated for this aspect of the invention are various embodiments set out for any other aspect of the invention that relate to the heterologous expression (including choice of appropriate regulatory sequences), genetic elements, TUs, multigene constructs, host cells, and vectors.

In one embodiment the at least one heterologous or introduced homologous nucleic acid sequence is at least one NAA 10 biosynthetic gene selected from the group consisting of nodW, nodR, nodX, nodM, nodB, nodO, nodJ, nodC, nodY1, nodD2, nodD1, nodY2, nodZ nodS, and nodI as described herein.

In one embodiment one of the two different GGPPS enzymes is produced in H. pulicicidum by heterologous expression.

In one embodiment one of the two different GGPPS enzymes is encoded by a second copy of a native H. pulicicidum gene that encodes a GGPPS enzyme.

In another aspect the invention relates to an isolated strain of Hypoxylon pulicicidum that comprises a genetic modification that leads to an increased biosynthesis of NAA 10.

In one embodiment the isolated strain comprises increased expression of at least one GGPPS enzyme as compared to a control strain of *H. pulicicidum*, preferably *H. pulicicidum* ATCC 74245.

In one embodiment the increased expression is increased expression of the native primary GGPPS gene of *H. pulicicidum* via modification of genetic regulatory elements.

In one embodiment modification of genetic regulatory elements comprises operatively linking the native primary GGPPS gene to an alternative or modified promoter.

In one embodiment modification of genetic regulatory elements comprises operatively linking a native primary GGPPS gene to a more robust native promoter. In one embodiment the native primary GGPPS gene is an introduced homologous gene.

In one embodiment the increased expression is the result of heterologous expression of biosynthetic genes that contribute to NAA 10 biosynthesis.

In one embodiment the increased expression is due to expression of heterologous genes in *H. pulicicidum* that have equivalent biochemical function to genes identified in the Nod cluster, wherein the Nod cluster is as described herein.

In one embodiment the increased expression is due to expression of heterologous genes in *H. pulicicidum* to remediate limitations in the supply of substrate compounds or biosynthetic intermediates that are necessary for NAA 10 biosynthesis.

In one embodiment the increased expression is due to heterologous expression in *H. pulicicidum* of any gene that encodes a GGT that catalyzes the condensation of GGPP 1a and indole-3-glycerol phosphate 1b to produce 3-geranylgeranyl indole 2.

In one embodiment the increased expression is due to heterologous expression in *H. pulicicidum* of any gene that encodes a GGPPS.

In one embodiment the increased expression is due to heterologous expression in *H. pulicicidum* of any gene that encodes a FAD-dependent oxidase that creates the single epoxidized-GGI product 3a.

In one embodiment the increased expression is due to heterologous expression in *H. pulicicidum* of any gene that encodes an enzyme that cyclises the single epoxidized-GGI 3a to produce emindole SB 4a.

In one embodiment the increased expression is due to heterologous expression in *H. pulicicidum* of any gene that encodes an oxidase that oxidises emindole SB 4a to produce a nodulisporic acid.

In one embodiment the increased expression is due to at least one genetic modification that leads to the increased expression of a NA biosynthetic gene selected from the group consisting of nodW, nodR, nodX, nodM, nodB, nodO, nodJ, nodC, nodY1, nodD2, nodD1, nodY2, nodZ, nods and nodI as described herein.

In another aspect the invention relates to a method of making NAA 10 comprising expressing at least one heterologous nucleic acid sequence in *Hypoxylon pulicicidum*, wherein the at least one heterologous nucleic acid sequence encodes an enzyme in a biosynthetic pathway leading to NAA 10.

Figure 11:
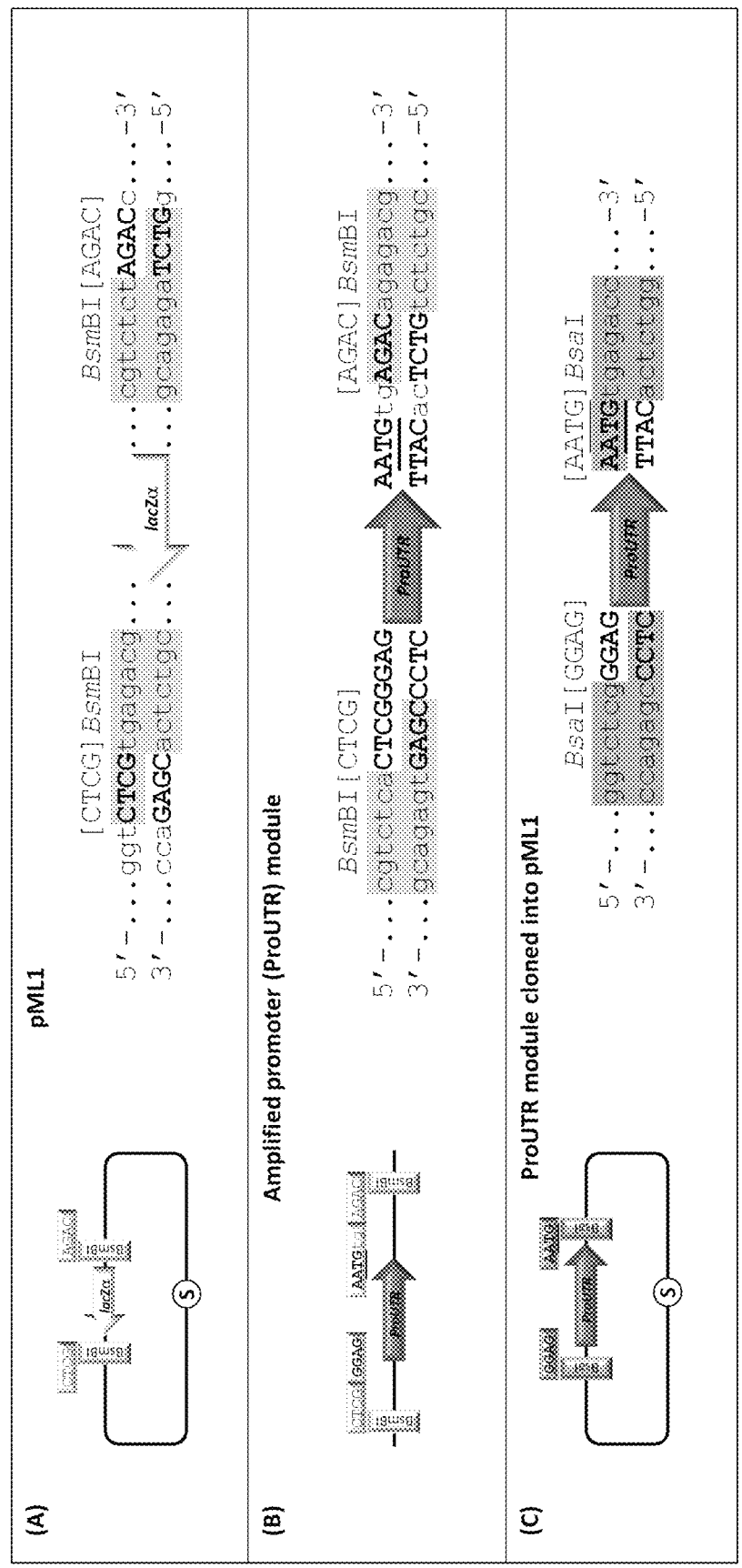
FIG. 11: Overview of MIDAS Level-1 cloning. (A) ggtctcgtgagacg (SEQ ID NO: 125); cgtctctagacc (SEQ ID NO: 126); ccagagcactctgc (SEQ ID NO: 127); gcagagatctgg (SEQ ID NO: 128); (B) cgtctcactcgggag (SEQ ID NO: 129); aatgtgagacagagacg (SEQ ID NO: 130); gcagagtgagccctc (SEQ ID NO: 131); ttacactctgtctctgc (SEQ ID NO: 132); (C) ggtctcgggag (SEQ ID NO: 133); aatgtgagacc (SEQ ID NO: 134); ccagagccctc (SEQ ID NO: 135); ttacactctgg (SEQ ID NO: 136).

Specifically contemplated for this aspect of the invention are various embodiments set out for any other aspect of the invention that relate to the isolated strains of *Hypoxylon pulicicidum* as described herein including as relates to increased expression of NAA 10, and also including all embodiments set out regarding heterologous expression (including choice of appropriate regulatory sequences), genetic elements, TUs, multigene constructs, host cells, and vectors as described herein.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents; or such sources of information, in any jurisdiction, are prior art, or form part of the common general knowledge in the art.

The invention will now be illustrated in a non-limiting way by reference to the following examples.

EXAMPLES

Materials and Methods gDNA Isolation for Genome Sequencing and TUM Amplification

Genomic DNA for genome sequencing and TUM amplification by PCR was isolated from *Penicillium paxilli* strain ATCC® 26601™ (PN2013) and *Hypoxylon pulicicidum* strain ATCC® 74245™, according to Byrd, A. D.; Schardl, C. L.; Songlin, P. J.; Mogen, K. L.; Siegel, M. R. Curr. Genct. 1990, 18 (4), 347-354. with modifications. Sterile 2.4% (w/v) Difco™ potato dextrose broth (Becton, Dickinson and Company, Maryland, U.S.A.) in Milli-Q® water was prepared in 25 mL aliquots in 125 mL Erlenmeyer flasks and inoculated with $5\times10^6$ spores or ~1 $cm^2$ freshly ground mycelia (for non-sporulating strains). Cultures were incubated for 2-4 days at 22° C. with shaking (200 rpm). The fermentation broth was filtered through a sterile nappy liner and the mycelia were rinsed three times with sterile water. Mycelia was transferred to a sterile 15 mL centrifuge tube and flash frozen in liquid nitrogen for lyophilization for 24-48 hours. 15-20 mg freeze dried mycelia was placed in a mortar with liquid nitrogen and ground into a powder. The ground mycelia was transferred into a 2 mL tube and resuspended in 1 mL extraction buffer (150 mM EDTA, 50 mM Tris-HCl, and 1% (w/v) sodium lauroyl sarcosine). 1.6 mg proteinase K was added to the tube and contents were incubated at 37° C for 30 min. The tube was centrifuged at 13,000 rpm for 10 min and the supernatant was transferred to a fresh 2 mL tube. 500 μL phenol and 500 μL chloroform were added to the tube and the contents were mixed by vortex before centrifugation for 10 min at 13,000 rpm. The aqueous phase was transferred to a fresh 2 mL tube and washed two more times with 500 μL phenol and 500 μL chloroform as previously described. The aqueous phase was then transferred to a fresh 2 mL tube and washed (vortex and centrifuge at 13,000 rpm for 10 min) with 1 mL chloroform. The aqueous phase was transferred to a fresh 2 mL tube and mixed with 1 mL chilled isopropanol. The DNA was precipitated overnight at −20° C. and pelleted at 13,000 rpm for 10 min. The supernatant was discarded and the DNA was resuspended in 1 mL 1 M NaCl. The tube was incubated for 10 min at room temperature and then centrifuged at 13,000 rpm for 10 min to pellet polysaccharides. The supernatant was transferred to a fresh tube and mixed with 1 mL isopropanol. The tube was incubated at room temperature for 10 min and DNA was pelleted by centrifugation at 13,000 rpm for 10 min. The supernatant was discarded and 1 mL chilled 70% ethanol was added to the pellet without resuspension. The tube was centrifuged for 2 min at 13,000 rpm and the supernatant was discarded. The tube was centrifuged for 1 min at 13,000 rpm and residual 70% ethanol was pipette off. The pellet was air dried at room temperature, resuspended in 50 μL Milli-Q® water and stored at −20° C.

MIDAS Design Overview

The MIDAS toolkit is based on the Golden Gate assembly technique, which utilises the ability of Type IIS restriction enzymes to seamlessly join multiple DNA fragments together in a single reaction. MIDAS makes use of three Type IIS restriction enzymes, AarI, BsaI and BsmBI, which generate user-defined 4 bp overhangs upon cleavage. Through the appropriate choice of these user-defined overhangs, and the appropriate orientation of the Type IIS sites flanking each of the DNA fragments, multiple fragments can be assembled into a recipient plasmid (also called a destination vector) in an ordered (directional) fashion using a one-pot restriction-ligation reaction. The recipient plasmid contains a marker gene (typically the lacZα gene for blue/white screening) flanked by two divergently oriented recognition sites for a Type IIS enzyme; these elements, collectively called the 'Golden Gate cloning cassette', are replaced by the insert during the assembly reaction.

As with other recently described Golden Gate-based modular assembly techniques, assembly of genes and multigene constructs using MIDAS is a hierarchical process. At the first level (MIDAS Level-1), functional modules (promoters, CDS, terminators, tags, etc.) are cloned into the Level-1 destination vector (pML1), where they form libraries of reusable, sequence-verified parts. The complementary design of the modules and destination vector ensures that, once cloned into pML1, these modules can be released from the vector by digestion with BsaI.

At the second level (Level-2), compatible sets of the sequence-verified Level-1 modules are released from pML1 and assembled into a Level-2 destination vector (pML2) using a BsaI-mediated Golden Gate reaction, leading to creation of a Level-2 plasmid containing a eukaryotic TU. Once again, the design rules ensure that each assembled TU can be released from the pML2 vector—this time by digestion either with AarI or BsmBI (depending on the pML2 vector in which the TU was assembled).

At Level-3, the TUs that were assembled at Level-2 are released from the pML2 plasmids and are sequentially assembled together in a Level-3 destination vector (pML3), using either AarI- or BsmBI-mediated Golden Gate reactions, to form functional multigene constructs, which can then be transformed into the desired expression host.

Level-1: Module Cloning

At Level-1, functional TUMs are generated, either as a PCR product, or as a synthetic polynucleotide sequence (from a gene synthesis company), and are cloned into the Level-1 destination vector (pML1) by BsmBI-mediated Golden Gate cloning. In order to be cloned into the pML1 vector, the PCR primers are designed so that each amplified TUM is flanked by two convergent BsmBI sites, BsmBI [CTCG] and [AGAC]BsmBI, which upon restriction enzyme cleavage, generate sticky ends that are compatible with those of the BsmBI sites present in the pML1 destination vector. Thus, the Golden Gate cloning cassette present in pML1 consists of two divergent BsmBI sites flanking a lacZα scoreable marker: 5'-[CTCG]BsmBI-lacZα-BsmBI [AGAC]-3' (FIG. 11A).

To enable subsequent (i.e., Level-2) assembly of full-length TUs, each TUM is designed to be flanked by four module-specific nucleotides (NNNN) at the 5' end, and four module-specific nucleotides (NNNN) at the 3' end, which are included as part of the PCR primer sequences. The complementary design of the amplified modules and the pML1 vector ensures that, when amplified TUMs are cloned into pML1 using the BsmBI-mediated Golden Gate reaction, each TUM becomes flanked by convergent BsaI recognition sites, and the module-specific nucleotides (NNNN and NNNN) become the BsaI-specific 4 bp overhangs when the module is released from pML1 during the subsequent (i.e., Level-2) BsaI-mediated Golden Gate assembly of the full-length TU. Thus, the overall structure of each module in the PCR product (or synthetic polynucleotide) takes the form: 5'-BsmBI[CTCG]NNNN-TUM-NNNNtg[AGAC]BsmBI-3' (FIG. 11B), which becomes 5'-BsaI[NNNN]-TUM-[NNNN]BsaI-3' in pML1, following BsmBI-mediated cloning (FIG. 11C).

Figure 12:
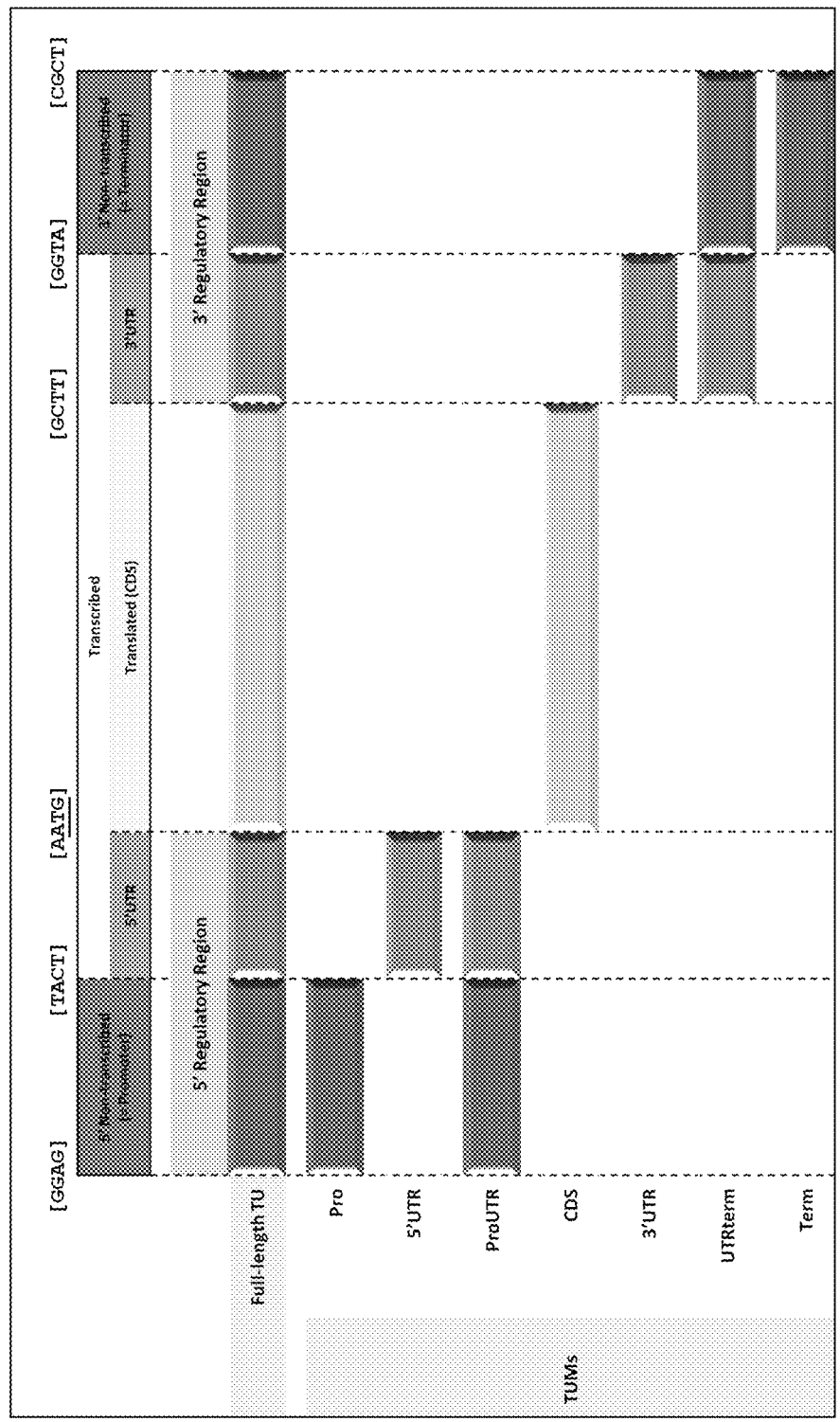
FIG. 12: MIDAS module address system.

As each TUM is defined by its flanking four nucleotides, these module-specific bases effectively form an address system for each TUM and they determine its position and orientation within the assembled TU. The developers of MoClo and GoldenBraid2.0 have already worked in concert to develop a common syntax or set of standard addresses for plant expression (referred to as 'fusion sites' in the MoClo system and 'barcodes' in GoldenBraid2.0) for a wide variety of TUMs to facilitate part exchangeability, and this standard is also adopted here for MIDAS-based assembly of TUs for expression in filamentous fungi (FIG. 12).

Thus, for filamentous fungal expression, a ProUTR module (comprising a promoter, 5' untranslated region (UTR) and ATG initiation codon) would have GGAG as the module-specific 5' nucleotides, and AATG as the module-specific 3' nucleotides (i.e., 5'-GGAG-ProUTR-AATG-3'), with the translation initiation codon underlined. Similarly, a CDS module would be flanked by AATG and GCTT (i.e., 5'-AATG-CDS-GCTT-3'), while a UTRterm module (consisting of a 3'UTR and a 3' non-transcribed region, including the polyadenylation signal) would have the form 5'-GCTT-UTRterm-CGCT-3'. Considerations for the design of PCR primers for amplifying these three types of TUM are shown in Table 12.

Following the BsmBI-mediated assembly of TUMs in pML1, reactions are transformed into an *E. coli* strain such as DH5α (or equivalent) and spread onto LB plates supplemented with spectinomycin, IPTG and X-Gal. Plasmids harbouring a cloned TUM are identified by screening white colonies and confirmed by sequencing.

At MIDAS Level-1, it is important that all internal recognition sites for AarI, BsaI and BsmBI are masked or eliminated from the TUMs. The process of masking or removal of such forbidden sites—referred to as "domestication"—can be achieved by; (i) excluding these sites when ordering the sequences from a gene synthesis company, (ii) directed mutagenesis, or (iii) using masking oligonucleotides that form triplexes with the target DNA, thereby preventing restriction enzyme cleavage. In the same way that Type IIS enzymes have previously been utilised for mutagenesis and for Golden Gate domestication purposes, we domesticated MIDAS modules by designing PCR primers (referred to as domestication primers) that overlap the internal Type IIS restriction site and which contain a single nucleotide mismatch that destroys the site. Because the PCR products are designed to be assembled together in MIDAS using a BsmBI-mediated Golden Gate reaction to form the full-length domesticated TUM in pML1, it is important that the MIDAS domestication primers be designed with BsmBI restriction sites that generate compatible overhangs at their 5' ends.

Level-2: TU Assembly

At Level-2, compatible sets of cloned and sequence-verified Level-1 TUMs (for example ProUTR, CDS and UTRterm modules) are assembled into a pML2 destination vector using a BsaI-mediated Golden Gate reaction, leading to creation of a Level-2 plasmid (pML2 entry clone) containing a complete (i.e., full-length) eukaryotic TU. The module address standard described earlier ensures that the assembly of a TU proceeds in an ordered, directional fashion, with the 3' end of one module being compatible with the 5' end of the next module.

The module-specific bases GGAG, located at the 5' end of ProUTR modules, and CGCT, at the 3' end of UTRterm modules, are compatible with the overhangs generated by BsaI digestion of the pML2 destination vectors, and these bases therefore define the outermost cloning boundaries of a Level-2 assembly.

In MIDAS, there are eight Level-2 (pML2) destination vectors into which a TU can be assembled, the choice of which depends on the desired configuration of TUs in the multigene plasmid produced at Level-3, namely: (i) the desired order in which TUs are added to the multigene assembly, (ii) the desired direction in which the multigene plasmid is assembled and (iii) the desired orientation of each TU in the multigene plasmid. These features are discussed further below.

The pML2 vectors are distinguished from one another by the arrangement of specific sequence features that are central to the operation of MIDAS. These sequence features, collectively called the MIDAS cassette (FIG. 13), define the Level-2 assembly of TUs and govern the assembly of multigene constructs produced at Level-3.

Each MIDAS cassette is defined by (i) having a Golden Gate cloning cassette with flanking, divergent BsaI recognition sites, (ii) differing arrangements of recognition sites for AarI and BsmBI and (iii) the presence or absence of a lacZα scoreable marker. These features are described in greater detail.

In contrast to the usual Golden Gate cloning cassette (which typically contains a lacZα gene for blue/white screening), the Golden Gate cloning cassettes in all eight pML2 vectors contain a mutant *E. coli* pheS gene (driven by the promoter of the *E. coli* gene for chloramphenicol acetyl-transferase) flanked by divergent BsaI recognition sites. The Thr$^{251}$Ala/Ala$^{294}$Gly double mutant of the *E. coli* pheS gene used here confers high lethality to cells grown on LB media supplemented with the phenylalanine analogue 4-chlorophenylalanine, 4CP.[36] During BsaI-mediated Level-2 assembly of TUs, the mutant pheS gene is eliminated from the pML2 vectors and can therefore be used as a negative selection marker.

Figure 13:
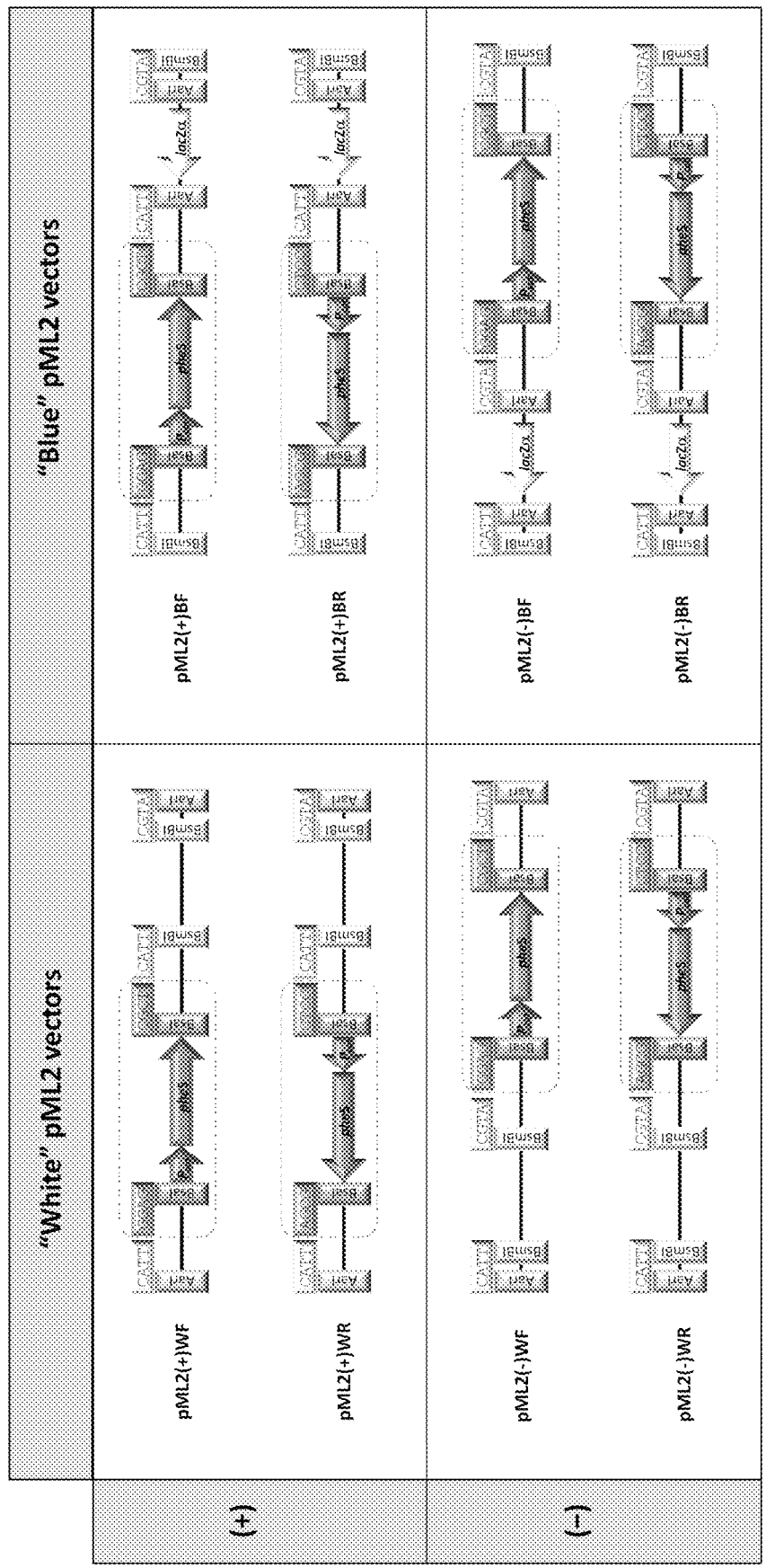
FIG. 13: Overview of MIDAS cassettes.

The eight pML2 vectors can be divided into two classes, "Blue" and "White", depending on the presence or absence, respectively, of a lacZα gene in the MIDAS cassette (see FIG. 13). There are four "Blue" pML2 vectors (indicated by the "B" in the plasmid name) and four "White" pML2 vectors (indicated by the "W" in the plasmid name). The "Blue" and "White" vectors also differ in the relative configuration of the AarI and BsmBI restriction sites in their MIDAS cassettes. Thus, in the "Blue" vectors, the entire MIDAS cassette is flanked by convergent BsmBI sites and nested within is the lacZα gene flanked by divergent AarI sites. In the "White" vectors, the enzyme configuration is switched (the entire MIDAS cassette is flanked by convergent AarI sites and nested within are two divergent BsmBI sites) and there is no lacZα gene. It is important to note that the lacZα chromogenic marker in the pML2 vectors is not used for blue/white screening during the Level-2 Golden Gate assembly of TUs (it is reserved for the Level-3 cloning), but the choice of "Blue" or "White" vector into which a TU should be assembled must be made during Level-2 assembly of TUs as this will determine the order in which that TU is added to the multigene construct at Level-3. Likewise, the AarI and BsmBI sites are also not used for Level-2 assembly of TUs; instead they are integral to the Level-3 assembly of multigene constructs. These considerations, including the differences between the (+) and (−) vectors, are discussed further below, under the Level-3 description.

The orientation (direction of transcription) of each TU can be freely defined by assembling each TU in either a pML2 "Forward" vector (indicated by "F" in the plasmid name) or a pML2 "Reverse" vector (indicated by "R" in the plasmid name). The pML2 "Reverse" vectors have their BsaI recognition sites (for Golden Gate assembly of TUs) switched relative to the BsaI fusion sites in the pML2 "Forward" vectors. Thus, pML2 "Forward" vectors have their pheS-based Golden Gate cassette oriented 5'-[GGAG]BsaI-pheS ▶-BsaI[CGCT]-3', while the pML2 "Reverse" vectors have their BsaI recognition sites switched: 5'-[AGCG]BsaI-◀ pheS-BsaI[CTCC]-3', where the arrowhead indicates the direction of transcription of the mutant pheS gene.

In contrast to the cloned Level-1 modules, the pML2 destination vectors confer kanamycin resistance, allowing efficient counter selection against Level-1 module backbones, while the mutant pheS gene provides powerful negative selection against any parental pML2 destination plasmids when *E. coli* DH5α cells (or equivalent) transformed with the assembly reactions are spread onto LB plates supplemented with kanamycin and 4CP.

Level-3: Assembly of Multigene Constructs

At MIDAS Level-3, TUs that were assembled in the pML2 plasmids are sequentially loaded (by binary assembly) into the Level-3 destination vector (pML3) to form the multigene construct.

Figure 14:
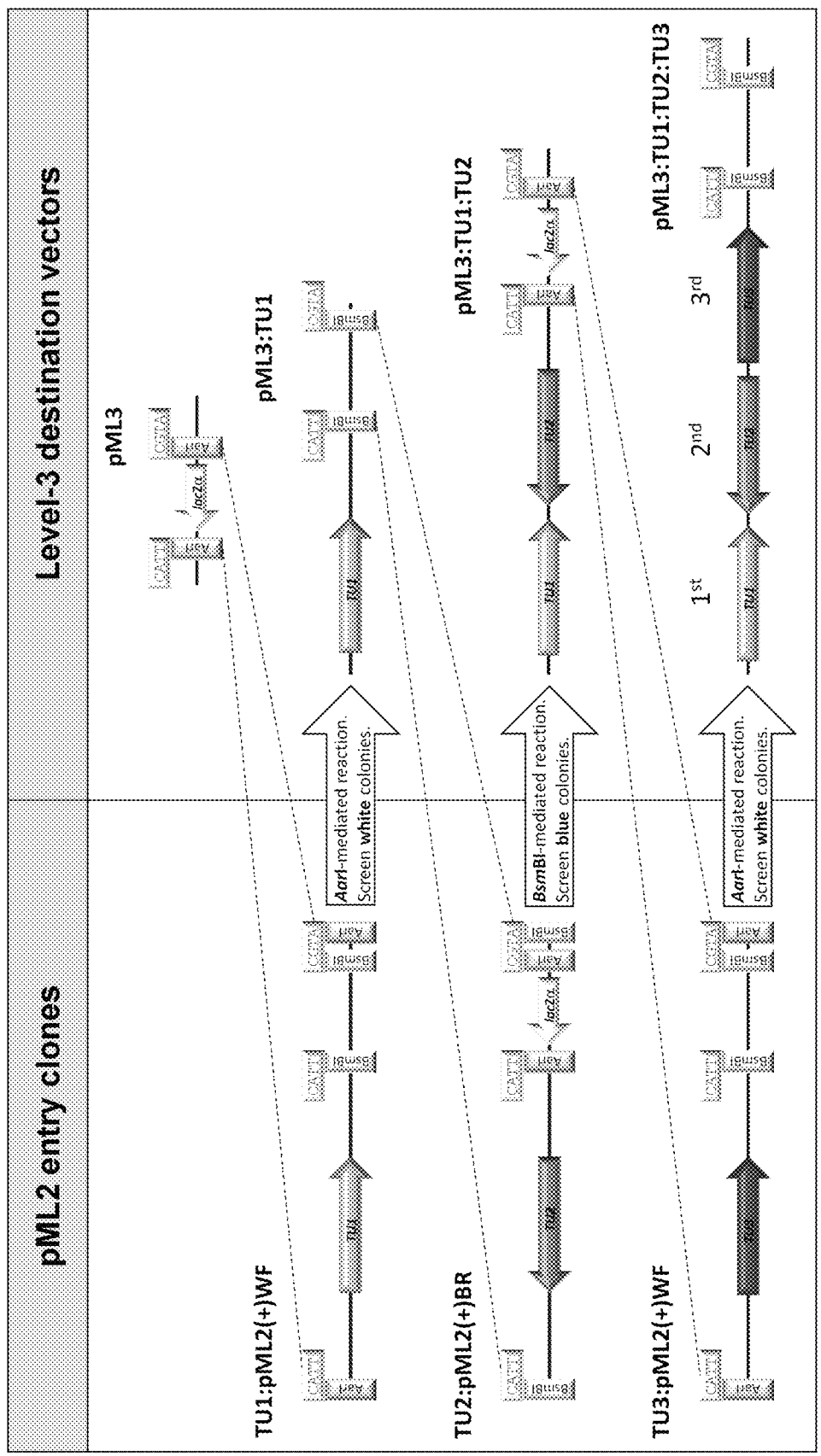
FIG. 14: Principle of MIDAS multigene assembly (level-3).

Assembly of multigene constructs at Level-3 is crucially dependent on the relative configuration of the AarI and BsmBI restriction sites in the MIDAS cassettes located in the "Blue" and "White" pML2 vectors; the nested and inverted configuration of these restriction sites in the White vectors compared to the Blue vectors is a defining feature of the MIDAS multigene assembly process. In the "Blue" vectors, the entire MIDAS cassette has flanking convergent BsmBI sites and nested within is a lacZα gene flanked by divergent AarI sites. In the "White" vectors, the enzyme configuration is inverted (the entire MIDAS cassette has flanking convergent AarI sites and nested within are two divergent BsmBI sites) and there is no lacZα gene. As illustrated in FIG. 14, the nesting and inversion of the restriction sites in the "Blue" and "White" vectors mean that TUs assembled into "White" MIDAS cassettes can be inserted into "Blue" MIDAS cassettes using AarI-mediated Golden Gate reactions and, conversely, TUs assembled into "Blue" MIDAS cassettes can be cloned into "White" MIDAS cassettes using BsmBI-mediated Golden Gate reactions. This cycle of cloning (i.e., alternating between "White" and "Blue" pML2 entry clones) can be repeated indefinitely.

The Golden Gate cloning cassette found in the Level-3 destination vector, pML3, consists of a lacZα gene flanked by divergent AarI sites: [CATT]AarI-lacZa-AarI[CGTA], so the MIDAS Level-3 assembly is always initiated (i.e., the first TU is always added) using an AarI-mediated Golden Gate reaction between pML3 and a TU that has been assembled into a pML2 "White" destination vector (FIG. 14). The plasmid generated is then used in a BsmBI-mediated Golden Gate reaction with a TU cloned into a pML2 "Blue" destination vector. Further TUs are added by following this approach of alternating between AurI- and BsmBI-mediated Golden Gate reactions using pML2 "White" and pML2 "Blue" entry clones, respectively. Thus, each plasmid generated by cloning a TU into the multigene construct becomes the destination vector for the next cycle of TU addition (FIG. 14).

Following each cloning cycle, *E. coli* DH5a cells (or equivalent) are transformed with the Golden Gate reactions, spread onto LB plates supplemented with spectinomycin, IPTG and X-Gal, and positive clones are identified by blue/white screening. Spectinomycin selects for cells that have taken up the Level-3 plasmid and counter selects against any pML2 plasmid backbones. Note that, whereas the lacZα chromogenic marker present in the pML2 "Blue" vectors was not previously utilised during Level-2 assembly of TUs, it is now, at the level of multigene assembly (Level-3), that it becomes used for blue/white screening. Thus, for TUs assembled into the multigene construct using AarI-mediated Golden Gate reactions, white colonies are picked for analysis, while TUs assembled into the multigene construct using BsmBI-mediated Golden Gate reactions are analysed by picking blue colonies (see Table 13).

Figure 15:
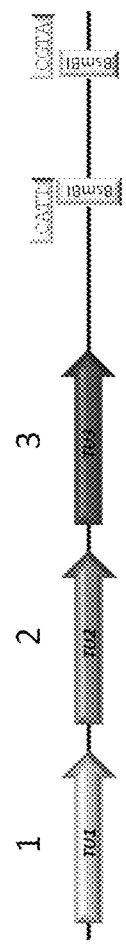
FIG. 15: Overview of MIDAS format.
Figure 15:
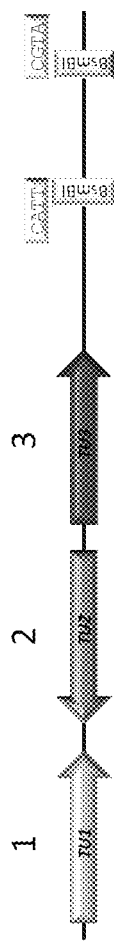
Figure 15:
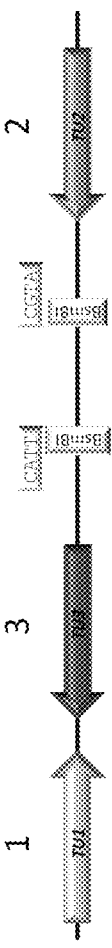

In its simplest configuration, MIDAS can achieve multigene assembly using only two pML2 destination vectors: one "White" vector and one "Blue" vector (FIG. 15A). The full set of eight pML2 vectors are provided to enable maximum user control over: (i) the order in which each TU is added to the growing multigene construct, (ii) the desired orientation (that is, the direction of transcription) of each TU and (iii) the polarity of assembly, i.e., the direction in which incoming TUs are loaded into the multigene construct.

Firstly, and as described earlier, the order of addition of each TU to the growing multigene construct is governed by the choice of "White" or "Blue" pML2 destination vector into which the TUs are assembled.

Secondly, and as described previously when discussing the Level-2 features, the orientation (direction of transcription) of a TU can be freely defined by the choice of "Forward" or "Reverse" pML2 vector into which the TU is assembled. Extending MIDAS to include the option of assembling TUs in either orientation expands the vector suite to four pML2 plasmids (see FIG. 13 and FIG. 15B).

Thirdly, the polarity of multigene assembly (i.e., the direction in which new TUs are added to the growing multigene assembly) can also be freely defined—in this case by assembling TUs in pML2 destination vectors of either "plus" (+) or "minus" (−) polarity (FIG. 13). The use of a pML2(+) entry clone for Level-3 assembly ensures that the TU added next will be added in the same direction as the direction of transcription of the $Spec^R$ gene found in pML3, i.e. the TU assembled next in the multigene construct will be added to the right of the TU that was added using the pML2(+) entry clone (as illustrated in FIG. 15A and FIG. 15B). In contrast, use of a pML2(−) entry clone for Level-3 assembly forces the next TU to be added in the direction opposite to that of the direction of transcription of the Spec$^R$ gene found in pML3, so that the next TU loaded into the multigene construct will be added to the left of the TU that was added using the pML2(−) entry clone. If, however, entry clones of both polarity (i.e., both pML2(+) and pML2(−) entry clones) are used to build the multigene construct, then this confers MIDAS with the ability to switch the direction in which new TUs are added to the Level-3 assembly, and for the hypothetical assembly shown in FIG. 15C all subsequently added TUs will be nested between TU3 and TU2.

Bacterial and Fungal Strains

Routine growth of *Escherichia coli* was performed at 37°C in LB broth. Chemically competent *E. coli* HST08 Stellar cells (Clontech Laboratories, Inc.) were used for routine transformations and maintenance of plasmids. *Penicillium paxilli* strains used in this study are shown in Table 7.

Protocols for MIDAS Level-1 Module Cloning

PCR-amplified modules were purified using spin-column protocols and cloned into the MIDAS Level-1 plasmid, pML1, by BsmBI-mediated Golden Gate assembly. Typically, 1-2 μL (approximately 50-200 ng) of pML1 plasmid DNA from a miniprep was mixed with 1-2 μL of each purified PCR fragment, 1 L of BsmBI (20 U/μL), 1 μL of T4 DNA Ligase (20 U/μL) and 2 μL of 10×T4 DNA Ligase buffer in a total reaction volume of 20 μL. Reactions were incubated at 37°C for 1 to 3 hours and an aliquot (typically 2-3 μL) was transformed into 30 μL of *E. coli* HST08 Stellar competent cells by heat shock. Following the recovery period (i.e., addition of 250 μL SOC medium and incubation at 37° C. for 1 hour), aliquots of the transformation mix were spread onto LB agar plates supplemented with 50 μg/mL spectinomycin, 1 mM IPTG and 50 μg/mL X-Gal. Plates were incubated overnight at 37°C, and white colonies were chosen for analysis.

Protocols for MIDAS Level-2 TU Assembly

Using the modules cloned at Level-1, full-length TUs were assembled into MIDAS Level-2 plasmids by BsaI-mediated Golden Gate assembly. Typically, 40 fmol of pML2 plasmid DNA was mixed with 40 fmol of plasmid DNA of each Level-1 entry clone, 1 μL of BsaI-HF (20 U/μL), 1 μL of T4 DNA Ligase (20 U/μL) and 2 μL of 10×T4 DNA Ligase buffer in a total reaction volume of 20 μL. Reactions were incubated in a DNA Engine PTC-200 Peltier Thermal Cycler (Bio-Rad) using the following parameters: 45 cycles of (2 minutes at 37° C. and 5 minutes at 16° C.), followed by 5 minutes at 50° C. and 10 minutes at 80° C. Reactions were transformed as described for the Level-1 assembly and spread onto LB agar plates containing 75 μg/mL kanamycin and 1.25 mM 4CP. Following overnight incubation at 37° C., colonies were picked for analysis.

Protocols for MIDAS Level-3 Multigene Assembly

Full-length TUs assembled at Level-2, were used to create multigene assemblies in the Level-3 destination vector by alternating Golden Gate assembly using either AarI (for TUs cloned into pML2 "White" vectors) or BsmBI (for TUs cloned into pML2 "Blue" vectors). Typically, 40 fmol of Level-3 destination vector plasmid DNA was mixed with 40 fmol of Level-2 entry clone plasmid DNA, 1 μL of BsaI-HF (20 U/μL), 1 μL of T4 DNA Ligase (20 U/μL) and 2 μL of 10×T4 DNA Ligase buffer in a total reaction volume of 20 μL. Reactions were incubated in a DNA Engine PTC-200 Peltier Thermal Cycler (Bio-Rad) using the following parameters: 45 cycles of (2 minutes at 37° C. and 5 minutes at 16° C.), followed by 5 minutes at 37° C. and 10 minutes at 80° C. Reactions were transformed as described for the Level-1 assembly and spread onto LB agar plates supplemented with 50 μg/mL spectinomycin, 1 mM IPTG and 50 μg/mL X-Gal. Plates were incubated overnight at 37° C. For AarI-mediated assembly reactions, white colonies were chosen for analysis while, for BsmBI-mediated assembly reactions, blue colonies were selected.

Media and Reagents Used for Fungal Work.

CDYE (Czapex-Dox/Yeast extract) medium with trace elements was made with deionized water and contained 3.34% (w/v) Czapex-Dox (Oxoid Ltd., Hampshire, England), 0.5% (w/v) yeast extract (Oxoid Ltd., Hampshire, England), and 0.5% (v/v) trace element solution. For agar plates, Select agar (Invitrogen, California, U.S.A.) was added to 1.5% (w/v).

Trace element solution was made in deionized water and contained 0.004% (w/v) cobalt(II) chloride hexahydrate (Ajax Finechem, Auckland, New Zealand), 0.005% (w/v) copper(II) sulfate pentahydrate (Scharlau, Barcelona, Spain), 0.05% (w/v) iron(II) sulfate heptahydrate (Merck, Darmstadt, Germany), 0.014% (w/v) manganese(II) sulfate tetrahydrate, and 0.05% (w/v) zinc sulfate heptahydrate (Merck, Darmstadt, Germany). The solution was preserved with 1 drop of 12 M hydrochloric acid.

Regeneration (RG) medium was made with deionized water and contained 2% (w/v) malt extract (Oxoid Ltd., Hampshire, England), 2% (w/v) D(+)-glucose anhydrous (VWR International BVBA, Leuven, Belgium), 1% (w/v) mycological peptone (Oxoid Ltd., Hampshire, England), and 27.6% sucrose (ECP Ltd. Birkenhead, Auckland, New Zealand). Depending on whether the media was to be used for plates (1.5% RGA) or overlays (0.8% RGA), Select agar (Invitrogen, California, U.S.A.) was added to 1.5% or 0.8% (w/v), respectively.

Fungal Protocols—Protoplast Preparation

The preparation of fungal protoplasts for transformation was according to Yelton, M. M.; Hamer, J. E.; Timberlake, W. E. *Proc. Natl. Acad. Sci.* 1984, 81 (5), 1470-1474. with modifications. Five 25 mL aliquots of CDYE medium with trace elements, in 100 mL Erlenmeyer flasks, were inoculated with 5×10$^6$ spores and incubated for 28 hours at 28° C. with shaking (200 rpm). The fermentation broth from all five flasks was filtered through a sterile nappy liner and the combined mycelia were rinsed three times with sterile water and once with OM buffer (10 mM Na$_2$HPO$_4$ and 1.2 M MgSO$_4$·7H$_2$O, brought to pH 5.8 with 100 mM NaH$_2$PO$_4$·2H$_2$O). Mycelia were weighed, resuspended in 10 mL of filter-sterilized Lysing Enzymes solution (prepared by resuspending Lysing Enzymes from *Trichoderma harzianum* (Sigma) at 10 mg/mL in OM buffer) per gram of mycelia, and incubated for 16 hours at 30° C. with shaking at 80 rpm. Protoplasts were filtered through a sterile nappy liner into a 250 mL Erlenmeyer flask. Aliquots (5 mL) of filtered protoplasts were transferred into sterile 15 mL centrifuge tubes and overlaid with 2 mL of ST buffer (0.6 M sorbitol and 0.1 M Tris-HCl at pH 8.0). Tubes were centrifuged at 2600×g for 15 minutes at 4° C. The white layer of protoplasts that formed between the OM and ST buffers in each tube was transferred (in 2 mL aliquots) into sterile 15 mL centrifuge tubes, gently washed by pipette resuspension in 5 mL of STC buffer (1 M sorbitol, 50 mM Tris-HCl at pH 8.0, and 50 mM CaCl$_2$)) and centrifuged at 2600×g for 5 minutes at 4° C. The supernatant was decanted off and pelleted protoplasts from multiple tubes were combined by resuspension in 5 mL aliquots of STC buffer. The STC buffer wash was repeated three times until protoplasts were pooled into a single 15 mL centrifuge tube. The final protoplasts pellet was resuspended in 500 μL of STC buffer and protoplast concentration was estimated with a hemocytometer. The protoplast stock was diluted to give a final concentration of $1.25 \times 10^8$ protoplasts per mL of STC buffer. Aliquots of protoplasts (100 µL) were used immediately for fungal transformations and excess protoplasts were preserved in 8% PEG solution (80 µL of protoplasts were added to 20 µL of 40% (w/v) PEG 4000 in STC buffer) in 1.7 mL microcentrifuge tubes and stored at −80° C.

Fungal Protocols—Transformation of *P. paxilli*

Fungal transformations—modified from Vollmer, S. J.; Yanofsky, C. *Proc. Natl. Acad. Sci.* 1986, 83 (13), 4869-4873 and Oliver, R. P.; Roberts, I. N.; Harling, R.; Kenyon, L.; Punt, P. J.; Dingemanse, M. A.; van den Hondel, C. A. M. J. J. *Curr. Genet.* 1987, 12 (3), 231-233.—were carried out in 1.7 mL micro-centrifuge tubes containing 100 µL ($1.25 \times 10^7$) protoplasts, either freshly prepared in STC buffer, or stored in 8% PEG solution (as described above). A solution containing 2 µL of spermidine (50 mM in $H_2O$), 5 µL heparin (5 mg/mL in STC buffer), and 5 µg of plasmid DNA (250 µg/mL) was added to the protoplasts and, following incubation on ice for 30 minutes, 900 µL of 40% PEG solution (40% (w/v) PEG 4000 in STC buffer) was added. The transformation mixture was incubated on ice for a further 15-20 minutes, transferred to 17.5 mL of 0.8% RGA medium (prewarmed to 50° C.) in sterile 50 mL tubes, mixed by inversion, and 3.5 mL aliquots were dispensed onto 1.5% RGA plates. Following overnight incubation at 25° C., 5 mL of 0.8% RGA (containing sufficient geneticin to achieve a final concentration of 150 µg per mL of solid media) was overlaid onto each plate. Plates were incubated for a further 4 days at 25° C. and spores were picked from individual colonies and streaked onto CDYE agar plates supplemented with 150 µg/mL geneticin. Streaked plates were incubated at 25° C. for a further 4 days. Spores from individual colonies were suspended in 50 µL of 0.01% (v/v) triton X-100 and 5×5 µL aliquots of the spore suspension was transferred onto new CDYE agar plates supplemented with 150 µg/mL geneticin. Sporulation plates were incubated at 25° C. for 4 days and spore stocks were prepared as follows. Colony plugs from the sporulation plates were suspended in 2 mL of 0.01% (v/v) triton X-100, and 800 µL of suspended spores were mixed with 200 µL of 50% (w/v) glycerol in a 1.7 mL micro-centrifuge tube. Spore stocks were used to inoculate 50 mL of CDYE media, flash frozen in liquid nitrogen and stored at −80° C.

Indole Diterpene Production and Extraction

Fungal transformants were grown in 50 mL of CDYE medium with trace elements for 7 days at 28° C. in shaker cultures (≥200 rpm), in 250 mL Erlenmeyer flasks capped with cotton wool. Mycelia were isolated from fermentation broths by filtration through nappy liners, transferred to 50 mL centrifuge tubes (Lab Serv®, Thermo Fisher Scientific) and indole diterpenes were extracted by vigorously shaking the mycelia (≥200 rpm) in 2-butanone for ≥45 minutes.

Thin-Layer Chromatography

The 2-butanone supernatant (containing extracted indole diterpenes) was used for thin-layer chromatography (TLC) analysis on solid phase silica gel 60 aluminium plates (Merck). Indole diterpenes were chromatographed with 9:1 chloroform:acetonitrile or 8:2 dichloromethane:acetonitrile and visualized with Ehrlich's reagent (1% (w/v) p-dimethylaminobenzaldehyde in 24% (v/v) HCl and 50% ethanol).

Liquid Chromatography-Mass Spectrometry

Samples were prepared for liquid chromatography-mass spectrometry (LC-MS) from those transformants that tested positive by TLC. Accordingly, a 1 mL sample of the 2-butanone supernatant (containing extracted indole diterpenes) was transferred to a 1.7 mL micro-centrifuge tube and the 2-butanone was evaporated overnight. Contents were resuspended in 100% acetonitrile and filtered through a 0.2 µm membrane into an LC-MS vial. LC-MS samples were chromatographed on a reverse phase Thermo Scientific Accucore 2.6 µm C18 (50× 2.1 mm) column attached to an UltiMate® 3000 Standard LC system (Dionex, Thermo Fisher Scientific) run at a flow rate of 0.200 mL/minute and eluted with aqueous solutions of acetonitrile containing 0.01% formic acid using a multistep gradient method (Table 14). Mass spectra were captured through in-line analysis on a maXis™ II quadrupole-time-of-flight mass spectrometer (Bruker).

Large Scale Indole Diterpene Purification for NMR Analysis

Fungal transformants that produced high levels of novel indole diterpenes were grown in ≥1 litre of CDYE medium with trace elements, as described under "Indole diterpene production and extraction". Mycelia were pooled into 1 litre Schott bottles containing stir bars. 2-butanone was added and indole diterpenes were extracted overnight with stirring (≥700 rpm). Extracts were filtered through Celite® 545 (J. T. Baker®) and dry loaded onto silica with rotary evaporation for crude purification by silica column prior to a final purification by semi-preparative HPLC. A 1 mL aliquot of crude extract was injected onto a semi-preparative reversed phase Phenomenex 5 µm C18(2) 100 Å (250×15 mm) column attached to an UltiMate® 3000 Standard LC system (Dionex, Thermo Fisher Scientific) run at a flow rate of 8.00 mL/minute. Multistep gradient methods were optimized for the purification of different sets of indole diterpenes. The purity of each indole diterpene was assessed by LC-MS and the structure was identified by NMR.

NMR

NMR samples were prepared in deuterated chloroform. Compounds were analysed by standard one-dimensional proton and carbon-13 NMR, two-dimensional correlation spectroscopy (COSY), heteronuclear single quantum correlation spectroscopy (HSQC), and heteronuclear multiple bond correlation spectroscopy (HMBC).

Tables 1-14 referenced in this specification are set out below:

TABLE 1

Functional assignment of predicted genes in the putative nodulisporic acid gene cluster.

| | Size of encoded protein (aa) | Predicted function [Specific Function] | Organism | Most notable BLASTp match | |
|---|---|---|---|---|---|
| Gene | | | | E-value % identity/ % coverage | Protein name and accession number |
| nodI | 1664 | WD40 domain protein | *Hypoxylon* sp. CO27-5 | 0 36% ID/80% | OTA80149 |
| nodW | 608 | Cytochrome P450 oxygenase [terminal-C dioxygenase] | *Aspergillus aculeatus* | 9.00E−153 44% ID/97% | XP_020058732 |

TABLE 1-continued

Functional assignment of predicted genes in the putative nodulisporic acid gene cluster.

| Gene | Size of encoded protein (aa) | Predicted function [Specific Function] | Organism | E-value % identity/ % coverage | Protein name and accession number |
|---|---|---|---|---|---|
| nodR* | 511 | Cytochrome P450 oxygenase | *Penicillium simplicissimum* | 3.00E−108 36% ID/97% | PtmU/BAU61563 |
| nodX | 593 | Cytochrome P450 oxygenase | *Hypoxylon* sp. | 0 62% ID/70% | OTA78491 |
| nodM* | 463 | FAD-dependent oxygenase [IDT mono-epoxidase] | *Aspergillus flavus* | 5.00E−173 55% ID/93% | AtmD/Q672V4 |
| nodB* | 243 | IDT cyclase [IDT cyclase] | *Penicillium crustosum* | 9.00E−119 68% ID/99% | PenB/AGZ20190 |
| nodO* | 448 | FAD-dependent oxygenase | *Penicillium janthinellum* | 2.00E−160 60% ID/97% | JanO/AGZ20488 |
| nodJ | 514 | Cytochrome P450 oxygenase | *Aspergillus clavatus* | 3.00E−148 42% ID/99% | XP_001270361 |
| nodC* | 326 | Geranylgeranyl transferase [Geranylgeranyl transferase] | *Penicillium crustosum* | 2.00E−136 66% ID/83% | PenC/AGZ20189 |
| nodY1 | 431 | FAD-dependent oxygenase | *Penicillium oxalicum* | 2.00E−71 34% ID/99% | OxaD/AOC80388 |
| nodD2* | 434 | prenyl transferase | *Penicillium janthinellum* | 1.00E−144 48% ID/96% | JanD/AGZ20478 |
| nodD1* | 431 | prenyl transferase | *Penicillium janthinellum* | 1.00E−155 53% ID/94% | JanD/AGZ20478 |
| nodY2 | 461 | FAD-dependent oxygenase | *Aspergillus alliaceus* | 3.00E−105 42% ID/98% | AspB/P0DOW1 |
| nodZ | 477 | Cytochrome P450 oxygenase | *Penicillium flavigenum* | 7.00E−166 48% ID/96% | OQE14847 |
| nodS | 535 | Not stated | *Hypoxylon* sp. CO27-5 | 9.00E−139 46% ID/94% | OTA93952 |

Naming of genes in IDT clusters has followed the *A. nidulans* naming convention where genes are given a name with a with a three letter prefix in lower case that designates species, followed by a single letter suffix in upper case that designates gene function written in italic font (e.g. paxC). Naming of the corresponding protein product follows the same rules except that the initial letter of the prefix is upper case and the entire name is written in normal (non-italic) font (e.g. PaxC is the protein product of paxC). Thus, a nod name was assigned to each *H. pulicicidum* gene in the NAA 10 gene cluster. *H. pulicicidum* genes that share homology (>35% amino acid identity of predicted translational products) with genes found in known IDT pathways are followed by an asterisk (*) and, with the exception of nodR, were given letters corresponding to known confirmed genes (e.g. the protein encoded by nodC shares 52.8% amino acid identity with the protein product of paxC). The genes that do not share homology with known IDT genes were assigned letters that are not shared with any of the confirmed IDT genes. Notably, the cluster contains two sets of paralogous genes (share >40% amino acid identity with each other), which we have distinguished using numbers (i.e. nodD1/nodD2 and nodY1/nodY2). Closest matches were identified using BLASTp (protein-protein BLAST) against the non-redundant protein sequence database with 'expect threshold' set at 10 and 'word size' set at 6. The BLOSUM62 scoring matrix was applied with a gap opening penalty of 11 and a gap extension penalty of 1 with conditional compositional score matrix adjustment.

TABLE 2

Similarity matrix of geranylgeranyl transferases ('C' enzymes).

| Enzyme | PaxC | NodC | LtmC | AtmC | JanC | PenC |
|---|---|---|---|---|---|---|
| PaxC | 100 | *52.3* | *35.3* | *54.3* | *70.9* | *60.5* |
| NodC | 66.7 | 100 | *38.8* | *55.1* | *55.4* | *54.4* |
| LtmC | 54 | 61.7 | 100 | *40.2* | *36.4* | *39.5* |
| AtmC | 69.9 | 70.5 | 61.5 | 100 | *58.3* | *63.6* |
| JanC | 79.5 | 70.3 | 55.5 | 74.1 | 100 | *66.7* |
| PenC | 73.4 | 70.5 | 59.1 | 78 | 79.2 | 100 |

Numbers in italics represent % identity scores. Numbers in bold represent % similarity scores for amino acid residues.

TABLE 3

Similarity matrix of 3-gernaylkgeranylindole epoxidases ('M' enzymes).

| Enzyme | LtmM | NodM | AtmM | PenM | JanM | PaxM |
|---|---|---|---|---|---|---|
| LtmM | 100 | *37.3* | *38.2* | *36.8* | *36.9* | *37.9* |
| NodM | 57.2 | 100 | *48.3* | *51.2* | *52.9* | *48.6* |
| AtmM | 56.3 | 63.4 | 100 | *48.3* | *47.9* | *48.9* |
| PenM | 54.8 | 66 | 62.8 | 100 | *61.6* | *60.6* |
| JanM | 54.7 | 67 | 61.6 | 75.1 | 100 | *66.7* |
| PaxM | 56.6 | 65.8 | 64.4 | 74 | 79.9 | 100 |

Numbers in italics represent % identity scores and numbers in bold represent % similarity scores for amino acid residues.

TABLE 4

Similarity matrix of indole diterpene cyclases ('B' enzymes).

| Enzyme | PaxB | NodB | LtmB | AtmB | JanB | PenB |
|---|---|---|---|---|---|---|
| PaxB | 100 | *63* | *49.6* | *62.1* | *77* | *72.4* |
| NodB | 78.2 | 100 | *48.8* | *64.2* | *65.4* | *67.9* |
| LtmB | 65.6 | 63.5 | 100 | *48.8* | *51.6* | *52* |
| AtmB | 77 | 78.2 | 65.2 | 100 | *67.5* | *70.8* |
| JanB | 87.2 | 77.8 | 66.4 | 79.8 | 100 | *78.2* |
| PenB | 87.7 | 80.2 | 66.4 | 82.3 | 86.4 | 100 |

Numbers in italics represent % identity scores and numbers in bold represent % similarity scores for amino acid residues.

TABLE 5

Similarity matrix of indole diterpene prenyl transferases ('D' and 'E' enzymes compared to NodD1 and NodD2).

| Enzyme | NodD2 | PaxD | NodD1 | JanD | AtmD | LtmE | PenD | PenE |
|---|---|---|---|---|---|---|---|---|
| NodD2 | 100 | *42.3* | *44.7* | *45* | *31.6* | *11.3* | *32.6* | *23.3* |
| PaxD | 61.9 | 100 | *44.9* | *65.8* | *31.3* | *11.4* | *31.4* | *24.3* |
| NodD1 | 60.7 | 63.6 | 100 | *49.2* | *29.2* | *11.2* | *29.7* | *22.7* |
| JanD | 63.1 | 80.6 | 65.6 | 100 | *30.5* | *11.7* | *31.9* | *25.2* |
| AtmD | 49.6 | 49.4 | 47.6 | 50.2 | 100 | *11.2* | *28.6* | *25.2* |
| LtmE | 20 | 20.7 | 21 | 21.6 | 19.5 | 100 | *10.8* | *11.6* |
| PenD | 54.4 | 53.5 | 50.7 | 51.9 | 48.1 | 20.9 | 100 | *24.3* |
| PenE | 41.1 | 40.5 | 40.2 | 41.3 | 37.4 | 21.7 | 41.3 | 100 |

Numbers in italics represent % identity scores and bold numbers represent % similarity scores for amino acid residues.

TABLE 6

Similarity matrix of indole diterpene FAD dependent oxidative cyclases ('O' enzymes).

| Enzyme | PenO | JanO | NodO | PaxO |
|---|---|---|---|---|
| PenO | 100 | *42.9* | *44.9* | *40.3* |
| JanO | 59.3 | 100 | *50.7* | *71.9* |
| NodO | 61.9 | 69.2 | 100 | *48.7* |
| PaxO | 56.9 | 84 | 67 | 100 |

Numbers in italics represent % identity scores and numbers in bold represent % similarity scores for amino acid residues.

TABLE 7

Table of fungal species used in this study.

| *Hypoxylon pulicicidum* (*Nodulisporium* sp.) strain | Description | Indole diterpene phenotype Nodulisporic acid A | Source[reference(s)] |
|---|---|---|---|
| ATCC® 74245™ | Wild type | + | ATCC[25] |

| *Penicillium paxilli* strain | Description | Indole diterpene phenotype Paspaline | Paxilline | Source[reference(s)] |
|---|---|---|---|---|
| PN2013 (ATCC®26601™) | Wild type | + | + | Barry Scott, Massey University[24] |
| PN2250 (CY2) | PN2013/Deletion of entire PAX locus (ΔPAX); Hyg[R] | − | − | Barry Scott, Massey University[15] |
| PN2257 | PN2013/ΔpaxM::P$_{glcA}$-hph-T$_{trpC}$; Hyg[R] | − | − | Barry Scott, Massey University[15] |
| PN2290 | PN2013/ΔpaxC::P$_{trpC}$-hph; Hyg[R] | − | − | Barry Scott, Massey University[28] |

TABLE 8

PCR primers for amplification of transcription unit modules (TUMs).

| TUM | Primer name | Primer sequence (5' to 3') | |
|---|---|---|---|
| | *Hypoxylon pulicicidum* primers | | |
| | nodW | | |
| nodW$_{CDS}$ | P4502 frag 1 F | cgatgtacgtctcaCTCGAATGactttagctattta ggcatcagttgcc | SEQ ID NO: 57 |
| | P4502 frag 1 R | actgctcgtctcaACTCccgctgcgagccgct | SEQ ID NO: 58 |
| | P4502 frag 2 F | acgtaccgtctccGAGTccggtcctggtggagtgatc | SEQ ID NO: 59 |
| | P4502 frag 2 R | gaccttcgtctctGTCTcaAAGCctaagttatgcc cagatatttccag | SEQ ID NO: 60 |
| | nodM | | |
| nodM$_{CDS}$ | nodM frag1 F | cgatgtacgtctcaCTCGAATGtctaccctgagt tcaagg | SEQ ID NO: 61 |
| | nodM frag1 R | cagtcacgtctcaACGCctctcaagaacgatgtggga aattc | SEQ ID NO: 62 |
| | nodM frag2 F | gtgcatcgtctcaGCGTagtgtaatcgcaccagag | SEQ ID NO: 63 |
| | nodM frag2 R | gaccttcgtctctGTCTcaAAGCctatgaagcgat gtctctaatatggagtaac | SEQ ID NO: 64 |
| | nodB | | |
| nodB$_{CDS}$ | nodB F | cgatgtacgtctcaCTCGAATGgatggattcgatc gttccaatg | SEQ ID NO: 65 |
| | nodB R | gaccttcgtctctGTCTcaAAGCttattgagccttc cgcgcattg | SEQ ID NO: 66 |
| | nodC | | |
| nodC$_{CDS}$ | nodC frag1 F | cgatgtacgtctcaCTCGAATGtccttaggtttaca gtgcttgg | SEQ ID NO: 67 |
| | nodC frag1 R | cattgacgtctcgGTCAcgtcgccaaaccagcga | SEQ ID NO: 68 |
| | nodC frag2 F | gtcacgcgtctctTGACggcctcactagctttcc | SEQ ID NO: 69 |
| | nodC frag2 R | gaccttcgtctctGTCTcaAAGCtcaatgcgtaag atcgagtttctcctttct | SEQ ID NO: 70 |
| | *Penicillium paxilli* primers | | |
| | paxG | | |
| paxG$_{Pro}$UTR | PpaxG F | cgatgtacgtctcaCTCGGGAGattcacgacctgt gactagtcaa | SEQ ID NO: 71 |
| | PpaxG R | gaccttcgtctctGTCTca_CATT_ggcgtcgaactt gatgaagttttc | SEQ ID NO: 72 |
| paxG$_{CDS}$ | paxG frag1 F | cgatgtacgtctcaCTCGAATGtcctacatccttg cagaag | SEQ ID NO: 73 |
| | paxG frag1 R | cttctacgtctcgTACTgttctaatcgtgcttggtg | SEQ ID NO: 74 |
| | paxG frag2 F | gcacgacgtctccAGTAcaggtgctagaagatgacg ttgac | SEQ ID NO: 75 |
| | paxG frag2 R | aggcgccgtctccACCAatctcttcaatcttgcttgttg ga | SEQ ID NO: 76 |
| | paxG frag3 F | gattgacgtctctTGGTgacccccgcgcctt | SEQ ID NO: 77 |
| | paxG frag3 R | gtcgaccgtctctTTCCctagtatattggaagctcccc g | SEQ ID NO: 78 |
| | paxG frag4 F | tccaatcgtctcgGGAAaccctaagtcgacttagtgc g | SEQ ID NO: 79 |
| | paxG frag4 R | gaccttcgtctctGTCTcaAAGCttaaactcttcctt tctcattagtaggg | SEQ ID NO: 80 |
| paxGUTR$_{term}$ | TpaxG F | cgatgtacgtctcaCTCGGCTTtcaatcgtgctgc atttctctt | SEQ ID NO: 81 |
| | TpaxG R | gaccttcgtctctGTCTcaAGCGtcactcccgagc aatattgct | SEQ ID NO: 82 |
| | paxC | | |
| paxC$_{Pro}$UTR | PpaxC F2 | cgatgtacgtctcaCTCGGGAGacaacaaaaag atcagccaatgg | SEQ ID NO: 83 |
| | PpaxC R2 | gaccttcgtctctGTCTca_CATT_aaaatgggacct acaccctgaa | SEQ ID NO: 84 |
| paxC$_{CDS}$ | paxC frag1 F | cgatgtacgtctcaCTCGAATGggcgtagcagg ga | SEQ ID NO: 85 |
| | paxC frag1 R | cattgacgtctccACGGcgccagacaaggga | SEQ ID NO: 86 |

TABLE 8-continued

PCR primers for amplification of transcription unit modules (TUMs).

| TUM | Primer name | Primer sequence (5' to 3') | |
|---|---|---|---|
| | paxC frag2 F | cccttgcgtctcgCCGTgacggagtcaatgggttc | SEQ ID NO: 87 |
| | paxC frag2 R | gacctttcgtctctGTCTcaAAGCtcatgccttcaggtcaagcttc | SEQ ID NO: 88 |
| paxC$_{UTRterm}$ | TpaxC F | cgatgtacgtctcaCTCGGCTTtttggccttgtgaaatatgggactac | SEQ ID NO: 89 |
| | TpaxC R | gacctttcgtctctGTCTcaAGCGatctctgtcatgtcggatatcagat | SEQ ID NO: 90 | paxM

| | | | |
|---|---|---|---|
| paxM$_{ProUTR}$ | PpaxM F | cgatgtacgtctcaCTCGGGAGgttgttggcatgggagtaggat | SEQ ID NO: 91 |
| | PpaxM R | gacctttcgtctctGTCTcaCATTggtttctgaatcttaaagatacatgaaaag | SEQ ID NO: 92 |
| paxM$_{CDS}$ | paxM frag1 F | cgatgtacgtctcaCTCGAATGgaaaaggccgagtttcaag | SEQ ID NO: 93 |
| | paxM frag1 R | tgacaacgtctcgTCCAtcgaataaagcgttgacttgc | SEQ ID NO: 94 |
| | paxM frag2 F | acgcttcgtctcaTGGActcactattgtcacaatccatggaaaag | SEQ ID NO: 95 |
| | paxM frag2 R | gacctttcgtctctGTCTcaAAGCttaaacttgaagaaaataaaacttcagggcac | SEQ ID NO: 96 |
| paxM$_{UTRterm}$ | TpaxM frag1 F | cgatgtacgtctcaCTCGGCTTaccattggagcaattttggttttc | SEQ ID NO: 97 |
| | TpaxM frag1 R | gttcgccgtctcgACTCgattgcttgtgggtct | SEQ ID NO: 98 |
| | TpaxM frag2 F | acaagccgtctccGAGTccagccagcgaacttg | SEQ ID NO: 99 |
| | TpaxM frag2 R | gacctttcgtctctGTCTcaAGCGttttggcttacttcagtttaactgttttg | SEQ ID NO: 100 | paxB

| | | | |
|---|---|---|---|
| paxB$_{ProUTR}$ | PpaxB F | cgatgtacgtctcaCTCGGGAGaaggctgtgttggagagaatc | SEQ ID NO: 101 |
| | PpaxB R | gacctttcgtctctGTCTcaCATTagtttctaaggttgacgtgggaaaaag | SEQ ID NO: 102 |
| paxB$_{CDS}$ | paxB F | cgatgtacgtctcaCTCGAATGgacggttttgatgtttcccaa | SEQ ID NO: 103 |
| | paxB R | gacctttcgtctctGTCTcaAAGCtcaatttgcttttttcggcccgcttatgc | SEQ ID NO: 104 |
| paxB$_{UTRterm}$ | TpaxB F | cgatgtacgtctcaCTCGGCTTtcggcagttgagggtgaaac | SEQ ID NO: 105 |
| | TpaxB R | gacctttcgtctctGTCTcaAGCGggttaacaatgaggaacgatgaacag | SEQ ID NO: 106 |

Additional primers
trpC

| | | | |
|---|---|---|---|
| trpC$_{ProUTR}$ | PtrpC frag1 F | cgatgtacgtctcaCTCGGGAGgaattcatgccagttgttcccag | SEQ ID NO: 107 |
| | PtrpC frag1 R | cgatgtacgtctcaGCTTggccgactcgctg | SEQ ID NO: 108 |
| | PtrpC frag2 F | cacctttcgtctccAAGCagacgtgaagcaggacgg | SEQ ID NO: 109 |
| | PtrpC frag2 R | cgatgtcgtctcgCAGAccattgcacaagcctc | SEQ ID NO: 110 |
| | PtrpC frag3 F | gacctttcgtctcgTCTGcgcatggatcgctgc | SEQ ID NO: 111 |
| | PtrpC frag3 R | gacctttcgtctctGTCTcaCATTatcgatgcttgggtagaataggtaag | SEQ ID NO: 112 |
| trpC$_{UTRterm}$ | T trpC frag1 F | cgatgtacgtctcaCTCGGCTTgatccacttaacgttactgaaatcatcaaac | SEQ ID NO: 113 |
| | T trpC frag1 R | gacctttcgtctctCTGCttgatctcgtctgccga | SEQ ID NO: 114 |
| | T trpC frag2 F | cgatgtacgtctcaGCAGatcaacggtcgtcaaga | SEQ ID NO: 115 |
| | T trpC frag2 R | gacctttcgtctctGTCTcaAGCGtctagaaagaaggattacctctaaacaagtgt | SEQ ID NO: 116 | nptII

| | | | |
|---|---|---|---|
| nptII$_{CDS}$ | ntpII F | cgatgtacgtctcaCTCGAATGattgaacaagatggattgcacg | SEQ ID NO: 117 |
| | ntpII R | gacctttcgtctctGTCTcaAAGCctcagaagaactcgtcaagaaggc | SEQ ID NO: 118 |

The forward and reverse PCR primers used for amplification of TUMs (i.e. promoters (ProUTR), coding sequences (CDSs), and terminators (UTRterm)) are listed. Primers used to amplify TUM fragments for domestication purposes (i.e. removal of internal sites for AarI, BsaI or BsmBI) are underlined (e.g., P4502 frag 1 R). The template for amplification of nod CDSs was genomic DNA from *Hypoxylon pulicicidum* strain ATCC® 74245™.[25] The template for amplification of pax gene TUMs was genomic DNA from *Penicillium paxilli* strain ATCC® 26601™ (PN2013).[24] The PCR products used to produce the trpC ProUTR module, nptII CDS module (conferring resistance to geneticin), and trpC$_{UTRterm}$ module were all amplified from plasmid pII99.[41] The BsmBI recognition sites are shown in bold lower case text (cgtctc), with the overhangs generated following BsmBI cleavage shown by the upper case italics text. The 5' (prefix) and 3' (suffix) nucleotide bases, which flank each TUM and form the basis of the address system for each of the MIDAS modules, are shown in bold upper case text, and bold upper case italic text respectively.

TABLE 9

MIDAS Level-1 plasmid library: Assembly of TUMs in pML1.
[GGAG] [AATG] [GCTT] [*CGCT*]

| ProUTR modules | | CDS modules | | UTRterm modules | |
|---|---|---|---|---|---|
| Plasmid name | Description | Plasmid name | Description | Plasmid name | Description |
| pSK1 | paxG$_{ProUTR}$ | pKV45 | nodW$_{CDS}$ | pSK3 | paxG$_{UTRterm}$ |
| pKV28 | paxC$_{ProUTR}$ | pKV59 | nodM$_{CDS}$ | pSK12 | paxC$_{UTRterm}$ |

TABLE 9-continued

MIDAS Level-1 plasmid library: Assembly of TUMs in pML1.
[GGAG] [AATG] [GCTT] [*CGCT*]

| ProUTR modules | | CDS modules | | UTRterm modules | |
|---|---|---|---|---|---|
| Plasmid name | Description | Plasmid name | Description | Plasmid name | Description |
| pSK4 | paxM$_{ProUTR}$ | pSK18 | | pSK6 | paxM$_{UTRterm}$ |
| pSK7 | paxB$_{ProUTR}$ | pSK19 | nodB$_{CDS}$ | pSK9 | paxB$_{UTRterm}$ |
| pSK17 | trpC$_{ProUTR}$ | pSK20 | nodC$_{CDS}$ | pSK15 | trpC$_{UTRterm}$ |
| | | pSK2 | paxG$_{CDS}$ | | |
| | | pSK11 | paxC$_{CDS}$ | | |
| | | pSK5 | paxM$_{CDS}$ | | |
| | | pSK16 | nptII$_{CDS}$ | | |

This table represents the MIDAS level-1 TUMs that we used to assemble MIDAS level-2 TUs (Table 10). The 4 base prefixes and suffixes (5' to 3') that flank each TUM are shown at the top of the table to highlight the sequences used to bind the TUMs together to make MIDAS level-2 TUs. These 4 base flanking regions are depicted in the primer table (Table 8) in bold upper case text (forward addresses) and bold upper case italics text (reverse addresses).

TABLE 10

MIDAS Level-2 plasmid library: Assembly of TUs in pML2 destination vectors

| TU | Level-1 entry clones used for TU assembly | | | pML2 destination vector | Level-2 entry clones | |
|---|---|---|---|---|---|---|
| | ProUTR | CDS | UTRterm | | Name | Description |
| nodW | pSK17 | pKV45 | pSK15 | pML2(+)WR | pKV52 | ◄ (T$_{trpC}$-nodW-P$_{trpC}$):pML2(+)WR |
| | | | | pML2(+)BR | pSK67 | ◄ (T$_{trpC}$-nodW-P$_{trpC}$):pML2(+)BR |
| nodM | pSK4 | pKV59 | pSK6 | pML2(+)BF | pKV57 | (P$_{trpC}$-nodM-T$_{trpC}$)► :pML2(+)BF |
| | | | pSK18 | pML2(+)WF | pSK28 | (P$_{trpC}$-nodM-T$_{trpC}$)► :pML2(+)WF |
| nodB | pSK7 | pSK19 | pSK9 | pML2(+)BR | pSK29 | ◄ (T$_{trpC}$-nodB-P$_{trpC}$):pML2(+)BR |
| nodC | pSK17 | pSK20 | pSK15 | pML2(+)BF | pKV26 | (P$_{trpC}$-nodC-T$_{trpC}$)► :pML2(+)BF |
| | pKV28 | | pSK12 | pML2(+)WF | pSK60 | (P$_{trpC}$-nodC-T$_{trpC}$)► :pML2(+)WF |
| paxG | pSK1 | pSK2 | pSK3 | pML2(+)BR | pSK21 | ◄ (T$_{paxG}$-paxG-P$_{paxG}$):pML2(+)BR |
| paxC | pKV28 | pSK11 | pSK12 | pML2(+)WF | pSK59 | (P$_{paxC}$-paxC-T$_{paxC}$)► :pML2(+)WF |
| paxM | pSK4 | pSK5 | pSK6 | pML2(+)WR | pSK22 | ◄ (T$_{paxM}$-paxM-P$_{paxM}$):pML2(+)WR |
| nptII | pSK17 | pSK16 | pSK15 | pML2(+)WF | pSK26 | (P$_{trpC}$-nptII-T$_{trpC}$)► :pML2(+)WF |

This table represents the construction of the MIDAS level-2 TUs that were used to assemble MIDAS level-3 multi-gene plasmids for heterologous expression studies. The names of the Level-2 entry plasmids produced are shown in bold. TUs are described by the CDS they contain and TU orientation, determined by the pML2 destination vector, is shown by the arrowhead (▶ for forward (F) destination vector and ◀ for reverse (R) destination vector) in the Level-2 description.

TABLE 11

MIDAS Level-3 plasmid library: Multi-gene assemblies in pML3

| Step | Level-2 entry clone Name | Description | Destination vector | Golden Gate reaction | Product Level-3 plasmid Name | Description | Plasmid size (kb) |
|---|---|---|---|---|---|---|---|
| 1 | pSK26 | (P$_{trpC}$-nptII-T$_{trpC}$)▶ :pML2(+)WF | pML3 | AarI | pKV22 | pML3:nptII▶ | 5.6 |
| 2 | pKV26 | (P$_{trpC}$-nodC-T$_{trpC}$)▶ :pML2(+)BF | pKV22 | BsmBI | pKV27 | pML3:nptII▶ :nodC▶ | 9.0 |
| 2 | pKV57 | (P$_{trpC}$-nodM-T$_{trpC}$)▶ :pML2(+)BF | pKV22 | BsmBI | pKV63 | pML3:nptII▶ :nodM▶ | 9.4 |
| 3 | pKV52 | ◀(T$_{trpC}$-nodW-P$_{trpC}$):pML2(+)WR | pKV63 | AarI | pKV64 | pML3:nptII▶ : nodM▶ :◀ nodW | 13.0 |
| 1 | pSK26 | (P$_{trpC}$-nptII-T$_{trpC}$)▶ :pML2(+)WF | pML3 | AarI | pSK33 | pML3:nptII▶ | 5.6 |
| 2 | pSK21 | ◀(T$_{paxG}$-paxG-P$_{paxG}$):pML2(+)BR | pSK33 | BsmBI | pSK34 | pML3:nptII▶ :◀ paxG | 8.2 |
| 3 | pSK22 | ◀(T$_{paxM}$-paxM-P$_{paxM}$):pML2(+)WR | pSK34 | AarI | pSK36 | pML3:nptII▶ :◀ paxG: ◀ paxM | 11.5 |
| 4 | pSK29 | ◀(T$_{trpC}$-nodB-P$_{trpC}$):pML2(+)BR | pSK36 | BsmBI | pKV73 | pML3:nptII▶ :◀ paxG: ◀ paxM:◀ nodB | 14.1 |
| 5 | pSK59 | (P$_{paxC}$-paxC-T$_{paxC}$)▶ :pML2(+)WF | pSK73 | AarI | pKV74 | pML3:nptII▶ :◀ paxG: ◀ paxM:◀ nodB:paxC▶ | 16.3 |
| 3 | pSK28 | (P$_{trpC}$-nodM-T$_{trpC}$)▶ :pML2(+)WF | pSK34 | AarI | pSK35 | pML3:nptII▶ :◀ paxG: nodM▶ | 11.5 |
| 4 | pSK29 | ◀(T$_{trpC}$-nodB-P$_{trpC}$):pML2(+)BR | pSK35 | BsmBI | pSK38 | pML3:nptII▶ :◀ paxG: nodM▶ :◀ nodB | 14.1 |
| 5 | pSK60 | (P$_{trpC}$-nodC-T$_{trpC}$)▶ :pML2(+)WF | pSK38 | AarI | pSK66 | pML3:nptII▶ :◀ paxG: nodM▶ :◀ nodB:nodC▶ | 16.3 |
| 6 | pSK67 | ◀(T$_{trpC}$-nodW-P$_{trpC}$):pML2(+)BR | pSK66 | BsmBI | pSK68 | pML3:nptII▶ :◀ paxG: nodM▶ :◀ nodB: nodC▶ :◀ nodW | 20.5 |

The table shows the Level-2 entry clone and Level-3 destination vectors used to construct the multi-gene plasmids. The names of the plasmids produced during each cycle of Level-3 assembly are shown in bold. The number of level 3 assembly reactions used to create the level-3 plasmid is indicated by number in the step column. TUs are annotated with the name of the CDS they contain. TU orientation is shown by the arrowhead.

TABLE 12

Generalised primer design for amplification of ProUTR, CDS and UTRterm modules to be cloned into pML1.

| TUM | Primer | Primer sequence (5' to 3') |
|---|---|---|
| [GGAG]-ProUTR-[AATG] | Forward | 5'-cgatgtacgtctcaCTCGGGAG (SEQ ID NO: 119) (+18-25 bases specific for the 5' end of the promoter)-3' |
| | Reverse | 5'-gacctttcgtctctGTCTcaCATT (SEQ ID NO: 120) (+18-25 bases specific for the 3' end of the 5'UTR)-3'<br>The CAT sequence (reverse-complement = ATG) underlined within the _CATT_ module-specific nucleotides, specifies the translation initiation codon for the CDS of interest, while the final T (not underlined) represents the base immediately upstream of the initiation codon. |
| [AATG]-CDS-[GCTT] | Forward | 5'-cgatgtacgtctcaCTCGAATG (SEQ ID NO: 121) (+18-25 bases specific for the 5' end of the CDS, beginning at the 2$^{nd}$ codon)-3'<br>The ATG sequence (underlined within the AATG module-specific nucleotides) specifies the translation initiation codon for the CDS of interest, while the initial A (not underlined) represents the base immediately upstream of the initiation codon. |

TABLE 12-continued

Generalised primer design for amplification of ProUTR, CDS and UTRterm modules to be cloned into pML1.

| TUM | Primer | Primer sequence (5' to 3') |
|---|---|---|
| | Reverse | 5'-gacctttcgtctctGTCTca*AAGC** (SEQ ID NO: 122) (+18-25 bases specific for the 3' end of the CDS)-3'<br>Remember to include a stop codon (*) at the end of the CDS. |
| [GCTT]-<br>UTRterm-<br>[*CGCT*] | Forward | 5'-cgatgtacgtctcaCTCGGCTT (SEQ ID NO: 123) (+18-25 bases specific for the 5' end of the 3'UTR)-3' |
| | Reverse | 5'-gacctttcgtctctGTCTca*AGCG* (SEQ ID NO: 124) (+18-25 bases specific for the 3' end of the terminator)-3' |

Generalised features of forward and reverse PCR primers used for amplification of TUMs are listed. The BsmBI recognition sites are shown in lower case bold (cgtctc), with the overhangs generated following BsmBI cleavage shown by upper case italics (e.g., CTCG). The 5' and 3' nucleotide-specific bases, which flank each TUM and form the basis of the address system for each of the MIDAS modules, are shown in upper case bold (e.g., GGAG) and upper case bold italics (e.g., CATT), respectively.

TABLE 13

Level-3 multigene assemblies are constructed by alternating Golden Gate cloning reactions using TUs assembled in "White" and "Blue" pML2 vectors.

| Step | Level-2 entry clone | Destination plasmid | Golden Gate reaction | Product plasmid | Screen |
|---|---|---|---|---|---|
| 1 | TU1 in a White pML2 vector | pML3 | AarI-mediated | pML3:TU1 | White colonies |
| 2 | TU2 in a Blue pML2 vector | pML3:TU1 | BsmBI-mediated | pML3:TU1:TU2 | Blue colonies |
| 3 | TU3 in a White pML2 vector | pML3:TU1:TU2 | AarI-mediated | pML3:TU1:TU2:TU3 | White colonies |
| 4 | TU4 in a Blue pML2 vector | pML3:TU1:TU2:TU3 | BsmBI-mediated | pML3:TU1:TU2:TU3:TU4 | Blue colonies |

The table shows the cloning steps used to produce a hypothetical multigene construct containing four TUs, with each row depicting the input plasmids (Level-2 entry clone and destination plasmid), the type of Golden Gate reaction used for assembly, the product plasmid and the type of colonies screened.

TABLE 14

Multistep acetonitrile gradient used for LC-MS analysis of fungal extracts.

| Time (minutes) | % (v/v) of acetonitrile + 0.01% (v/v) formic acid |
|---|---|
| 0 | 50 |
| 1 | 50 |
| 15 | 70 |
| 20 | 95 |
| 25 | 95 |
| 28 | 50 |
| 38 | 50 |

REFERENCES (1) Nakazawa, J.; Yajima, J.; Usui, T.; Ueki, M.; Takatsuki, A.; Imoto, M.; Toyoshima, Y. Y.; Osada, H. *Chem. Biol.* 2003, 10 (2), 131-137.

(2) Sallam, A. A.; Ayoub, N. M.; Foudah, A. I.; Gissendanner, C. R.; Meyer, S. A.; El Sayed, K. A. *Eur. J. Med. Chem.* 2013, 70, 594-606.

(3) Byrd, A. D.; Schardl, C. L.; Songlin, P. J.; Mogen, K. L.; Siegel, M. R. *Curr. Genet.* 1990, 18 (4), 347-354.

(4) Yelton, M. M.; Hamer, J. E.; Timberlake, W. E. *Proc. Natl. Acad. Sci.* 1984, 81 (5), 1470-1474.

(5) Vollmer, S. J.; Yanofsky, C. *Proc. Natl. Acad. Sci.* 1986, 83 (13), 4869-4873.

(6) Oliver, R. P.; Roberts, I. N.; Harling, R.; Kenyon, L.; Punt, P. J.; Dingemanse, M. A.; van den Hondel, C. A. M. J. J. *Curr. Genet.* 1987, 12 (3), 231-233.

What we claim is:

1. An isolated polynucleotide comprising at least 70% nucleic acid sequence identity to the nucleic acid sequence of SEQ ID NO: 5 or 20 wherein the polynucleotide encodes a polypeptide of SEQ ID NO: 6 or SEQ ID NO: 21 respectively, and wherein each polypeptide has P450 oxygenase activity.

2. A transcription unit (TU) comprising an isolated polynucleotide of claim 1 and a heterologous regulatory element.

3. An isolated recombinant host cell comprising an isolated polynucleotide of claim 1 or a TU of claim 2.

4. A method of making at least one Nodulisporic Acid (NA) comprising heterologously expressing in an isolated recombinant host cell, a polynucleotide comprising at least 70% nucleic acid sequence identity to SEQ ID NO: 5 or SEQ ID NO: 20, wherein the polynucleotide encodes a polypeptide of SEQ ID NO: 6 or SEQ ID NO: 21 respectively, and wherein each polypeptide has P450 oxygenase activity.

5. An isolated polynucleotide of claim 1 comprising at least 75% nucleic acid sequence identity to SEQ ID NO: 5 or SEQ ID NO: 20.

6. The isolated polynucleotide of claim 1 comprising at least 80% nucleic acid sequence identity to SEQ ID NO: 5 or SEQ ID NO: 20.

7. The isolated polynucleotide of claim 1 comprising at least 85% nucleic acid sequence identity to SEQ ID NO: 5 or SEQ ID NO: 20.

8. The isolated polynucleotide of claim 1 comprising at least 90% nucleic acid sequence identity to SEQ ID NO: 5 or SEQ ID NO: 20.

9. The isolated polynucleotide of claim 1 comprising at least 95% nucleic acid sequence identity to SEQ ID NO: 5 or SEQ ID NO: 20.

10. The isolated polynucleotide of claim 1 comprising at least 99% nucleic acid sequence identity to SEQ ID NO: 5 or SEQ ID NO: 20.

11. The isolated polynucleotide of claim 1 comprising the nucleic acid sequence of SEQ ID NO: 5 or SEQ ID NO: 20.

12. The isolated recombinant host cell of claim 3, wherein the host cell is *Penicillium paxilli*.

13. The isolated recombinant host cell of claim 3, wherein the host cell is *Hypoxylon pulicicidum*.

* * * * *

SEQUENCE LISTING

```
Sequence total quantity: 56
SEQ ID NO: 1               moltype = DNA   length = 1825
FEATURE                    Location/Qualifiers
source                     1..1825
                           mol_type = genomic DNA
                           organism = Hypoxylon pulicicidum
SEQUENCE: 1
ttatgcccag atatttccag cccggggttc gaaaacaaga gaaaacgctg gtatatgaat    60
tatatagcaa tcgtatgctg gcgcagaggc ttcatggctc atcggccgcc caggcagaag   120
tctcagattg aatcttgaca ttatagagga aattaccata cgcatctcca tcatcgcgaa   180
aggtttaccg aggcatccgt acacacccac agagaaaggg atgaatgcat ctgggttgag   240
agtcaagtgt gattggctcg tccatcgctc cgggatgaac tcatctggcc tgacgaaatt   300
tctcttatct aaagacggca gagttaaaat taagctcaaa ggatgactgt atcgaatcga   360
tactaacccc tgtgtatcgt gtaagtgggc atggatacga gcatatgctc tggtataaac   420
tggccatcaa ggatcactcc accaggaccg gtctcccgcc tgcgagccgc catcactgct   480
ggatataaac ggagtgcttc gttgatgcaa ctgttgaggt aaggcatatt gactagggtg   540
gaggttggca taggcagtcc acctatattc atgtcatcaa cctcttttg aagaattgcc    600
tgcttgtctg gatgggttgc cagaagaaac aagatgcag taagggtcga tgctgtagag    660
tcgctaccgg ccacgacagc cagctcagaa tcatagacga ggtcatccg atctttagac    720
tcgtcgtcta agagatggct gaatagatcg tgagtcatag ttggattctc cactgtgcgt   780
cagtcaggta tcctgattag tatgtaatta agtattacct acttgcttcc tttccactac    840
ctcctgtgag caccactgta gccaacttgt tgccttggac tcaagaacg gtagattgcg     900
gagaaggatc aacgtccaag gcgcccacag aagtaaccc cctagttgct tgacagacct    960
cagttgcgtg aagccgggat gcgaaaggcc tttttgaatc atgttgaagg cctttccaaa   1020
tacaagccaa cccattgatt caaatgtgac tctttgcatc aattcagtta cttctaccgg   1080
ttgacctcct ctagatgaga gatagcccat gagttcttgg caacattgcc ggacatggcc   1140
ttcatgagct agcatagctg tatgctctat cagcatgaat cgcccacgcc agggttgtgt   1200
gatactcacc attaggactg aaggccttt gccaaatttt cttccgtcgg aggtggaaat    1260
tcctgtccct tgtcatttga agggacttgt gggataatt cacgtcgtag aatgacccc    1320
tggcacactt ggccaaatcg cgaatggcat tgaagttgtt gacggatatc tcacgaggcc   1380
ctgacacata gtctatcaac ttcgagttta tggcagagtt ggaaataggc tagaacttac   1440
taattcggac gaaatcgtca tagacactat tgcatattctg tacttcaagg tgccattttc   1500
tatctacggc tgctgttttc atccatctca acgtgctcag cctggcggat accttgccgg   1560
ggaaatctct taagggatgc agaaacaacc gatatataat gattgaaaga cagatagaag   1620
agatatagca tagccaaact tggatgaaca taaaagtgat cccatataat cccactgcca   1680
acaacgagca tatgagcgca atggggcaag taatgaagca atggaacagg accggggcgt   1740
gcttgtccca ctctcctcgg atgaataaaa tagtatgaga taggacggct gccaggcaac   1800
tgatgcctaa aatagctaaa gtcat                                         1825

SEQ ID NO: 2               moltype = DNA   length = 1599
FEATURE                    Location/Qualifiers
source                     1..1599
                           mol_type = genomic DNA
                           organism = Hypoxylon pulicicidum
SEQUENCE: 2
ttatgcccag atatttccag cccggggttc gaaaacaaga gaaaacgctg gtatatgaat    60
tatatagcaa tcgtatgctg gcgcagaggc ttcatggctc atcggccgcc caggcagaag   120
tctcagattg aatcttgaca ttatagagga aattaccata cgcatctcca tcatcgcgaa   180
aggtttaccg aggcatccgt acacacccac agagaaaggg atgaatgcat ctgggttgag   240
agtcaagtgt gattggctcg tccatcgctc cgggatgaac tcatctggcc tgacgaaatt   300
tctcttatcc ctgtgtatcg tgtaagtggg catggatacg agcatatgct ctggtataaa   360
ctggccatca aggatcactc caccaggacc ggtctcccgc tgcgagccgc tcatcactgc   420
tggatataaa cggagtgctt cgttgatgca actgttgagg taaggcatat tgactagggt   480
ggaggttggc ataggcagtc cacctatatt catgtcatca acctcttttt gaagaattgc   540
ctgcttgtct ggatgggttg ccagaagaaa caagatgca gtaagggtcg atgctgtaga   600
gtcgctaccg gccacgacag ccagctcaga atcatagacg aggtcatccg tatctttaga   660
ctcgtcgtct aagagatggc tgaatagatc gtgagtcata ttggattttt gcttcctttc   720
cactacctcc tgtgagcacc actgtagcca acttgttgcc ttggacctca agaacgtag    780
attgcggaga aggatcaacg tccaaggcgc cacagaagt aacccccta gttgcttgac    840
agacctcagt tgcgtgaagc cgggatgcga aaggcctttt tgaatcatgt tgaaggcctt   900
tccaaataca agccaaccca ttgattcaaa tgtgactctt tgcatcaatt cagttacttc   960
taccggttga cctcctctag atgagagata gcccatgagt tcttggcaac attgccggac  1020
atggccttca tgagctagca tagcattagg actgaaggcc ttttgccaaa ttttcttccg  1080
tcggaggtgg aaattcctgt cccttgtcat ttgaaggac ttgtgggat aattcacgtc    1140
gtagaatgga cccctggcac acttggccaa atcgcgaatg gcattgaagt tgttgacgga  1200
tatctcacga ggcctaattc ggacgaaatc gccatagaca ctatgcatat tctgtacttc  1260
aaggtgccat tttctatcta cggctgctgt tttcatccat ctcaacgtgc tcagcctggc  1320
ggataccttg ccgggaaat ctcttaaggg atgcagaaac aaccgatata taatgattga    1380
aagacagata gaagagatat agccaaactt ggatgaaaca aacataaaag tgatcccata   1440
taatcccact gccaacaacg agcatatgag cgcaatgggg caagtaatga agcaatggaa   1500
caggaccggg gcgtgcttgt cccactctcc tcgatgaat aaaatagtat gatagggac    1560
ggctgccagg caactgatgc ctaaaatagc taaagtcat                          1599

SEQ ID NO: 3               moltype = AA    length = 532
FEATURE                    Location/Qualifiers
source                     1..532
                           mol_type = protein
                           organism = Hypoxylon pulicicidum
```

-continued

```
SEQUENCE: 3
MTLAILGISC  LAAVLSHTIL  FIRGEWDKHA  PVLFHCFITC  PIALICSLLA  VGLYGITFMF   60
IQVWLCYISS  ICLSIIIYRL  FLHPLRDFPG  KVSARLSTLR  WMKTAAVDRK  WHLEVQNMHS  120
VYGDFVRIRP  REISVNNFNA  IRDLAKCARG  PFYDVNYPHK  SLQMTRDRNF  HLRRKKIWQK  180
AFSPNAMLAH  EGHVRQCCQE  LMGYLSSRGG  QPVEVTELMQ  RVTFESMGWL  VFGKAFNMIQ  240
KGLSHPGFTQ  LRSVKQLGGL  LLWAPWTLIL  LRNLPFLRSK  ATSWLQWCSQ  EVVERKQNPT  300
MTHDLFSHLL  DDESKDTDDL  VYDSELAVVA  GSDSTASTLT  AILFLLATHP  DKQAILQKEV  360
DDMNIGGLPM  PTSTLVNMPY  LNSCINEALR  LYPAVMSGSQ  RETGPGGVIL  DGQFIPEHML  420
VSMPTYTIHR  DKRNFVRPDE  FIPERWTSQS  HLTLNPDAFI  PFSVGVYGCL  GKPFAMMEMR  480
MVISSIMSRF  NLRLLPGRPM  SHEASAPAYD  CYIIHIPAFS  LVFEPRAGNI  WA          532

SEQ ID NO: 4              moltype = DNA  length = 1826
FEATURE                   Location/Qualifiers
source                    1..1826
                          mol_type = genomic DNA
                          organism = Hypoxylon pulicicidum
SEQUENCE: 4
atgtttgata ttgattttgg cattctattt ccaatttcct gggaacaatc ccctatcttt   60
ctggctgttg ggctaatatt cgcatttgcg accttatctc cgtggctccg ttccggggaa  120
cgcctgatca atggtcgcga aggcttcgaa atactgtgga cgaatgcgaa gaagcgatat  180
caaacgaagg ggcgatctgt tatggaggca ggcttttcaa aggtaggata catcattgtc  240
tccaaatgaa agacattcaaa tcgtgccggg tcatatgtgc tgatacttgg agatagtaca  300
acgattcttt ctacatgatg acggatagtg gtaccgaaat ggtcctacac ccgagatacg  360
tcgacgagat ccggaacgac ccaaggttgg actttcacag atatatgaaa actgtaaatag  420
aattcgatcc attttctata tatccgggct gacgtctacg tacgcgaggt cctacatggg  480
ctcagacaga aagtggcga gataaaccga gatcttatcc aaaccaaatt gactagatct  540
gtgggtaagg ggttgtcgtc tctagagaa tgcaggcaaa gggaaggaca agagtaaact  600
aatgcccatc cttgtatagg taggctcatt ggtccatat cggctgaaat cgaggacgcc  660
cttcacaatc gatgggaaga aggcgaaggt gaatatgaag agtaccttct agtgcttccc  720
cctgctgaaa tgcatacaga atggcatgag attgtattgc tctccgtaat gatcccggtt  780
gttgcgcaag gagtatccaa aatgtttgtc ggagatccat tgtgccgtaa caaggattgg  840
ataggtatga tcttaaggca tacaaggagt gtccagacag cactgcggtc ccttcgattg  900
tggccttact ttcttagacc acttgcagcc agatttctgc caacctgtcg acaagtcact  960
gcagaaatag aagaggccag cgcatcatc aatccagtac ttgagaagaa gcgtgccgag 1020
aagctcgcaa tgattcagaa gggagaaaaa cctccagagc ccaacaccta catggattgg 1080
ttagaagaat ccgacaagga tgaattctat gacccagttg ttgctcagct gaagatttcc 1140
atggcagcta tacacgctac ctcggacctc ttatcgcaga caatttttcag cctatgtgac 1200
agcccagagc tagtcaagga actgcagacc gaagctgtgt ctgttatag agcgtacggc 1260
tgggggaagg aagcaatcta caacctgaag tgatggaca ggtcctgaa agagacgcaa 1320
cgcctaaaaac ctatgcaaat cagtaagcgc cggtgccgcc gtgtggactt gctatcgcta 1380
atcgctttgc ctttgcttgc tctctagact tgacgcgact agctctagat cgcataaaac 1440
tttccgatgg cacggttatc cctagggcct ccaaagttct tatctcctgc acaacatgt 1500
gggattcgaa cgtctacccc aacgcaaacc agtatgacgg tcatcgcttc tataaactc 1560
ggcagcgcgc tggaatggag aattccgcac agctatcaac cctagtccg gatcatctgg 1620
gcttcggact gggaatgtat gcctgtcccg gtaggcatat cgcatcgacc gttatgaaag 1680
tcacactatg ccatatcctc ctgaagtatg acttcgaatt ggcggagggc tgcaccccta 1740
gagtgattga atatggtagt ttcttgttag ctgatccaac ggcgagagtt tctatcagac 1800
ggcggaaaga agagattcaa ctgtaa                                        1826

SEQ ID NO: 5              moltype = DNA  length = 1536
FEATURE                   Location/Qualifiers
source                    1..1536
                          mol_type = genomic DNA
                          organism = Hypoxylon pulicicidum
SEQUENCE: 5
atgtttgata ttgattttgg cattctattt ccaatttcct gggaacaatc ccctatcttt   60
ctggctgttg ggctaatatt cgcatttgcg accttatctc cgtggctccg ttccggggaa  120
cgcctgatca atggtcgcga aggcttcgaa atactgtgga cgaatgcgaa gaagcgatat  180
caaacgaagg ggcgatctgt tatggaggca ggcttttcaa agtacaacga ttctttctac  240
atgatgacgg atagtggtac cgaaatggtc ctacaccga gatacgtcga cgagatccgg  300
aacgacccaa ggttggactt tcacagatat atgaaaacta aggtggcga gataaaccga  360
gatcttatcc aaaccaaatt gactagatct gtgggtaggc tcattgggtc catatcggct  420
gaaatcgagg acgcccttca caatcgatgg aagaaggcg aagtgaata tgaagagtac  480
cttctagtgc ttcccctgc tgaaatgcat acagaatgg atgagattgt attgctcctcc  540
gtaatgatcc cggttgttgc gcaaggagta tccaaatgtt tgtcggaga tccattgtgc  600
cgtaacaagg attggatagg tatgatctta aggcatacaa ggagtgtcca gacagcactg  660
cggtcccttc gattgtggcc tactttctt agaccacttg cagccagatt tctgccaacc  720
tgtcgacaag tcactgcaga aatagaagag gccaggcgca tcatcaatcc agtacttgag  780
aagagcgtg ccgagaagct cgcaatgatt cagaaggag aaaaacctcc agagcccaac  840
acctacatgg attggttaga agaatccgac aaggatgaat ctatgacc agttgttgct  900
cagctgaaga tttccatggc agctatacac gctacctcgg acctcttatc gcagacaatt  960
ttcagcctat gtgacagccc agagctagtc aaggaactgc agccgaagc tgtgtctgtt 1020
ataggagcgt acggctgggg gaaggaagca atctacaacc tgaagctgat ggacagcgtc 1080
gaaaggaga cgcaacgcct aaaaacctat gcaaatcagt aagcgccgg tgccgccgtg 1140
cgcataaaac tttccgatgg cacggttatc cctagggct ccaaagttct tatctcctgc 1200
cacaacatgt gggattcgaa cgtctacccc aacgcaaacc agtatgacgg tcatcgcttc 1260
tataaacttc ggcagcgcgc tggaatggag aattccgcac agctatcaac cctagtccg 1320
gatcatctgg gcttcggact gggaatgtat gcctgtcccg gtaggcatat cgcatcgacc 1380
gttatgaaag tcacactatg ccatatcctc ctgaagtatg acttcgaatt ggcggagggc 1440
```

```
tgcacccta gagtgattga atatggtagt ttcttgttag ctgatccaac ggcgagagtt    1500
tctatcagac ggcggaaaga agagattcaa ctgtaa                             1536
```

SEQ ID NO: 6          moltype = AA   length = 511
FEATURE               Location/Qualifiers
source                1..511
                      mol_type = protein
                      organism = Hypoxylon pulicicidum
SEQUENCE: 6
```
MFDIDFGILF PISWEQSPIF LAVGLIFAFA TLSPWLRSGE RLINGREGFE ILWTNAKKRY    60
QTKGRSVMEA GFSKYNDSFY MMTDSGTEMV LHPRYVDEIR NDPRLDFHRY MKTKGGEINR   120
DLIQTKLTRS VGRLIGSISA EIEDALHNRW EEGEGEYEEY LLVLPPAEMH TEWHEIVLLS   180
VMIPVVAQGV SKMFVGDPLC RNKDWIGMIL RHTRSVQTAL RSLRLWPYFL RPLAARFLPT   240
CRQVTAEIEE ARRIINPVLE KKRAEKLAMI QKGEKPPEPN TYMDWLEESD KDEFYDPVVA   300
QLKISMAAIH ATSDLLSQTI FSLCDSPELV KELRAEAVSV IGAYGWGKEA IYNLKLMDSV   360
LKETQRLKPM QINLTRLALD RIKLSDGTVI PRGSKVLISC HNMWDSNVYP NANQYDGHRF   420
YKLRQRAGME NSAQLSTPSP DHLGFGLGMY ACPGRHIAST VMKVTLCHIL LKYDFELAEG   480
CTPRVIEYGS FLLADPTARV SIRRRKEEIQ L                                  511
```

SEQ ID NO: 7          moltype = DNA   length = 2012
FEATURE               Location/Qualifiers
source                1..2012
                      mol_type = genomic DNA
                      organism = Hypoxylon pulicicidum
SEQUENCE: 7
```
ctaatctgcg atggaccctg accctaaccc tgaccctgac ctgaatccgg acccctgctc    60
atcctcgtct ctcacaatct cacgggtcgtag atctgccggc caagttggcg catcgactcc   120
gttccctctc gtgcccacat tatacttgag ttcaatcgcg tcgtccttga atcgagcgat   180
aggccttact tgtatgaacg tcgtgttcaa cgcgccggac cggaatgggc cgaaaaattc   240
cctttgaaag agaatctcgc cgtcgaattt gtacaatgcc gttagcagct taggcagcat   300
gtattgcatg gagtggtagt gtctgaaaac aggtgcgtcg tgacggcgga acaggtcagt   360
ccaggtatgc tcgtcgtatg tcccgactga tcgaacaagc cattgattgt aatagttgat   420
tgatacctga aatactgta tgagcgataa ccagcgatag cgtatccggg ggctacctac   480
atcaaccctg tagcttcccc cttttctcggc tctttggaca agggcgtcca agacagccgt   540
ggacccgcat attccggtac tagaagatat gtcagtcagg ctgcaactct gctaccaagt   600
gaagaggtat ctctcgatcg gctcaccaat aatcagaatt gaacagagca ggagttacag   660
gctcttcaag acccatagca tggccgtacg aagtagaaat cccgcagcac gcatcgctaa   720
tctgctgcca gccgcttcta tggctccagg gtccatacca accatagcag ttctccctga   780
cgtaaataat accacgactg cggtcccgca ccagattgaa caccctcgtcg tagccaaagc   840
caaaacgttt catcacacct ggccgatagc tatctacaac cacatctgca tccaatatca   900
agtccctcag cttttggcgg tcagattcga catccaaccg tagccatgag ttccatttgc   960
cccaattcaa gtcttggtgt aacaccgaca tgtccgtgat gtctgggaa gtaacacgca   1020
ttacactagc ccccatctcc gcaagacttc tgtgttatcg tggacccgct atagcgcgcg   1080
ttaagtccac caccttcagc ccggccagcg gtctcttggg gctcgatgga gcgttaggat   1140
gatcaggcca ccaggctgct ggctgagaag aatttgggtc tctaatgacc tcatacagtc   1200
ccaccttgcc attttttctgg ccgtgctcgc tggcaaagta ctcagcggag ctgtagacaa   1260
tggtaccggc ttggcgatgt tcttcattta gcaaatgtgt tatgtgtgtg gcgtcatact   1320
ttgagagtct ttgttggatc ctgtcggtta cgacctcaga agtgtcttga acctcgcctt   1380
cgacgggcaa cctaggtgcc tgtagggtgg gctctggatt cattccccct ggaggaatat   1440
cgattagtct ctagattgac tcggcttgca agatcatacc gtgtgtatgg tagaaacggc   1500
catccttttgt tttatagata ttggtaatca atgcccgttg tagagatgcg ttggcgcgat   1560
gtttatctcg gttcggaaaa agttctgctg tcagtgtatc aaatggcgag aaaggacgga   1620
cttctcctct atcctcgatt tgggtgagca tgggggacat gaggaacaag gttcgtggt    1680
ctctatctga tgttagacaa acggccagtg cttcatatac atcacaatcc gagaacttac   1740
gtgttttattg agacattgct agggcgtaca ccatatttcc gatgggccag ataattcagg   1800
aacgttgctt caaaggcttt caaagctgag atgctctctg cgagcctcca gttaacagga   1860
atgctaggct tgacgttcc ctcgaaggag acaaatttgg cgatttcggc cagctcaggg    1920
ggaagatttg gcattagcgg attctctaga atttcgcgta tgaatacaga ttccgcttgc   1980
ttgggaactg tattatccgc acttgactcc at                                 2012
```

SEQ ID NO: 8          moltype = DNA   length = 1782
FEATURE               Location/Qualifiers
source                1..1782
                      mol_type = genomic DNA
                      organism = Hypoxylon pulicicidum
SEQUENCE: 8
```
ctaatctgcg atggaccctg accctaaccc tgaccctgac ctgaatccgg acccctgctc    60
atcctcgtct ctcacaatct cacggcgtag atctgccggc caagttggcg catcgactcc   120
gttccctctc gtgcccacat tatacttgag ttcaatcgcg tcgtccttga atcgagcgat   180
aggccttact tgtatgaacg tcgtgttcaa cgcgccggac cggaatgggc cgaaaaattc   240
cctttgaaag agaatctcgc cgtcgaattt gtacaatgcc gttagcagct taggcagcat   300
gtattgcatg gagtggtagt gtctgaaaac aggtgcgtcg tgacggcgga acaggtcagt   360
ccaggtatgc tcgtcgtatg tcccgactga tcgaacaagc cattgattgt aatagttgat   420
tgatacctga aatactgta ttccccctctt tcggcgtctt tggacaaggg cgtccaagac   480
agccgtggac ccgcatattc cggtacaata atcagaattg aacagagcag gagttacagg   540
ctcttcaaga cccatagcat ggccgtacga agtagaaatc ccgcagcacg catcgctaat   600
ctgctgccag ccgcttctat ggctccaggg tccatacaa ccatagcagt tctccctgac    660
gtaaataata ccacgactgc ggtcccgcac cagattgaac cctcgtcgt agccaaagcc    720
aaaacgtttt catcacacctg gccgatagct atctacaacc acatctgcat ccaatatcaa   780
```

```
gtccctcagc tttttggcggt cagattcgac atccaaccgt agccatgagt tccatttgcc    840
ccaattcaag tcttggtgta acaccgacat gtccgtgatg tctgggaag  taacacgcat    900
tacactagcc cccatctccg caagacttcg tgttatcgtc ggacccgcta tagcgcgcgt    960
taagtccacc accttcagcc cggccagcgg tctcttgggg ctcgatggag cgttaggatg   1020
atcaggccac caggctgctg gctgaggaag atttgggtct ctaatgacct catacagtcg   1080
caccttgcca ttttctggc  cgtgctcgct ggcaaagtac tcagcggagc tgtagacaat   1140
ggtaccggct tggcgatgtt cttcattag  caaatggtct agatgtgtgg cgtcatactt   1200
tgagagtctt tgttggatcc tgtcggttac gaccctcagaa gtgtcttgaa cctcgccttc   1260
gacgggcaac cctagtgcct gtagggtggg ctctggattc attccccgt  gtgtatgcgt   1320
gaaacggcca tcctttgttt tatagatatt ggtaatcaat gcccgttgta gagatgcgtt   1380
ggcgcgatgt ttatctcggt tcggaaaaag ttctgctgtc agtgtatcaa atggcgagaa   1440
aggacggact tctcctctat cctcgatttg ggtgagcatg ggggacatga ggaacaaggt   1500
tgcgtggtct gtgtttattg agacattgct agggcgtaca ccatacttcc gatgggccag   1560
ataattcagg aacgttgctt caaagctttt caaagctgag atgctctctg cgagcctcca   1620
gttaacagga atgctaggct tgacgtttcc ctcgaaggac acaaatttgg cgatttcggc   1680
cagctcaggg ggaagatttg gcattagcgg attctctaga atttcgcgta tgaatacaga   1740
ttccgcttgc ttgggaactg tattatccgc acttgactcc at                      1782

SEQ ID NO: 9         moltype = AA   length = 593
FEATURE              Location/Qualifiers
source               1..593
                     mol_type = protein
                     organism = Hypoxylon pulicicidum
SEQUENCE: 9
MESSADNTVP KQAESVFIRE ILENPLMPNL PPELAEIAKF VSFEGNVKPS IPVNWRLAES     60
ISALKAFEAT FLNYLAHRKY GVRPSNVSIN TDHATLFLMS PMLTQIEDRG EVRPFSPFDT    120
LTAELFPNRD KHRANASLQR ALITNIYKTK DGRFYHTHGG MNPEPTLQAL GLPVEGEVQD    180
TSEVVTDRIQ QRLSKYDATH LDHLLNEEHR QAGTIVYSSA EYFASEHGQK NGKVGLYEVI    240
RDPNSSQPAA WWPDHPNAPS SPKRPLAGLK VVDLTRAIAG PTITRSLAEM GASVMRVTSP    300
DITDMSVLHQ DLNWGKWNSW LRLDVESDRQ KLRDLILDAD VVVDSYRPGV MKRFGFGYDE    360
VFNLVRDRSR GIIYVRENCY GWYGPWSHRS GWQQISDACC GISTSYGHAM GLEEPVTPAL    420
FNSDYCTGIC GSTAVLDALV QRAEKGGSYR VDVSINYYNQ WLVRSVGTYD EHTWTDLFRR    480
HDAPVFRHYH SMQYMLPKLL TALYKFDGEI LFQREFFGPF RSGALNTTFI QVRPIARFKD    540
DAIELKYNVG TRGNGVDAPT WPADLRREIV RDEDEQGSGF RSGSGLGSGS IAD           593

SEQ ID NO: 10        moltype = DNA   length = 1577
FEATURE              Location/Qualifiers
source               1..1577
                     mol_type = genomic DNA
                     organism = Hypoxylon pulicicidum
SEQUENCE: 10
atgtctaccc ctgagttcaa ggtgataatc gttggcggct cccttgcggg tctaacattg     60
gcccattgcc tcctccgcgc cggaatttcc cacatcgttc ttgagagacg tagtgtaatc    120
gcaccagagg aaggtgcctc aatagggatt cttcctaatg cgctcgtgt  cttggatcaa    180
ctaggcatct atgaacatat tcaagacact actgagccat tgagtacagc tcatatacga    240
tatccagatg ggttctattt cagcagtcgc tatcccgaga tcataaaaga aaggtgagca    300
ctcccatgaa catatgccta tcgtttgcgc aatggctgcc agcatggc   ccgttcgtag    360
gtttgggtat ccgatagcct ttttaccccg gaggagactt ttggagattc tctatacatc    420
gtaccctgac cattctaaca tctataccaa caagaatgtg atcaaggtgc aaagccatga    480
taatcaagtt tctgtcttga cagaggatgg aaatacatat cgaggggatc ttgtggtggg    540
cgccgacggt gtcaacagtc gagttctatc tgaaattttag aaattagcag gtaatccctc    600
tctcacgaaa cgggaaggaa gaggtcagtc gagatcttat aatattcgca tagcgactca    660
tacagacgtt gataataaac ttaggaagga ccatcgagta cgcttgtgtg tttgggatat    720
cctcgccaat ctcagacctc aagcccggcg agcaggttaa cgccgttctac gacggactca    780
caatgctcac gatccatggt agaaacggag acatattcgt gtttttatc  aagaaactct    840
cgcgtcgcta tatctatccc gatctcatca gattacagca gaaagacgca gaagggatct    900
gtgaagaagc caagtcacta actgtctgga aaggtgttac attcggtgac atttgggaaa    960
gaagagaaac agcatcattg accgttttgg atgagttctt gcatcacact tggagttggg   1020
acagatcggt ttgtgtgggc gacagtatcc acaaggtata tgcctcctat ggtctgaagc   1080
acattaaggg gttggctaac gctgtcatat agatgactcc aaattttggc caggtgcga    1140
atactgctat cgaggattct gccgctctag ccaatctact gcacagtttg atcaaggaga   1200
aacgagccga aaagccgact gactcagata tatcactgct tctgaggcag ttcaaatcac   1260
agcgtcttcg acgcgttcag aagatatata aaatgtcaag gtttgttacg cggcttcaag   1320
cgcgcgatgg gttgttgaat actcttctgg gacgccatta cgccccatat gcagcagatc   1380
ttccagctaa gattgcctct ggatgcatcg ctggtgcgga agttctggat tacctcccat   1440
tacccaaggt aactggggcg ggctggaata ggggccatcg tagatctacc atgtacatcc   1500
tgctaggatt cacaggggta ttcacctctg tctggcgat  ggtagtgtta ctccatatta   1560
gagacatcgc ttcatag                                                  1577

SEQ ID NO: 11        moltype = DNA   length = 1392
FEATURE              Location/Qualifiers
source               1..1392
                     mol_type = genomic DNA
                     organism = Hypoxylon pulicicidum
SEQUENCE: 11
atgtctaccc ctgagttcaa ggtgataatc gttggcggct cccttgcggg tctaacattg     60
gcccattgcc tcctccgcgc cggaatttcc cacatcgttc ttgagagacg tagtgtaatc    120
gcaccagagg aaggtgcctc aatagggatt cttcctaatg cgctcgtgt  cttggatcaa    180
ctaggcatct atgaacatat tcaagacact actgagccat tgagtacagc tcatatacga    240
```

```
tatccagatg ggttctattt cagcagtcgc tatcccgaga tcataaaaga aaggtttggg    300
tatccgatag cctttttacc ccggaggaga cttttggaga ttctctatac atcgtaccct    360
gaccattcta acatctatac caacaagaat gtgatcaagg tgcaaagcca tgataatcaa    420
gtttctgtct tgacagagga tggaaataca tatcgagggg atcttgtggt gggcgccgac    480
ggtgtcaaca gtcgagttct atctgaaatt tggaaattga caggtaatcc ctctctcacg    540
aaacgggaag gaagaggaag gaccatcgag tacgcttgtg tgtttgggat atcctcgcca    600
atctcagacc tcaagcccgg cgagcaggtt aacgcgttct acgacggact cacaatcgtc    660
acgatccatg gtagaaacgg agagatattc tggttttttta tcaagaaact ctcgcgtcgc    720
tatatctatc ccgatctcat cagattacag cagaaagacg cagaagggat ctgtgaagaa    780
gccaagtcac taactgtctg gaaaggtgtt acattcggtg acatttggga aagaagagaa    840
acagcatcat tgaccgtttt ggatgagttc ttgcatcaca cttggagttg ggacagatcg    900
gtttgtgtgg gcgacagtat ccacaagatg actccaaatt ttggccaggg tgcgaatact    960
gctatcgagg attctgccgc tctagccaat ctactgcaca gtttgatcaa ggagaaacga   1020
gccaaaagc cgactgactc agatatatca ctgcttctga ggcagttcaa atcacagcgt   1080
cttcgacgcg ttcagaagat atataaaatg tcaaggtttg ttacgcggct tcaagcgcgc   1140
gatgggttgt tgaatactct tctgggacgc cattacgccc catatgcagc agatcttcca   1200
gctaagattg cctctggatg catcgctggt gcggaagttc tggattacct cccattaccc   1260
aaggtaactg gggcgggctg gaataggggc catcgtagat ctaccatgta catcctgcta   1320
ggattcacag gggtattcac ctctgctctg gcgatggtag tgttactcca tattagagac   1380
atcgcttcat ag                                                        1392

SEQ ID NO: 12             moltype = AA   length = 463
FEATURE                   Location/Qualifiers
source                    1..463
                          mol_type = protein
                          organism = Hypoxylon pulicicidum
SEQUENCE: 12
MSTPEFKVII VGGSLAGLTL AHCLLRAGIS HIVLERRSVI APEEGASIGI LPNGARVLDQ    60
LGIYEHIQDT TEPLSTAHIR YPDGFYFSSR YPEIIKERFG YPIAFLPRRR LLEILYTSYP   120
DHSNIYTNKN VIKVQSHDNQ VSVLTEDGNT YRGDLVVGAD GVNSRVLSEI WKLAGNPSLT   180
KREGRGRTIE YACVFGISSP ISDLKPGEQV NAFYDGLTIV TIHGRNGEIF WFFIKKLSRR   240
YIYPDLIRLQ QKDAEGICEE AKSLTVWKGV TFGDIWERRE TASLTVLDEF LHHTWSWDRS   300
VCVGDSIHKM TPNFGQGANT AIEDSAALAN LLHSLIKEKR AEKPTDSDIS LLLRQFKSQR   360
LRRVQKIYKM SRFVTRLQAR DGLLNTLLGR HYAPYAADLP AKIASGCIAG AEVLDYLPLP   420
KVTGAGWNRG HRRSTMYILL GFTGVFTSAL AMVVLLHIRD IAS                     463

SEQ ID NO: 13             moltype = DNA   length = 803
FEATURE                   Location/Qualifiers
source                    1..803
                          mol_type = genomic DNA
                          organism = Hypoxylon pulicicidum
SEQUENCE: 13
ttattgagcc ttccgcgcat tgcttcgttc ttggccatgt tcgtatttct tcacattcca     60
cagacaaatt ccatagaggc tgtctaccgc aatgaataca ccgaggctcc atagtaccag    120
aggactattg agccagttga atgcctccga ccagtacatg tacctcaata tggcaaaccc    180
aaccacacaa ccgatcctta aagcgagaa taacctatac cttgttattt atatgtcctc    240
aaagttctgt tgcataactt cggagcaaga agatggatta cctaccataa ggtatatgaa    300
gctccacgac tactacttct ccctagaagc tggcagaacc ccccgacgct agcagtagc    360
tggcaagcca ctgcacccca gaatatccaa gtgctggcc caatctctgc tgctagggct    420
agatggcccc tcaaggagcc caagacacct agtgcgaaaa tgagtgtgat gttgttcatc    480
acaagaggcg catgggccca ttcattcggc gcaaacctga tcgcggtgta catgactccg    540
agattgacta ccagtccagc tagaaacaca ccttgctcga tgcggctttt tgaagggtag    600
ataagaccat ataccatttc ccaagcaaag ttgcagcaaa gagccagcgg tgccatgctg    660
taagtctgtt cctggagcga ggtgtagatc atgccggcgt agtttatgag ccaacaaacg    720
cccattccga agacgaagat gtccgaaatc cattcgacgc gctgatattc aacgggtgca    780
ttggaacgat cgaatccatc cat                                            803

SEQ ID NO: 14             moltype = DNA   length = 732
FEATURE                   Location/Qualifiers
source                    1..732
                          mol_type = genomic DNA
                          organism = Hypoxylon pulicicidum
SEQUENCE: 14
ttattgagcc ttccgcgcat tgcttcgttc ttggccatgt tcgtatttct tcacattcca     60
cagacaaatt ccatagaggc tgtctaccgc aatgaataca ccgaggctcc atagtaccag    120
aggactattg agccagttga atgcctccga ccagtacatg tacctcaata tggcaaaccc    180
aaccacacaa ccgatcctta aagcgagaa taaccataag gtatatgaag ctccacgact    240
actacttctc cctagaagct ggcagaaccc ccgacgctag cagtagctg gcaagccac    300
tgcaccccaa gaatatccaa gtgctggcc aatctctgct gctagggcta gatggcccat    360
caaggagccc aagacaccta gtgcgaaaat gagtgtgatg ttgttcatca agaggcgc    420
atgggcccat tcattcggcg caaacctgat cgcggtgtac atgactccga gattgactac    480
cagtccagct agaaacacac cttgctcgat gcggcttttt gaagggtaga taagaccata    540
taccatttcc aagcaaagt tgcagcaaag agccagcggt gccatgctgt aagtctgttc    600
ctggagcgag gtgtagatca tgccggcgta gtttatgagc caacaaacgc ccattccgaa    660
gacgaagatg tccgaaatca ttcgacgcg ctgatattca acgggtgcat tggaacgatc    720
gaatccatcc at                                                        732

SEQ ID NO: 15             moltype = AA   length = 243
FEATURE                   Location/Qualifiers
```

| source | 1..243 |
| --- | --- |
| | mol_type = protein |
| | organism = Hypoxylon pulicicidum |

SEQUENCE: 15

```
MDGFDRSNAP VEYQRVEWIS DIFVFGMGVC WLINYAGMIY TSLQEQTYSM APLALCCNFA  60
WEMVYGLIYP SKSRIEQGVF LAGLVVNLGV MYTAIRFAPN EWAHAPLVMN NITLIFALGV 120
LGSLTGHLAL AAEIGPALGY SWGAVACQLL LSVGGFCQLL GRSSSRGASY TLWLSRFIGS 180
GCVVGFAILR YMYWSEAFNW LNSPLVLWSL GVFIAVDSLY GICLWNVKKY EHGQERSNAR 240
KAQ                                                             243
```

| SEQ ID NO: 16 | moltype = DNA  length = 1514 |
| --- | --- |
| FEATURE | Location/Qualifiers |
| source | 1..1514 |
| | mol_type = genomic DNA |
| | organism = Hypoxylon pulicicidum |

SEQUENCE: 16

```
atggaggttt cctcaagtga acactcccc  attctatgga gaacgagtcc tccctcaaac   60
gactatgaaa atgcaagatg cagagtgttc aatggcaggc agcctgagca cttcccccctt  120
gcaatagtca aggcaaacaa ggtcgagcat attgtagccg ccgtgaaact ggcagcagaa  180
ctagacgcct gtatcgccgt tcgttcgggc ggccacagcc tctcttgttg gactatacgc  240
catggggcga tccttattga cctcgaagat tatcagcact tgagctatga cgacgagatc  300
catgaagtgc aagcttcacc cagtacactt ggtgcggacc tacttacgtt ccttgcgaag  360
aaaaagaggt tctttcccgt aggtcactct ggagacattg gcttaggtgg ctatctcctt  420
cagggcggaa ttgggctcaa ttctcgggta tgaacgttga ccctacatac tcagtagctt  480
tcgaatactg acgatatctc tagggatatg gtatgcctg  tgaatacatt accgggcttg  540
atatcatcac cgctgatgat gaaatcaagc atttgtgataa gacggaaaac tctgacctat  600
actgggctgc tcgtggagct ggaccgggta agttcctcaa agctgtctgt accagtgtgt  660
aagagttcta ataaagcaga attccctgca atcgttatac ggtcttcct  gaagacgtgc  720
ccctcttgc cggtgtgtaa gcggagtaga tacgtctggc cggcggccat gtatgggaag  780
gttttaagt ggcttgaaga ggtaagttta atcccaagga tctaggacgg cagggttaa   840
tctgatccgc gtcttacag ctattgaatt ccttgagcga ggacgtcgag attgccgttt  900
tcggggtttgt attgccccga ctcaaccagc caggcttagt cctccatgca acagcatttg  960
gtgactctag cgagaatgtc cgggaaaagc tcacgcctat catcaaaaat catcctccag 1020
ggacttttcttggctgaagat ttcgtgagca ccaacttccc cgaagactac gacttaggta 1080
aggataccat gccgcgggc  gctcgctatt ttaccgacag cgtctttctc aagcccggta 1140
tcgacttcgt cgcaacctgc aaaggaatgt ttacggagct caaacatccc cgtgcattgg 1200
cgtactggca accgatgaag accaatattg atcgcatcct tccgatatg  gcgatgagca 1260
tccatagtca tcattacgtg tcactacttg ccatctatga gaccccagt  gaggaccaac 1320
agcaaatatc ctggatcata gatcgtatga aagtcttga gccggcaatc ctgggaactt 1380
tcataggga  tgcacaccca gtggaaaggc catctaatta ttggtccgag gaagctgaag 1440
aacgggtgat cactattggg cggaagtggg accctagtag tagaattcgg ggtattgtgt 1500
tgagcgatgc ctaa                                                 1514
```

| SEQ ID NO: 17 | moltype = DNA  length = 1347 |
| --- | --- |
| FEATURE | Location/Qualifiers |
| source | 1..1347 |
| | mol_type = genomic DNA |
| | organism = Hypoxylon pulicicidum |

SEQUENCE: 17

```
atggaggttt cctcaagtga acactcccc  attctatgga gaacgagtcc tccctcaaac   60
gactatgaaa atgcaagatg cagagtgttc aatggcaggc agcctgagca cttcccccctt  120
gcaatagtca aggcaaacaa ggtcgagcat attgtagccg ccgtgaaact ggcagcagaa  180
ctagacgcct gtatcgccgt tcgttcgggc ggccacagcc tctcttgttg gactatacgc  240
catggggcga tccttattga cctcgaagat tatcagcact tgagctatga cgacgagatc  300
catgaagtgc aagcttcacc cagtacactt ggtgcggacc tacttacgtt ccttgcgaag  360
aaaaagaggt tctttcccgt aggtcactct ggagacattg gcttaggtgg ctatctcctt  420
cagggcggaa ttgggctcaa ttctcgggga tatgggtatg cctgtgaata cattaccggg  480
cttgatatca tcaccgctga tggtgaaatc aagcattgtg ataagacgga aaactctgac  540
ctatactggg ctgctcgtgg agctggaccg gaattccctg caatcgttat acggttcttc  600
ctgaagacgt gcccctcttt gccggtgtgt aagcggagta gatacgtctg gccggcggta  660
atgtatggga aggtttttaa gtggcttgaa gagctattga attccttgag cgaggacgtc  720
gagattgccg ttttcgggtt tgtattgccc gactcaacc  agccaggctt agtcctccat  780
gcaacagcat ttggtgactc tagcgagaat gtccgggaaa agctcacgcc tatcatcaaa  840
aatcatcctc caggggactttt cttggctgaa gatttcgtga gcaccaactt ccccgaagac  900
tacgacttag gtaaggatac catgccgcgc ggcgctcgct attttaccga cagcgtcttt  960
ctcaagcccg gtatcgactt cgtcgcaacc tgcaaaggaa tgtttacgga gctcaaacat 1020
ccccgtgcat tggcgtactg gcaaccgatg aagaccaata ttgatcgcat ccttcccgat 1080
atggcgatga gcatccatag tcatcattac gtgtcactac ttgccatcta tgaagacccc 1140
agtgaggacc aacagcaaat atcctggatc atagatcgta tgaaagtctt gagccgcca  1200
atcctgggaa ctttcatagg ggatgcacac ccagtggaaa ggccatctaa ttattggtcc 1260
gaggaagctg aagaacgggt gatcactatt gggcggaagt gggaccctag tagtagaatt 1320
cggggtattg tgttgagcga tgcctaa                                    1347
```

| SEQ ID NO: 18 | moltype = AA  length = 448 |
| --- | --- |
| FEATURE | Location/Qualifiers |
| source | 1..448 |
| | mol_type = protein |
| | organism = Hypoxylon pulicicidum |

SEQUENCE: 18

```
MEVSSSETLP ILWRTSPPSN DYENARCRVF NGRQPEHFPL AIVKANKVEH IVAAVKLAAE    60
LDACIAVRSG GHSLSCWTIR HGAILIDLED YQHLSYDDEI HEVQASPSTL GADLLTFLAK   120
KKRFFPVGHS GDIGLGGYLL QGGIGLNSRG YGYACEYITG LDIITADGEI KHCDKTENSD   180
LYWAARGAGP EFPAIVIRFF LKTCPLLPVC KRSRYVWPAA MYGKVFKWLE ELLNSLSEDV   240
EIAVFGFVLP RLNQPGLVLH ATAFGDSSEN VREKLTPIIK NHPPGTFLAE DFVSTNFPED   300
YDLGKDTMPR GARYFTDSVF LKPGIDFVAT CKGMFTELKH PRALAYWQPM KTNIDRILPD   360
MAMSIHSHHY VSLLAIYEDP SEDQQQISWI IDRMKSLEPA ILGTFIGDAH PVERPSNYWS   420
EEEAEERVITI GRKWDPSSRI RGIVLSDA                                    448

SEQ ID NO: 19           moltype = DNA  length = 1694
FEATURE                 Location/Qualifiers
source                  1..1694
                        mol_type = genomic DNA
                        organism = Hypoxylon pulicicidum
SEQUENCE: 19
ttacccaact agcagtggaa acttcgagtc gccttctgtg accctgaaat cccatttgtc    60
atccttgaat tcctttctct ctctgagagt caccatgaac tccccctgcag gtgtctgtat   120
ggaacttgca agtgttttca cgttggcctt gggaggaatc cactctccga gcacgggctc   180
catgtcaaac cgtaaaatca ccatggctac taccgctaat atctcccag atgcgaagtg    240
gcgcccagga cagatgttag gtgctgtccc gaaagactgg aacgcaacgc gtgtgacgtt   300
acggccactt cgcgatgtcc cactcttccc ctggccgaga tatcgatatg cgtcgaagct   360
atcccctgtt tcgccccata ctgacttttc gcgattaaca cttgcagg gatcacgat     420
cacggacccc ttcttgaata gaactcgctc gttgaggatg gtatcctcat ggaccatgcg   480
cgtgactata gcattagacc tcatacggag gacctcctga aggtaccga gaagcaaact     540
gcacttggcg cgtacagcgc tgagatcaat agtacgaact atccctccat cggtacctgg   600
atgcgtgtac acagcagaag ccacgagctc ttgtcgaaga tccctcagca aactcgggcg   660
tgagtaaatt tcgaaaaggg tccaaaatgt ggaaggcgca gtattcgata ggacacctat   720
cgcgttaaca atttccattc gagctatatc ttgtgtggtg attcccttgt tatattggac   780
ctcccatcga ccatacgtca ttttccgagga gttttcgtgg cctcccaggt tgtaatactc   840
tgttagagcg tccacaacct tacgacgatc atctagggac tttcgtgctg tgagaaaggg   900
aaggacattg aggattatca tattcatatt cgacgcgaaa tccctacacc acgtatgagc   960
tcagcaattc ttacacagca ttggggttct attctgtgct ttgacctacc aaaaagcct  1020
ttcaacttct atggatcgga atggattcat aggaccgtaa accgagtctg tgctcgccat  1080
tgtgatagaa cgtttacacc atgcaaataa gtcgaatgcc gcttgtttct ggcttttggag  1140
ttcgtctatt gagggcttta tagcctcgat catggaaaga ttcatggcat ccaagccatg  1200
tcctataagt gcgtgatgca tagcatgttg tagctcatcc acgatactac ctttaagcaa  1260
tttaagtcca ggcccactga caccacctac acgttctgcg ccagtgtaa attcgaacgt   1320
atcgaatcgt atattctggg actgtctttg aatagccggg actagctcgc tagacgtgat  1380
cacataaagc cttgatagtg gcatctggag cgagaaggcg ggaagtccat atttgtcact  1440
atctacaccg ttagtctatg tactatatac agcatatctt cctcgcttca actaagcaac  1500
atgtagaagt cttaaccata cttgagcttg gaaaaatacc caaagccgtc agtcgcgata  1560
ccaagtatgt gcccgatgag tggtaccgta ggggatatca aacggggctc gcggggggtcg  1620
agagcagctc tccatcgagt accgtacagc aggatgcaaa aagcgagagt tatgataata  1680
acgataagtt ccat                                                    1694

SEQ ID NO: 20           moltype = DNA  length = 1545
FEATURE                 Location/Qualifiers
source                  1..1545
                        mol_type = genomic DNA
                        organism = Hypoxylon pulicicidum
SEQUENCE: 20
ttacccaact agcagtggaa acttcgagtc gccttctgtg accctgaaat cccatttgtc    60
atccttgaat tcctttctct ctctgagagt caccatgaac tccccctgcag gtgtctgtat   120
ggaacttgca agtgttttca cgttggcctt gggaggaatc cactctccga gcacgggctc   180
catgtcaaac cgtaaaatca ccatggctac taccgctaat atctcccag atgcgaagtg    240
gcgcccagga cagatgttag gtgctgtccc gaaagactgg aacgcaacgc gtgtgacgtt   300
acggccactt cgcgatgtcc cactcttccc ctggccgaga tatcgatatg cgtcgaagct   360
atcccctgtt tcgccccata ctgacttttc gcgattaaca catcttgcag ggatcacgat   420
cacggacccc ttcttgaata gaactcgctc gttgaggatg gtatcctcat ggaccatgcg   480
cgtgactata gcattagacc tcatacggag gacctcctga aggtaccga gaagcaaact    540
gcacttggcg cgtacagcgc tgagatcaat agtacgaact atccctccat cggtacctgg   600
atgcgtgtac acagcagaag ccacgagctc ttgtcgaaga tccctcagca aactcgggcg   660
tgagtaaatt tcgaaaaggg tccaaaatgt ggaaggcgca gtattcgata ggacacctat   720
cgcgttaaca atttccattc gagctatatc ttgtgtggtg attcccttgt tatattggac   780
ctcccatcga ccatacgtca ttttccgagga gttttcgtgg cctcccaggt tgtaatactc   840
tgttagagcg tccacaacct tacgacgatc atctagggac tttcgtgctg tgagaaaggg   900
aaggacattg aggattatca tattcatatt cgacgcgaaa tccaaaaag ccctttcaac    960
ttctatggat cggaatggat tcataggacc gtaaaccgag tctgtgctcg ccattgtgat  1020
agaacgttta caccatgcaa ataagtcgaa tgccgcttgt ttctggagttcgtc          1080
tattgagggc tttatagcct cgatcatgga agattcatg gcatccaagc catgtcctat   1140
aagtgcgtga tgcatagcat gttgtagctc atccacgata ctacctttaa gcaatttaag  1200
tccaggccca ctgacaccac ctacacgttc tgcggcagt gtaaattcga acgtatcgaa   1260
tcgtatattc tgggactgtc tttgaatagc cgggactagc tcgctagacg tgatcacata  1320
aagccttgat agtggcatct ggagcgagaa ggcgggaagt ccatatttgt cattggactct  1380
ggaaaaatac ccaaagccgt cagtcgcgat accaagtatg tgcccgatga gtggtaccgt  1440
aggggatatc aaacggggct cgcggggtc gagagcagct ctccatcgag taccgtacag  1500
caggatgcaa aaagcgagag ttatgataat aacgataagt tccat                  1545

SEQ ID NO: 21           moltype = AA  length = 514
```

| FEATURE | Location/Qualifiers |
|---|---|
| source | 1..514 |
| | mol_type = protein |
| | organism = Hypoxylon pulicicidum |

SEQUENCE: 21

```
MELIVIIITL AFCILLYGTR WRAALDPREP RLISPTVPLI GHILGIATDG FGYFSKLNDK    60
YGLPAFSLQM PLSRLYVITS SELVPAIQRQ SQNIRFDTFE FTLAAERVGG VSGPGLKLLK   120
GSIVDELQHA MHHALIGHGL DAMNLSMIEA IKPSIDELQS QKQAAFDLFA WCKRSITMAS   180
TDSVYGPMNP FRSIEVERAF WDFASNMNMI ILNVLPFLTA RKSLDDRRKV VDALTEYYNL   240
GGHENSSEMT YGRWEVQYNK GITTQDIARM EIVNAIGVLS NTAPSTFWTL FEIYSRPSLL   300
RDLRQELVAS AVYTHPGTDG GIVRTIDLSA VRAKCSLLLG TFQEVLRMRS NAIVTRMVHE   360
DTILNERVLF KKGSVIVIPA RCVNREKSVW GETGDSFDAY RYLGQGKSGT SRSGRNVTRV   420
APQSFGTAPN ICPGRHFASG EILAVVAMVI LRFDMEPVLG EWIPPKANVK TLASSIQTPA   480
GEFMVTLRER KEFKDDKWDF RVTEGDSKFP LLVG                               514
```

| SEQ ID NO: 22 | moltype = DNA   length = 1125 |
|---|---|
| FEATURE | Location/Qualifiers |
| source | 1..1125 |
| | mol_type = genomic DNA |
| | organism = Hypoxylon pulicicidum |

SEQUENCE: 22

```
atgtccttag gtttacagtg cttggcggca gtgttgtttt cggctttgtt ttcacttggg    60
gtcatcctag ttcatcttcc atggcgcgcc ttgaagtcaa aggacccgcg tgagcgaata   120
ttaggttcgc ccaaagaact ggttccaaca tgcccttacg aatatattcg aaatatatac   180
gggcgtcatc attgggcgcc ctttgtggcc aagttagcac cgaatctcaa agaaagtgat   240
tcagacaggt acacaatggt acttgaaatc atggactgca tacacctatg cctgattatg   300
gtcgatgatg tacgttcatc ttattatacg cctcttgttg gtgatagagg tgagagttgt   360
aaataactaa cccggactct cagattacag atgacagcga ctatcgtaaa ggccgcccag   420
cggcccatat catctatggc cgttcggaga cagctaaccg tgcttatctt cgtgtcagtc   480
agattataaa caagacaact caggacttcc cgcggctcgc cccgtgggtc acacagagtt   540
tggcagagat tctagagggc caggacatct cgctggtttg gcgacgagac ggcctcacta   600
gctttccaaa agctcacgac gagcgcgtga ttgcttatcg gtgcatgtca tctttgaaga   660
ctggcgcgct ttttaggttg ctagggaggc ttgtcttgga aaatcgttcc atggatgaca   720
cattgagtca ggttgggtaa gtgaactgta tccatcctga actcgacccc tttcacagtg   780
gcggaagcca atgctaaaac gtctagatac tattcacaat tacaaaatga ctgcaaaaat   840
gttttctcat ccgagtacgc aaaggcaaaa ggtactttag ctgaggactt acggaaccga   900
gagctgacgt atcctatcat cttggccctc aatgagcctg aaggatttta tattgagaaa   960
gcctttgagt ctggctcccc tcgtgacata caaaatgcaa tcggtgtaat acagagtgaa  1020
aacgtatacc gtgcttgttt ggacgagttg aaacaatatg aatcgaacgt cagagagtgg  1080
gttacactat ggggtagaaa ggagaaactc gatcttacgc attga                  1125
```

| SEQ ID NO: 23 | moltype = DNA   length = 981 |
|---|---|
| FEATURE | Location/Qualifiers |
| source | 1..981 |
| | mol_type = genomic DNA |
| | organism = Hypoxylon pulicicidum |

SEQUENCE: 23

```
atgtccttag gtttacagtg cttggcggca gtgttgtttt cggctttgtt ttcacttggg    60
gtcatcctag ttcatcttcc atggcgcgcc ttgaagtcaa aggacccgcg tgagcgaata   120
ttaggttcgc ccaaagaact ggttccaaca tgcccttacg aatatattcg aaatatatac   180
gggcgtcatc attgggcgcc ctttgtggcc aagttagcac cgaatctcaa agaaagtgat   240
tcagacaggt acacaatggt acttgaaatc atggactgca tacacctatg cctgattatg   300
gtcgatgata ttacagatga cagcgactat cgtaaaggcc gcccagcggc ccatatcatc   360
tatggccgtt cggagacagc taaccgtgct tatcttcgtg tcagtcagat tataaacaag   420
acaactcagg acttcccgcg gctcgccccg tgggtcacac agagtttggc agagattcta   480
gagggccagg acatctcgct ggtttggcga cgagacggcc tcactagctt tccaaaagct   540
cacgacgagc gcgtgattgc ttatcggtgc atgtcatctt tgaagactgg cgcgcttttt   600
aggttgctag ggaggcttgt cttggaaaat cgttccatgg atgacacatt gagtcaggtt   660
ggatactatt cacaattaca aaatgactgc aaaaatgttt tctcatccga gtacgcaaag   720
gcaaaaggta ctttagctga ggacttacgg aaccgagagc tgacgtatcc tatcatcttg   780
gccctcaatg agcctgaagg attttatatt gagaaagcct ttgagtctgg ctcccctcgt   840
gacatacaaa atgcaatcgg tgtaatacag agtgaaaacg tataccgtgc ttgtttggac   900
gagttgaaac aatatgaatc gaacgtcaga gagtgggtta cactatgggg tagaaaggag   960
aaactcgatc ttacgcattg a                                             981
```

| SEQ ID NO: 24 | moltype = AA   length = 326 |
|---|---|
| FEATURE | Location/Qualifiers |
| source | 1..326 |
| | mol_type = protein |
| | organism = Hypoxylon pulicicidum |

SEQUENCE: 24

```
MSLGLQCLAA VLFSALFSLG VILVHLPWRA LKSKDPRERI LGSPKELVPT CPYEYIRNIY    60
GRHHWAPFVA KLAPNLKESD SDRYTMVLEI MDCIHLCLIM VDDITDDSDY RKGRPAAHII   120
YGRSETANRA YLRVSQIINK TTQDFPRLAP WVTQSLAEIL EGQDISLVWR RDGLTSFPKA   180
HDERVIAYRC MSSLKTGALF RLLGRLVLEN RSMDDTLSQV GYYSQLQNDC KNVFSSEYAK   240
AKGTLAEDLR NRELTYPIIL ALNEPEGFYI EKAFESGSPR DIQNAIGVIQ SENVYRACLD   300
ELKQYESNVR EWVTLWGRKE KLDLTH                                        326
```

| SEQ ID NO: 25 | moltype = DNA   length = 1439 |

| FEATURE | Location/Qualifiers |
|---|---|
| source | 1..1439 |
| | mol_type = genomic DNA |
| | organism = Hypoxylon pulicicidum |

SEQUENCE: 25

```
ttaagagatg ttggtggcga cgtactcctt ccaccacga attgctttga cgaccttgtc    60
atattcctcg taggcatgct cctggctgtt gtgctctgaa acccagtccc taagtggcac   120
ttctgggtac atgttgatgc cctggtccgg ctgttccacg ttgtgctgaa gagctgaagc   180
tcgtggcttt cttttcggga gggaaagaaa tatgagttga ctaccgtacg tatctacgat   240
gttcttattg ttgttagact gctttacgta cctgattttc tcagccacac ggagcgcgag   300
agggacgttc ccctttcctg cgagctcgag gcagattgcc acgactgcgg catcctcaat   360
gacaagagac tccccaatgg gagagtttag gcggaagggt gcgaagcgt cgccaatgag    420
aatcatgcgg ccctgaggag agacccatga tggaagctgt cccagctgaa gaacgggttc   480
atcaacaagg cttccagatg gcgcggcctg gacgaccgct tcgatgttgg ctttgaacgg   540
ccatgattgg atgggcttga ggaagtcttg tgcggtagca ggagttgatg acgtcttggc   600
tgagttagga gattcctaga agatactata agcaggtgct cgtccaacat gtacctcaag   660
aatacatacc accttgtaca tgttactaaa tgctacgttg cgaccacccc cacaagtgac   720
gatggtgaga caggcagttg gaccaggcac aaatatcatc tgctcactt cacccgctcc    780
ttggaggatc cattgggcgt ctgggtttcc ttttaggcta gcgatatcag ccctaccccg   840
gatgtgtgcg tatccgctgt gggttggctt gaggctggag cctgcgacgg agtctcggcc   900
tttgctgttc acaccatctg cccagatgat gcagtctgcc tgcagcttct ggccattggc   960
agagacgccg gcctgatcgc tctcctccca gtaatcagaa atctcagttc gcgaaccgac  1020
gtcgattcca agagtcttcg catgatcgta aacgatcttg gtcagctccc gtcggaggat  1080
caggtacttg ttgctcgatg gtttccgaac ttcaatggtc tgaacctgct ttccggtggt  1140
gtcatacaca gatgcttggg tgttattaaa cttccaagca ttcaaggcct gacccacagc  1200
tccgttgcc cattagaga caatcacacc gcattgttc tcaatcatga cggtgtcatc    1260
tattatccta gtcattaaat tgctcttgat agtgtgagtg tatacttacc gacgtaattg  1320
agatccttgg accgttccag tgcaatgaca gaatgcccct tttggtgaca ttctatcgct  1380
gtggtaagac cagccaagcc aagtccaacc acaattacac taacaccggt tgaagccat   1439
```

| SEQ ID NO: 26 | moltype = DNA   length = 1296 |
|---|---|
| FEATURE | Location/Qualifiers |
| source | 1..1296 |
| | mol_type = genomic DNA |
| | organism = Hypoxylon pulicicidum |

SEQUENCE: 26

```
ttaagagatg ttggtggcga cgtactcctt ccaccacga attgctttga cgaccttgtc    60
atattcctcg taggcatgct cctggctgtt gtgctctgaa acccagtccc taagtggcac   120
ttctgggtac atgttgatgc cctggtccgg ctgttccacg ttgtgctgaa gagctgaagc   180
tcgtgggatg ttcttattgt tgttagactg ctttacgtac ctgattttct cagccacacg   240
gagcgcgaga gggacgttcc cctttcctgc gagctcgagg cagattgcca cgactgcggc   300
atcctcaatg acaagagact ccccaatggg agagtttagg cggaagggt gcgaagcgtc    360
gccaatgaga atcatgcggc cctgaggaga gacccatga tggaagctgt ccagctgaag   420
aacgggttca tcaacaaggc ttccagatgg cgcggcctgg acgaccgctt cgatgttggc   480
tttgaacggc catgattgga tgggcttgag gaagtcttgt gcggtagcag gagttgatga   540
cgtcttggct gagttaggag attccacctt gtacatgtta ctaaatgcta cgttgcgacc   600
accccacaa gtgacgatgg tgagacaggc agttggacca ggcacaaata tcatctggtc    660
tacttcaccc gctccttgga ggatccattg ggcgtctggg ttccttttta ggctagcgat   720
atcagcccta ccccgatgt gtgcgtatcc gctgtgggtt ggcttgaggc tggagcctgc    780
gacggagtct cggcctttgc tgttcacacc atctgcccag atgatgcagt ctgcctgcag   840
cttctggcca ttggcagaga cgccggcctg atcgctctcc tcccagtaat cagagatctc   900
agttccgaac gcatgtcga ttccaagagt cttcgcatga tcgtaaacga tcttggtcag    960
ctcccgtcgg aggatcaggt acttgttgct cgatggtttc cgaacttcaa tggtctgaac  1020
ctgctttccg gtggtgtcat acacagatgc ttgggtgtta ttaaacttcc aagcattcaa  1080
ggcctgaccc acagctccgt tgcccattt agagacaatc acaccgcatt gttgtcaat    1140
catgacggtg tcatctatta tcttaccgac gtaattgaga tccttggacc gttccagtgc  1200
aatgacagaa tgcccctttt ggtgacattc tatcgctgtg gtaagaccag ccaagccaag  1260
tccaaccaca attacactaa caccggttga agccat                             1296
```

| SEQ ID NO: 27 | moltype = AA   length = 431 |
|---|---|
| FEATURE | Location/Qualifiers |
| source | 1..431 |
| | mol_type = protein |
| | organism = Hypoxylon pulicicidum |

SEQUENCE: 27

```
MASTGVSVIV VGLGLAGLTT AIECHQKGHS VIALERSKDL NYVGKIIDDT VMIDNNAGVI    60
VSKWGNGAVG QALNAWKFNN TQASVYDTTG KQVQTIEVRK PSSNKYLILR RELTKIVYDH   120
AKTLGIDMRF GTEISDYWEE SDQAGVSANG QKLQADCIIW ADGVNSKGRD SVAGSSLKPT   180
HSGYAHIRGR ADIASLKGNP DAQWILQGAG EVDQMIFVPG PTACLTIVTC GGGRNVAFSN   240
MYKVESPNSA KTSSTPATAQ DFLKPIQSWP FKANIEAVVQ AAPSGSLVDE PVLQLGQLPS   300
WVSPQGRMIL IGDASHPSAL NSPIGESLVI EDAAVVAICL ELAGKGNVPL ALRVAEKIRY   360
VKQSNNNKNI PRASALQHNV EQPDQGINMY PEVPLRDWVS EHNSQEHAYE EYDKVVKAIR   420
GGKEYVATNI S                                                        431
```

| SEQ ID NO: 28 | moltype = DNA   length = 1372 |
|---|---|
| FEATURE | Location/Qualifiers |
| source | 1..1372 |
| | mol_type = genomic DNA |
| | organism = Hypoxylon pulicicidum |

```
SEQUENCE: 28
atggactcta ccgggagaca gcctctcagc caggacgggc agccatggca agctcttgcc   60
tctggcttgg gatttccaga tgaagaccag aagtattggt ggtcagtcat ggcgccccta  120
ttaggggaac tgatgaaatg ggccaactat cctgttgata acagtatctc tgttcttgcg  180
ttctgccatg aatacatact tccattttgc ggacctcgtc caacggccga aggcggtatc  240
ttctggccca cgttgatcac caaggatggt actccgttcg agccgagcct taacttctac  300
aaaaataaag ccactctacg agttggatat gcgcctgcat gcgagctttc aggaagcaat  360
gacgaccca tcaatcaacg agccccaatt gcggcattgg agcaccaaaa gagagtccta  420
ccacagcaga atctcaaatg ggtggataat ttcaagaaag catggttcat cgataatgac  480
gacgcagtag ccttgaaggc acgcgtacac aacgagctct tgaacaggc agccgtccaa  540
tgcttgatag gttatgtgtt ttccgactac acgcaggtca aggttgccat gagtcctctt  600
tggaagtcag tccagacagg ccagcaaatt cgcgagtga tctgggacac ctttcgccag  660
cttggagacg atgcttccag ttacctagat tgcctatcag tgctagagga gtatactgag  720
tctaaacagg ccaaactagc acaagtacag ccttccttcg tcaatttcga tgtgaatctg  780
aaggggggact accagcagtc gcgacttaag gtatactatg ctacaccatg cactgcattc  840
gacacgatgg tccaggtttt cactttgggc ggaaggctca agggccctga agttgaccat  900
gcgattgaat gccttcgtgt cctatggccc agcgtgcttg cagttcctga aaaccatccg  960
gacgaccaag acttgcctcg acggtaccac tctgtagcag tgacccagtt taacttcgag 1020
ctctggccgg gagcgaaact gcctgttccc cagatctatc tcccgactaa cttttacggt 1080
cgtgatgaat ggaaaattgc ggagggccta gaggatttt tcaagactct ggctggagt 1140
gagcctttcc atgcctataa acagaattac attgcaacat ggttagtcta tcgcctttct 1200
ctcgctcatt gccctgcaca aatgaagtat tttactcaca ctgtagtg ccacgcccga 1260
agggaaatgg aaagcgatcc aacacgacg atcattctcg ttcaaggact caagcccata 1320
tgtgtcggtt tattataaac cagagctctc ggtcctatcc tcaccgtcgt ag          1372

SEQ ID NO: 29         moltype = DNA   length = 1305
FEATURE               Location/Qualifiers
source                1..1305
                      mol_type = genomic DNA
                      organism = Hypoxylon pulicicidum
SEQUENCE: 29
atggactcta ccgggagaca gcctctcagc caggacgggc agccatggca agctcttgcc   60
tctggcttgg gatttccaga tgaagaccag aagtattggt ggtcagtcat ggcgccccta  120
ttaggggaac tgatgaaatg ggccaactat cctgttgata acagtatctc tgttcttgcg  180
ttctgccatg aatacatact tccattttgc ggacctcgtc caacggccga aggcggtatc  240
ttctggccca cgttgatcac caaggatggt actccgttcg agccgagcct taacttctac  300
aaaaataaag ccactctacg agttggatat gcgcctgcat gcgagctttc aggaagcaat  360
gacgaccca tcaatcaacg agccccaatt gcggcattgg agcaccaaaa gagagtccta  420
ccacagcaga atctcaaatg ggtggataat ttcaagaaag catggttcat cgataatgac  480
gacgcagtag ccttgaaggc acgcgtacac aacgagctct tgaacaggc agccgtccaa  540
tgcttgatag gttatgtgtt ttccgactac acgcaggtca aggttgccat gagtcctctt  600
tggaagtcag tccagacagg ccagcaaatt cgcgagtga tctgggacac ctttcgccag  660
cttggagacg atgcttccag ttacctagat tgcctatcag tgctagagga gtatactgag  720
tctaaacagg ccaaactagc acaagtacag ccttccttcg tcaatttcga tgtgaatctg  780
aaggggggact accagcagtc gcgacttaag gtatactatg ctacaccatg cactgcattc  840
gacacgatgg tccaggtttt cactttgggc ggaaggctca agggccctga agttgaccat  900
gcgattgaat gccttcgtgt cctatggccc agcgtgcttg cagttcctga aaaccatccg  960
gacgaccaag acttgcctcg acggtaccac tctgtagcag tgacccagtt taacttcgag 1020
ctctggccgg gagcgaaact gcctgttccc cagatctatc tcccgactaa cttttacggt 1080
cgtgatgaat ggaaaattgc ggagggccta gaggatttt tcaagactct ggctggagt 1140
gagcctttcc atgcctataa acagaattac attgcaacat gtgccacgcc cgaagggaaa 1200
tggaaagcga tccaacacga cgtatcattc tcgttcaagg actcaagccc atatgtgtcg 1260
gtttattata aaccagagct ctcggtccta tcctcaccgt cgtag                 1305

SEQ ID NO: 30         moltype = AA    length = 434
FEATURE               Location/Qualifiers
source                1..434
                      mol_type = protein
                      organism = Hypoxylon pulicicidum
SEQUENCE: 30
MDSTGRQPLS QDGQPWQALA SGLGFPDEDQ KYWWSVMAPL LGELMKWANY PVDKQYLVLA   60
FCHEYILPFC GPRPTAEGGI FWPTLITKDG TPFEPSLNFY KNKATLRVGY APACELSGSN  120
DDPINQRAPI AALEHQKRVL PQQNLKWVDN FKKAWFIDND DAVALKARVH NELFEQAAVQ  180
CLIGYVFSDY TQVKVAMSPL WKSVQTGQQI SRVIWDTFRQ LGDDASSYLD CLSVLEEYTE  240
SKQAKLAQVQ PSFVNFDVNL KGDYQQSRLK VYYATPCTAF DTMVQVFTLG GRLKGPEVDH  300
AIECLRVLWP SVLAVPENHP DDQDLPRRYH SVAVTQFNFE LWPGAKLPVP QIYLPTNFYG  360
RDELEIAEGL EGFFKTLGWS EPFHAYKQNY IATCATPEGK WKAIQHDVSF SFKDSSPYVS  420
VYYKPELSVL SSPS                                                    434

SEQ ID NO: 31         moltype = DNA   length = 1354
FEATURE               Location/Qualifiers
source                1..1354
                      mol_type = genomic DNA
                      organism = Hypoxylon pulicicidum
SEQUENCE: 31
atggatgctg cttcaactct tacgcatgca ccggtatctc agccatggca gtccctagct   60
caagggttgg ggttcgtcaa tgagcatgaa gggtactggt ggtctaagct tggaccttct  120
ctcggtaaaa tgatgaactg gctcgatac tcgacatcgg aacagtacag agtcctagca  180
ttcctttaca aatatcttct ccctgcctgc ggcccaaagc tggtgatga tgtgagctg   240
```

```
ttctggaagg ttttcatcag ctatgattac acgcccattc agctcagtct caattttcac    300
aatggcaaaa tgacgctgcg caccgcgaac ataccaatta gcgataaatc gggaaccgca    360
gacgacccaa tcaaccaaca agcttcggta gacgccataa tccgccagga acgagtgttg    420
ccatcccagg atctacgttg gttcaaccac tttgcatccc agtacttctt cgacaaggac    480
acggcagcct ctctaaagac caaggtcgat aagctccgag tccagcaggg agttcagtgt    540
atgctgagcc acgactttcc tgagcgtgat gtccaatgca aagtggcttt ctgcccgctt    600
tggaaagccg tcgctacagg tctttccaac aaggagatca tctgggattc gattctaggg    660
ctcggagatg acatcatccc atacaagcga gcgcttgctg tccttgaaca gtacacatcg    720
tccgaaaatg cagcgaaagc aggagtgcga cctgtattct tcgctttcga tacggtgtta    780
aaagataatt acaagagctc tcgtatcaag atctactacc tcacaacacg gacagccttc    840
aactctatgg tcgacatcta cacacttgga ggcctgctaa agggcctgaa tatccaaaaa    900
ggagtagagg cccttgaagt gctctggaaa gccgtcctca acgtcccga ggggtggccc     960
gatgataaag atctacccat gaatccacac cgttgtgcgg cagtaatctt caattttgag   1020
ctgtggccag gagcagagtt tccgagtccc aaggcctatc tcccagccca ttattatggc   1080
cggcctgatt tggagatagc tgatggtatg gactacttct tcaagcagca agggttggat   1140
ggggtatatg gttcttacaa ggagaactat ttgaagtgct tgtacgacct cctcacctca   1200
ctcacatcta ccaagctatg gctaatagat cagaagtacg aactcacaga accaactcac   1260
agccctccac catgatattt ctttttcatt caaagggtcc aatgcctacg ttacggtgta   1320
ctacaagccc gagctatctc tagataccga gtag                               1354

SEQ ID NO: 32           moltype = DNA  length = 1302
FEATURE                 Location/Qualifiers
source                  1..1302
                        mol_type = genomic DNA
                        organism = Hypoxylon pulicicidum
SEQUENCE: 32
atggatgctg cttcaactct tacgcatgca ccggtatctc agccatggca gtccctagct     60
caagggttgg ggttcgtcaa tgagcatgaa gggtactggt ggtctaagct tggacctcct    120
ctcggtaaaa tgatgaactg ggctcgatac tcgacatcgg aacagtacag agtcctagca    180
ttcctttaca aatatcttct ccctgcctgc ggcccaaagc ctggtgatga tggtgagctg    240
ttctggaagg ttttcatcag ctatgattac acgcccattc agctcagtct caattttcac    300
aatggcaaaa tgacgctgcg caccgcgaac ataccaatta gcgataaatc gggaaccgca    360
gacgacccaa tcaaccaaca agcttcggta gacgccataa tccgccagga acgagtgttg    420
ccatcccagg atctacgttg gttcaaccac tttgcatccc agtacttctt cgacaaggac    480
acggcagcct ctctaaagac caaggtcgat aagctccgag tccagcaggg agttcagtgt    540
atgctgagcc acgactttcc tgagcgtgat gtccaatgca aagtggcttt ctgcccgctt    600
tggaaagccg tcgctacagg tctttccaac aaggagatca tctgggattc gattctaggg    660
ctcggagatg acatcatccc atacaagcga gcgcttgctg tccttgaaca gtacacatcg    720
tccgaaaatg cagcgaaagc aggagtgcga cctgtattct tcgctttcga tacggtgtta    780
aaagataatt acaagagctc tcgtatcaag atctactacc tcacaacacg gacagccttc    840
aactctatgg tcgacatcta cacacttgga ggcctgctaa agggcctgaa tatccaaaaa    900
ggagtagagg cccttgaagt gctctggaaa gccgtcctca acgtcccga ggggtggccc     960
gatgataaag atctacccat gaatccacac cgttgtgcgg cagtaatctt caattttgag   1020
ctgtggccag gagcagagtt tccgagtccc aaggcctatc tcccagccca ttattatggc   1080
cggcctgatt tggagatagc tgatggtatg gactacttct tcaagcagca agggttggat   1140
ggggtatatg gttcttacaa ggagaactat ttgaagtgct taagtacgaa ctcacagaac   1200
caactcacag ccctccacca tgatatttct ttttcattca aagggtccaa tgcctacgtt   1260
acggtgtact acaagcccga gctatctcta gataccgagt ag                      1302

SEQ ID NO: 33           moltype = AA  length = 433
FEATURE                 Location/Qualifiers
source                  1..433
                        mol_type = protein
                        organism = Hypoxylon pulicicidum
SEQUENCE: 33
MDAASTLTHA PVSQPWQSLA QGLGFVNEHE GYWWSKLGPP LGKMMNWARY STSEQYRVLA     60
FLYKYLLPAC GPKPGDDGEL FWKVFISYDY TPIQLSLNFH NGKMTLRTAN IPISDKSGTA    120
DDPINQQASV DAIIRQERVL PSQDLRWFNH FASQYFFDKD TAASLKTKVD KLRVQQGVQC    180
MLSHDFPERD VQCKVAFCPL WKAVATGLSN KEIIWDSILG LGDDIIPYKR ALAVLEQYTS    240
SENAAKAGVR PVFFAFDTVL KDNYKSSRIK IYYLTTRTAF NSMVDIYTLG GLLKGPDIQK    300
GVEALEVLWK AVLNVPEGWP DDKDLPMNPH RCAAVIFNFE LWPGAEFPSP KAYLPAHYYG    360
RPDLEIADGM DYFFKQQGLD GVYGSYKENY LKCLSTNSQN QLTALHHDIS FSFKGSNAYV    420
TVYYKPELSL DTE                                                      433

SEQ ID NO: 34           moltype = DNA  length = 1562
FEATURE                 Location/Qualifiers
source                  1..1562
                        mol_type = genomic DNA
                        organism = Hypoxylon pulicicidum
SEQUENCE: 34
atggcgcctg atagacttgg tcccgagggc acagcacgcc ccaattccag tggcatctca     60
gttatcgtgg tcgccttgg aattgctggc taacagctg caattgagtg ccaccggaag     120
ggccattcag tcattgcctt cgagcgaatg aaggatgtcg aaccctttgg tgagtttggc    180
ttcgaatcc catattggtt actccgccaa cctagtaaag gcgatagcat catcatcgga    240
agcaacggcg gccgtatttt cggcaaatgg ggccgcggtg aggtacgcaa tgctatgcaa    300
gcctggcgat atacgcctac ccatgccgac atttacgata ccgccggaag attcatggcc    360
cagtctgaga ttcccaaagc tgcggatgac atgtacttca ctcttcgagg cagactagcg    420
aagaccttcg acgaacacgc acaaagcctc ggcattgata tgaggatggg gtcgaaagtg    480
actgaatttt gggaagacag caatcgggct ggaatcgttg tggaaggaga gaggtttgag    540
```

-continued

```
gccgactgtg ttatttgcgc tgatggcata cacagcaagt ctcgctcctt gttcacttct    600
ctaaacgctc aaccatttcg ttctggtttc tctattttca gggggaaagc ggacgctaat    660
gcgattattg ccgatcccga tgcgaaatgg atccttgacc agacagagaa caccgatcag    720
ttcaaagtgt ttctggggaa ggagatctgt gttgtcataa ttacctgcgg gctaggccgt    780
gcagtggtct gcagtgctat gcatagggtg agcaatacct atctcccaga taccaataat    840
atatagcagg taggctttgg actatatctt cctgttctgc tcacacaaga ctgcccagg     900
acctaaatga agcggaacag tcgtggtcga cccatgccaa cccggatgat ctattggacg    960
ccatcaaaga ctggccgtgc aggcgccaga tcgaaccaat cgttcggaag atatccgaag   1020
accagttcat cgactatccc cttctaactg tgtctccact ggacacgtgg gtatcccagc   1080
acgggcggat gattctaata ggagatgctg ctcatccatt ctttccgact tccggacaag   1140
gaggcgcaca agccatggag gatgcagctg tgcttgcaat ttgcctcgag ttggcaggga   1200
aaggaaacat cccctggct cttcatgcaa cagaaaagat caggtctagt ttcccggccc    1260
ttcgggctac tctcccttc cattttatcc gttttccta ctttcgctaa taccacgtaa     1320
cttccagaaa gagccgagct tcagtcctcc aactaaacag acgtattca gaagggctc     1380
aactagcacc tgcgctgccg aaatccaaag acagtatgtc tgttccaaat gttccagtaa   1440
tggattggat ctggcatcac tgctgccagt cctacgcata tgatgagttc gacaaggtag   1500
cggaggcgat tcaaagcggg agtgaataca ttccacataa tcttccagaa gatggtacgt   1560
ag                                                                  1562

SEQ ID NO: 35           moltype = DNA   length = 1386
FEATURE                 Location/Qualifiers
source                  1..1386
                        mol_type = genomic DNA
                        organism = Hypoxylon pulicicidum
SEQUENCE: 35
atggcgcctg atagacttgg tcccgagggc acagcacgcc ccaattccag tggcatctca     60
gttatcgtgg tcggccttgg aattgctggc ctaacagctg caattgagtg ccaccggaag    120
ggccattcag tcattgcctt cgagcgaatg aaggatgtcg aaccctttgg tgagtttggc    180
ttcgaatccc catattggtt actccgccaa cctagtaaag gcgatagcat catcatcggc    240
agcaacggcg gccgtatttt cggcaaatgg ggccgcgttg aggtacgcaa tgctatgcaa    300
gcctggcgat atacgcctac ccatgccgac atttacgata ccgccggaag attcatggcc    360
cagtctgaga ttcccaaagc tgcggatgac atgtacttca ctcttcgagg cagactagcg    420
aagaccttct acgaacacgc acaaagcctc ggcattgata tgaggatggg gtcgaaagtg    480
actgaatttt ggaagacag caatcgggct ggaatcgttg tggaaggaag gaggttttgag   540
gccgactgtg ttatttgcgc tgatggcata cacagcaagt ctcgctcctt gttcacttct    600
ctaaacgctc aaccatttcg ttctggtttc tctattttca gggggaaagc ggacgctaat    660
gcgattattg ccgatcccga tgcgaaatgg atccttgacc agacagagaa caccgatcag    720
ttcaaagtgt ttctggggaa ggagatctgt gttgtcataa ttacctgcgg gctaggccgt    780
gcagtggtct gcagtgctat gcataggac ctaaatgaag cggaacagtc gtggtcgacc    840
catgccaacc cggatgatct attggacgcc atcaaagact ggccgtgcag gcgccagatc    900
gaaccaatct tcggaagat atccgaagac cagttcatcg actatcccct ctaactgtg     960
tctccactgg acacgtgggt atcccagcac gggcggatga ttctaatagg agatgctgct   1020
catccattct ttccgacttc cggacaagga ggcgcacaa gccatggagg atgcagctg      1080
cttgcaattt gcctcgagtt ggcagggaaa ggaaacatcc cctggctct catgcaaca     1140
gaaaagatca gaagagccg agcttcagtc tccaactaa acaggacgta ttcagaaggg   1200
gttcaactag cacctgcgct gccgaaatcc aaagacagta tgtctgttcc aaatgttcca  1260
gtaatggatt ggatctggca tcactgctgc cagtcctacg catatgatga gttcgacaag  1320
gtagcggagg cgattcaaag cggagtgaa tacattccac ataatcttcc agaagatggt  1380
acgtag                                                             1386

SEQ ID NO: 36           moltype = AA   length = 461
FEATURE                 Location/Qualifiers
source                  1..461
                        mol_type = protein
                        organism = Hypoxylon pulicicidum
SEQUENCE: 36
MAPDRLGPEG TARPNSSGIS VIVVGLGIAG LTAAIECHRK GHSVIAFERM KDVEPFGEFG     60
FESPYWLLRQ PSKGDSIIIG SNGGRIFGKW GRGEVRNAMQ AWRYTPTHAD IYDTAGRFMA    120
QSEIPKAADD MYFTLRGRLA KTFYEHAQSL GIDMRMGSKV TEFWEDSNRA GIVVEGERFE    180
ADCVICADGI HSKSRSLFTS LNAQPFRSGF SIFRGKADAN AIIADPDAKW ILDQTENTDQ    240
FKVFLGKEIC VVIITCGLGR AVVCSAMHRD LNEAEQSWST HANPDDLLDA IKDWPCRRQI    300
EPIVRKISED QFIDYPLLTV SPLDTWVSQH GRMILIGDAA HPFFPTSGQG GAQAMEDAAV    360
LAICLELAGK GNIPLALHAT EKIRKSRASV LQLNRTYSEG VQLAPALPKS KDSMSVPNVP    420
VMDWIWHHCC QSYAYDEFDK VAEAIQSGSE YIPHNLPEDG T                        461

SEQ ID NO: 37           moltype = DNA   length = 1844
FEATURE                 Location/Qualifiers
source                  1..1844
                        mol_type = genomic DNA
                        organism = Hypoxylon pulicicidum
SEQUENCE: 37
atgataacag catccacttc cgtgtttggt ggcttaatcc ttgcctttat cttctcactt     60
ttatataaga ataagaagac ccgtatccca gcagaaatcg accgcgtaag gacgggaggt    120
ttcctagcac acattagagc ctttgggtgc aggttaggta cgcagagttga tgatattcgc   180
aatggatata ataaggttag ttgctcctat agctgctcac aacaaatact caacacatga    240
tatctcaata cgcagttcaa caaaaacggt aagccgtttg tgatccagga ttctacctttg   300
atcccacagg tcgtcatacc acctcaatac ctgggatggt tgaaggagca accagagaag    360
gctctttctg cagaaaccgt gaggctagaa cagcttggac ttcgctattt ggtccctagc    420
tcagatcccg agatggtcca tttgttgaca gacgtcgtgt gtcgctatct tacccgcaat    480
```

```
tttcaaagag tacaagagcg tttatatgag gagctccata tgagtacgga tgaaatcatg    540
gggctggagg caactgagtg gcgtcagatt tgtctccatg aagcgatgga aacgattctt    600
cgaaggatga ttagttgcgt cctgattggt ctcccatggt gtcgagatga ggaatgctta    660
aaatcgtgga ccggatttct tcactgcatg gccattgcag gaactattct aggggcagta    720
acaccttggt tcctacggcc actcctcgga ctactgctca agccgcccgt tggctatatg    780
cgcagaagat cactgcgtta tcttactccg atctttactg aaagatggaa aaaaattgag    840
aagcatgaga gagctcact gacgacgcgt gagctgccgg atgacttcgt aacatggtgt     900
attcaggagg tacggaatgg taatatgaaa gaaaaaacacg atgctcttag ccttgcgtcg    960
gaatttctat tctttgtgag tcactctacg cgttggtatc atggtttccc atattcaata   1020
cgcgatgcga tggatcgagg ctctaacgag aacgcagtcg atcgcattct ttgacgcgcc   1080
tataggagct gcagaagtca ccatgctcga tcttctaagt gcggatccca caataggtta   1140
ctgggaaaag cttgtggaag aagccactac tgcattcaga acagacgagg actggattca   1200
tgcaggcact gtgtcaaaat tggcatacac ggacagcgca atcagggagt ctctacgccg   1260
aaaccctttc agcatccgaa acgtgacccg agaggtgata ggaaaagatg ggctaacact   1320
gccatccggt acgcgtctgc cacagggcac ttggatcacg accgctcctcg ccaatataca   1380
tcatgatgca agattttact caaatcccac cgaataccag cctttccgtt ttgtggccag   1440
agacgcgttt cacacagagg ggaaagaggg tagcgaaaag gttttacagc cctctgaagc   1500
tatcttgacg agcacaattg atgaaaggct cttgacattc ggatatgggc tcgagcgatg   1560
gtacgaaatc caactgtctc ctagagtctc aaactcttat atcctgtctc cagtcgaacc   1620
tacctaggta ctaatgcttt tgcaattact gtagccccgg ccgatggttc gcttcacaca   1680
tactgaaaat gttgatcgcg tatatcacga tcaattatga catacagccc ttgacgggac   1740
cgccgaaaaa agtcaaattc gcagatttca ccgtgccatc gccgagtatc aaaatcattg   1800
tgcgccggaa gaatctcgct tacctaggc aacgtgagcg ttga                     1844

SEQ ID NO: 38          moltype = DNA   length = 1524
FEATURE                Location/Qualifiers
source                 1..1524
                       mol_type = genomic DNA
                       organism = Hypoxylon pulicicidum
SEQUENCE: 38
atgataacag catccacttc cgtgtttggt ggcttaatcc ttgcctttat cttctcactt     60
ttatataaga ataagaagac ccgtatccca gcagaaatcg accgcgtaag gacgggaggt    120
ttcctagcac acattagagc ctttgggtgc aggttaggta cgcgagttga tgatattcgc    180
aatggatata ataagttcaa caaaaacggt aagccgtttg tgatccagga ttctacctttt   240
atcccacagg tcgtcatacc acctgtcaat actgggatgt tgaaggagca accagagaag    300
gctcttttctg cagaaaccgt gaggctagaa cagcttggac ttcgctattt ggtccctagc   360
tcagatcccg agatggtcca tttgttgaca gacgtcgtgt gtcgctatct acccgcaat    420
tttcaaagag tacaagagcg tttatatgag gagctccata tgagtacgga tgaaatcatg    480
gggctggagg caactgagtg gcgtcagatt tgtctccatg aagcgatgga aacgattctt    540
cgaaggatga ttagttgcgt cctgattggt ctcccatggt gtcgagatga ggaatgctta    600
aaatcgtgga ccgggattct tcactgcatg gccattgcag gaactattct aggggcagta    660
acaccttggt tcctacggcc actcctcgga ctactgctca agccgcccgt tggctatatg    720
cgcagaagat cactgcgtta tcttactccg atctttactg aaagatggaa aaaaattgag    780
aagcatgaga gagctcact gacgacgcgt gagctgccgg atgacttcgt aacatggtgt     840
attcaggagg tacggaatgg agctgcagaa gtcaccatgc tcgatcttct aagtgcggat    900
cccacaataag gttactggga aaagcttgtg gaagaagcca ctactgcatt cagaacagac   960
gaggactgga ttcatgcagg cactgtgtca aaattgcat acacggacag cgcaatcagg   1020
gagtctctac gccgaaaccc tttcagcatc cgaaacgtga cccgagaggt gataggaaaa   1080
gatgggctaa cactgccatc cggtacgcgt ctgccacagg gcacttggat cacgaccgct   1140
ctcgccaata tacatcatga tgcaagattt tactcaaatc ccaccgaata ccagcctttc   1200
cgttttgtgg ccagagacgc gttttcacaca gaggggaaag aagggtagcg aaaaggtttca    1260
cagccctctg aagctatctt gacgagcaca attgatgaaa ggctcttgac attcggatat    1320
gggcgtcgag catgccccgg ccgatggttc gcttcacaca tactgaaaat gttgatcgcg   1380
tatatcacga tcaattatga catacagccc ttgacgggac cgccgaaaaa agtcaaattc   1440
gcagatttca ccgtgccatc gccgagtatc aaaatcattg tgcgccggaa gaatctcgct   1500
tacctaggc aacgtgagcg ttga                                          1524

SEQ ID NO: 39          moltype = AA   length = 507
FEATURE                Location/Qualifiers
source                 1..507
                       mol_type = protein
                       organism = Hypoxylon pulicicidum
SEQUENCE: 39
MITASTSVFG GLILAFIFSL LYKNKKTRIP AEIDRVRTGG FLAHIRAFGC RLGTRVDDIR     60
NGYNKFNKNG KPFVIQDSTF IPQVVIPPQY LGWLKEQPEK ALSAETVRLE QLGLRYLVPS    120
SDPEMVHLLT DVVCRYLTRN FQRVQERLYE ELHMSTDEIM GLEATEWRQI CLHEAMETIL    180
RRMISCVLIG LPWCRDEECL KSWTGFLHCM AIAGTILGAV TPWFLRPLLG LLLKPPVGYM    240
RRRSLRYLTP IFTERWKKIE KHEKSSLTTR ELPDDFVTWC IQEVRNGAAE VTMLDLLSAD    300
PTIGYWEKLV EEATTAFRTD EDWIHAGTVS KLAYTDSAIR ESLRRNPFSI RNVTREVIGK    360
DGLTLPSGTR LPQGTWITTA LANIHHDARF YSNPTEYQPF RFVARDAFHT EGKEGSEKVL    420
QPSEAILTST IDERLLTFGY GRRACPGRWF ASHILKMLIA YITINYDIQP LTGPPKKVKF    480
ADFTVPSPSI KIIVRRKNLA YLRQRER                                       507

SEQ ID NO: 40          moltype = DNA   length = 1294
FEATURE                Location/Qualifiers
source                 1..1294
                       mol_type = genomic DNA
                       organism = Penicillium paxilli
SEQUENCE: 40
```

```
ttaaactctt cctttctcat tagtagggta ctccacttca agtagatcga gaatcttatg    60
aattccagga ttgggcccta aggaagtctc cagcttcttt acatagccac gagcctccgc   120
actaagtcga cttagggtct ccctagtata ttggaagctc cccgtcgact ccatgatctt   180
cacagcccgg attttgactg cttcgtcctc tgtgcgttgc tttagaatat cgagaagctc   240
ggagctctct ggagatgcac ggatgctgtg tatgatagga taggagaact tcccctccgt   300
caaatcttcc atcagccctt ttttctcagc atagagtccg ctctgcagat tcatatagtc   360
atcacgaatt tggaatataa cacccaatag ctcgacaagt ttagaaaagt cactgtaaaa   420
tactaattag cattgctgcg aagtgaccgt tatggattag aaacttacgt attcttgcgg   480
gattggatac gcatcaaatc gagggccagg ttgaaaagac ctccagtttt gtacataacc   540
atccgggtgt attcctcctc ggtcggacaa accaccatat cacgccaata taggtccatg   600
ccctggccaa gatgtagatc tagcagtgac cttgtaaata tttcgaaggc gcggggtct    660
ccaatctctt tcaatcttgc ttgttggaga tagtaggcat agttggctga gttgatagtt   720
tgtgctcacc cgtatacatc atgagccaca ggctttcctc tccggagccg tgatgcatct   780
tgaatatcat cgatactata aacaccatga tgttagaata gaacaggagc gctggggttg   840
gaaatctcac agaagggatg cagtgtgaag taagtttatt atatctttca caatagacaa   900
cttctcctct ggaagctgga gccatatgtt gaaggagtcg atcagcttgc ttcggatgtc   960
ttttcccgga atcgctagaa gatagtctag aggtccacga caatctaag aagaacaaac   1020
gattggtata atgaaacaca aggggaatcc caagagcaat acagaactg accttgttat   1080
actgaatagc aatatcgtca acgtcatctt ctagcacctg cactgttcta atcgtgcttg   1140
gtgctttgct ggaatcactc aggagtcttg ggaatccttg gaagtttgat tcccagtaat   1200
tatcagcaga taatgagtgt gaagctcccc aataattaag atgagatatt cctcgacgaa   1260
cgaagttcag agcttctgca aggatgtagg acat                               1294

SEQ ID NO: 41          moltype = DNA   length = 1116
FEATURE                Location/Qualifiers
source                 1..1116
                       mol_type = genomic DNA
                       organism = Penicillium paxilli
SEQUENCE: 41
ttaaactctt cctttctcat tagtagggta ctccacttca agtagatcga gaatcttatg    60
aattccagga ttgggcccta aggaagtctc cagcttcttt acatagccac gagcctccgc   120
actaagtcga cttagggtct ccctagtata ttggaagctc cccgtcgact ccatgatctt   180
cacagcccgg attttgactg cttcgtcctc tgtgcgttgc tttagaatat cgagaagctc   240
ggagctctct ggagatgcac ggatgctgtg tatgatagga taggagaact tcccctccgt   300
caaatcttcc atcagccctt ttttctcagc atagagtccg ctctgcagat tcatatagtc   360
atcacgaatt tggaatataa cacccaatag ctcgacaagt ttagaaaagt cagtattctt   420
gcgggattgg atacgcatca aatcgagggc caggttgaaa agacctccag ttttgtacat   480
aaccatccgg gtgtattcct cctcggtcgg acaaaccacc atatcacgcc aatataggtc   540
catgccctgg ccaagatgta gatctagcag tgaccttgta aatatttcga aggcgcgggg   600
gtctccaatc tctttcaatc ttgcttgttg gagatagtag gcatagttgg ctgagttgat   660
agtttgtgct acaccgtata catcatgagc cacaggcttt cctctccgga gccgtgatgc   720
atcttgaata tcatcgataa gaagggatgc agtgtgaagt aagtttatta tatctttcac   780
aatagacaac ttctcctctg gaagctggag ccatatgttg aaggagtcga tcagcttgct   840
tcggatgtct ttttcccgga atcgctagaa gatagtctag aggtccacga caatcttgtt   900
atactgaata gcaatatcgt caacgtcatc ttctagcacc tgcactgttc taatcgtgct   960
tggtgctttg ctggaatcac tcaggagtct tgggaatcct tggaagtttg attcccagta  1020
attatcagca gataatgagt gtgaagctcc caataattaa gatgagatat tcctcgacg   1080
aacgaagttc agagcttctg caaggatgta ggacat                            1116

SEQ ID NO: 42          moltype = DNA   length = 1077
FEATURE                Location/Qualifiers
source                 1..1077
                       mol_type = genomic DNA
                       organism = Penicillium paxilli
SEQUENCE: 42
atgggcgtag cagggagcgg agttctttac tttcttttca acaatgtccc gagtcctcgc    60
ttctggttga agaaaaccca gttgatagga accgagaacc cagaaggcat aactggctac   120
gaatgccctt atgaatatct gcggaagtca tacggcaagc atcactgggc agcgttcgtt   180
gacaagctat cgcccaacct tcaaaatgag gatccagcta aataccgcat ggtgcttgaa   240
acaatggatg tcattcacct atgcttgatg atggtcgacg atgtaagatc atttgccatt   300
atatagaggc tttattatca ttgtatctaa cttctgattc ctagatctcc gatgaagcg    360
aatatcgcaa aggaaagccg gctgcgcaca aaatttatgg tgcgcctgaa acagcgaatc   420
gggcttatta tcgagttaca caaatattgg ctcaaactgc gacagaattc ccacgtcttt   480
cgccttggtt gatgactgat cttcgggata ttctcggaag tcaagatatg tccctgtct   540
ggcgccgaga cggagtcaat gggttccctg gaactgcatc ggagagaact gctgcttaca   600
agcgcatggt tctgctaaag acaggtggac tatttcgtct actcgggcat ctcactctcg   660
agaacaattc catggatgaa gcctttagca cccttggta gaaagaaaa atattttcgg    720
cagccttctg aattttgcta atatttaatg attcctagct ggcattcgca attgcaaaat   780
gactcaaga atgtctactc gtcggaatat gccaaatgtt agggcgttgt agcagaagat   840
ttgctcaatc gtgagatgac ataccccatc gtactcgcac tggacgcctc tggtggtcat   900
tgggtagagg cagctctaaa gtcgccctct cggcgaaacg tcgaaatgc cttgaagata   960
atacagtgcg actatgttcg agatgtttgc atggcagagc tggcgagatc tggtgccccg  1020
gttaaggaat ggttgaagtt atggaaacgg gaggagaagc ttgacctgaa ggcatga     1077

SEQ ID NO: 43          moltype = DNA   length = 954
FEATURE                Location/Qualifiers
source                 1..954
                       mol_type = genomic DNA
                       organism = Penicillium paxilli
```

```
SEQUENCE: 43
atgggcgtag cagggagcgg agttctttac tttcttttca acaatgtccc gagtcctcgc    60
ttctggttga agaaaaccca gttgatagga accgagaacc cagaaggcat aactggctac   120
gaatgccctt atgaatatct gcggaagtca tacggcaagc atcactgggc agcgttcgtt   180
gacaagctat cgcccaacct tcaaaatgag gatccagctc aataccgcat ggtgcttgaa   240
acaatggatg tcattcacct atgcttgatg atggtcgacg atatctccga tggaagcgaa   300
tatcgcaaag gaaagccggc tgcgcacaaa atttatggtg cgcctgaaac agcgaatcgg   360
gcttattatc gagttacaca aatattggct caaactgcga cagaattccc acgtctttcg   420
ccttggttga tgactgatct tcgggatatt ctcgagggtc aagatatgtc ccttgtctgg   480
cgccgagacg gagtcaatgg gttccctgga actgcatcgg agagaactgc tgcttacaag   540
cgcatggttc tgctaaagac aggtggacta tttcgtctac tcgggcatct cactctcgag   600
aacaattcca tggatgaagc ctttagcacc cttggctggc attcgcaatt gcaaaatgac   660
tgcaagaatg tctactcgtc ggaatatgcc aagatgaagg gcgttgtagc agaagatttg   720
ctcaatcgtg agatgacata cccatcgta ctcgcactgg acgcctctgg tggtcattgg   780
gtagaggcag ctctaaagtc gccctctcgg cgaaacgtcg gaaatgcctt gaagataata   840
cagtgcgact atgttcgaga tgtttcatg gcagagctgg cgagatctgg tgccccggtt   900
aaggaatggt tgaagttatg gaaacgggag agaagcttg acctgaaggc atga          954

SEQ ID NO: 44           moltype = AA   length = 317
FEATURE                 Location/Qualifiers
source                  1..317
                        mol_type = protein
                        organism = Penicillium paxilli
SEQUENCE: 44
MGVAGSGVLY FLFNNVPSPR FWLKKTQLIG TENPEGITGY ECPYEYLRKS YGKHHWAAFV    60
DKLSPNLQNE DPAKYRMVLE TMDVIHLCLM MVDDISDGSE YRKGKPAAHK IYGAPETANR   120
AYYRVTQILA QTATEFPRLS PWLMTDLRDI LEGQDMSLVW RRDGVNGFPG TASERTAAYK   180
RMVLLKTGGL FRLLGHLTLE NNSMDEAFST LGWHSQLQND CKNVYSSEYA KMKGVVAEDL   240
LNREMTYPIV LALDASGGHW VEAALKSPSR RNVGNALKII QCDYVRDVCM AELARSGAPV   300
KEWLKLWKRE EKLDLKA                                                 317

SEQ ID NO: 45           moltype = DNA   length = 1559
FEATURE                 Location/Qualifiers
source                  1..1559
                        mol_type = genomic DNA
                        organism = Penicillium paxilli
SEQUENCE: 45
ttaaacttga agaaaataaa acttcagggc accctcgagg tcgaacatca ttgtaagaga    60
ggtatagaca atggttagtc caaatagata gatcataagt tgagtcaaat aactccagct   120
tcgcccctgt ttgctatact tctcccatcc accaccactt cgctttggcg tagggaggaa   180
atcacacatt gtgccatcag caatcgtttt tgacgccata tcagcaggca ggtcaccagc   240
gtatggtgcc caataccggc ttagcaggct atagattatg ccatcacgaa cctgaaaacg   300
aaccaagaat cgagagctct ggtagatagt attgacgcgc tcatatcgaa ggtcgcgata   360
tttttgcaaa aggaactcca tttgtgagga ggtgggaaag tatggtccag aggaaatccg   420
catctttcga aggagatttg ccagagcagc ggcatcctca atggccatat agccccttg    480
accaacattg ggagtcattt tgtggacact gtctcctaag agcacgcagc ggccatggtg   540
ccagactttg aatgtatttt cttccagagc agtcattgaa gatgtctctc tttttgtccca   600
gagctcgcca aaagtaatgt tttcgtaaaa cttgacatcc ctgatctctt ctgccgcaat   660
agatgtttca tgggacgtgt agcggggggct gtcaggatac acgtatttct tgcccagctt   720
ttgaatgacg aaccaatata tgcgaccgtc ttttccatgg attgtgacaa tagtgagacc   780
atcgaataaa gcgttgactt gctcgccaag ttttaatccc ggcatcgccg atgaaatgcc   840
gaaaatacag cgaaactcga ccgtaagctc ttcgtacttg ttagcatgaa tgcaaagaca   900
tgaggcctgt tgatgctatc cactcactgg aactatcttg tttgatcttt gatacccgtc   960
tggcaattcc ccttgccttc catatctctc tgcggacgat gctgtggact ccatctgcgc  1020
cgacaagaag atcccacga taaacgtgtc cagttgtggt ggtaattagc actccatcat  1080
ccaatgattc aattgatgta actctttggc ccagacgtat tttgctggga tctggatacc  1140
ctttgtagag aatttcgagc atctctgtc gatctagaaa cgctatagga aaaccgaacc  1200
tgttgcctca cgggtgccat tttagatgat aatgcaaaac tgtataagat caagataatt  1260
actgacctt gatcgatgat cttttggatat gagctgctga agttgaaccc atcaggaagc  1320
ccaattgtag ctttgcttag cggttcgata tgctcttcaa cttgatcata gagctgaagc  1380
tgatccagca cgcgagctcc attcggcaga atgccgatgg atgctccaat ctgtggtgct  1440
ggatcgctgg ccttttccag gacaaacatgt tttattcccg cacgatgtag acaatgtgcc  1500
aatgtcaatc ctccgatcga cccgcccaca atgataactt gaaactcggc cttttccat   1559

SEQ ID NO: 46           moltype = DNA   length = 1434
FEATURE                 Location/Qualifiers
source                  1..1434
                        mol_type = genomic DNA
                        organism = Penicillium paxilli
SEQUENCE: 46
ttaaacttga agaaaataaa acttcagggc accctcgagg tcgaacatca ttgtaagaga    60
ggtatagaca atggttagtc caaatagata gatcataagt tgagtcaaat aactccagct   120
tcgcccctgt ttgctatact tctcccatcc accaccactt cgctttggcg tagggaggaa   180
atcacacatt gtgccatcag caatcgtttt tgacgccata tcagcaggca ggtcaccagc   240
gtatggtgcc caataccggc ttagcaggct atagattatg ccatcacgaa cctgaaaacg   300
aaccaagaat cgagagctct ggtagatagt attgacgcgc tcatatcgaa ggtcgcgata   360
tttttgcaaa aggaactcca tttgtgagga ggtgggaaag tatggtccag aggaaatccg   420
catctttcga aggagatttg ccagagcagc ggcatcctca atggccatat agccccttg    480
accaacattg ggagtcattt tgtggacact gtctcctaag agcacgcagc ggccatggtg   540
```

-continued

```
ccagactttg aatgtatttt cttccagagc agtcattgaa gatgtctctc ttttgtccca   600
gagctcgcca aaagtaatgt tttcgtaaaa cttgacatcc ctgatctctt ctgccgcaat   660
agatgtttca tgggacgtgt agcggggggct gtcaggatac acgtatttct tgcccagctt   720
ttgaatgacg aaccaatata tgcgaccgtc ttttccatgg attgtgacaa tagtgagacc   780
atcgaataaa gcgttgactt gctcgccaag ttttaatccc ggcatcgccg atgaaatgct   840
gaaaatacag cgaaactcga ccgtaagctt ggaactatct tgtttgatct ttgatacccg   900
tctggcaatt cccccttgcct tccatatctc tctgcggacg atgctgtgga ctccatctgc   960
gccgacaaga agatccccac gataaacgtg tccagttgtg gtgtaatta gcactccatc   1020
atccaatgat tcaattgatg taactctttg gcccagacgt attttgctgg gatctggata  1080
cccctttgtag agaatttcga gcatcttctg tcgatctaga aacgctatag gaaaaccgaa  1140
cctttgatcg atgatctttg gatatgagct gctgaagttg aacccatcag gaagcccaat  1200
tgtagctttg cttagcggtt cgatatgctc ttcaacttga tcatagagct gaagctgatc  1260
cagcacgcga gctccattcg gcagaatgcc gatggatgct ccaatctgtg gtgctggatc  1320
gctggccttt tccaggacaa catgttttat tcccgcacga tgtagacaat gtgccaatgt  1380
caatcctccg atcgacccgc ccacaatgat aacttgaaac tcggccttt ccat         1434

SEQ ID NO: 47           moltype = AA  length = 477
FEATURE                 Location/Qualifiers
source                  1..477
                        mol_type = protein
                        organism = Penicillium paxilli
SEQUENCE: 47
MEKAEFQVII VGGSIGGLTL AHCLHRAGIK HVVLEKASDP APQIGASIGI LPNGARVLDQ    60
LQLYDQVEEH IEPLSKATIG LPDGFNFSSS YPKIIDQRFG FPIAFLDRQK MLEILYKGYP   120
DPSKIRLGQR VTSIESLDDG VLITTTTGHV YRGDLLVGAD GVHSIVRREI WKARGIARRV   180
SKIKQDSSKL TVEFRCIFGI SSAMPGLKLG EQVNALFDGL TIVTIHGKDG RIYWFVIQKL   240
GKKYVYPDSP RYTSHETSIA AEEIRDVKFY ENITFGELWD KRETSSMTAL EENTFKVWHH   300
GRCVLLGDSV HKMTPNVGQG ANMAIEDAAA LANLLRKMRI SSGPYFPTSS QMEFLLQKYR   360
DLRYERVNTI YQSSRFLVRF QVRDGIIYSL LSRYWAPYAG DLPADMASKT IADGTMCDFL   420
PTPKRSGGGW EKYSKQGRSW SYLTQLMIYL FGLTIVYTSL TMMFDLEGAL KFYFLQV     477

SEQ ID NO: 48           moltype = DNA  length = 1681
FEATURE                 Location/Qualifiers
source                  1..1681
                        mol_type = genomic DNA
                        organism = Hypoxylon pulicicidum
SEQUENCE: 48
atggacaagc taccacagga aatcgtggac atcatcgtct tctttgccaa ctccaacgag    60
caagggaacc aatatcacat gcacggcccc gatgctaagc atcttgcgag acaattagtc   120
actgttccca agaaattcca gcgcgccatc gagtgtgata cattcaaggt acttcatctc   180
gacttggacc gggctcgtga tgctcgtgat atcctttccc ggttctctag atggtcgcat   240
ctgagactac tagaatttac tgctatcctg cccgactatg acgaagttgc gtgcactcga   300
tatgagaacg ctgcagagaa agcagagaat cgcggggtgt ttacgaaaaa catcacagag   360
ttgttccacc ttctctctca atgcccagtt gcatgtgctt ctagacctgt ggtattgagg   420
gtagagatat attccaagac ggatcgcatc tgtgtcagcc acagtcttca aggccgtgtg   480
actcaaaagg agacgcacgc caagccagtg tctggtgaca taaggaggtg gaggtggaag   540
cggtcaaaac tacagcttga caagtcagtt cgtcttgctc caatcaaaca cctaaatata   600
cctgtcttcc agatgcaaag gcgcccgtta ttattccgac atgttgctgc tgatagcatt   660
atgcgattaa tatcagcaat gcctcccctcc ctcaagtttta ccgtcaaccg gttttcagat   720
accgaaaaga acgatcttgc tcatcgaatt gcacatcgtg agggtaagcg ttagggtctc   780
accattgatc gattaatatt cccacccatg cgttctctaa actaacatat ttccagatat   840
cgccaatgca atcgactctc ttcctaagct gatctcccca tactttcatg tggaatactt   900
gccccccctg gatcacaact tccaaccacc cgtactccac aatcacgata cgcagagcga   960
ttcggtctcc tgtgcaatac gcaggatcac ccagagatgc aaaagggtat tcgtcacagg  1020
tgtcctaggc tcaactgagc tgttctggcc aaatgtaaat tcggcccctg acccatactg  1080
gcactcgttg gaatttctgg atatttggta ccatcccatt accccgggtg gcaagtggct  1140
atttggatta gacccatttc tcctttcgg tcggcgcga atgcaggctc gcgatctcta   1200
ttcgcgtcct gagccagtag aggggcgtgc ggatgaagat caacaagcat gtcaatttcg  1260
ctatacagca atccagcaac tcatgatga gttctatgta gcggcagcac gagctgcggc  1320
aaatatgcca aagttgaaga ggttggcttt ggtggtaacc caccaaccga gttggagaat  1380
tgatggtgct cccctacacc atttcgagtt ccgggcgtcc aaagacaatc atgcctcaat  1440
tacttggacc tcctcaccag tatttactcc tagtcaggct gttatcgatg cctggatgcg  1500
tgtatcctgc attcgcggct tgtctatgcg agtaaggcta accggacgtc cattcaacga  1560
cagaggtaat acgcgctatg tggatcccac cgatgatgca cctgatagtg tgcatgaaga  1620
ggaggaggat gacgaggagt atgacgaggg ggatagcgag gaggatgaag gggaggaatg  1680
a                                                                 1681

SEQ ID NO: 49           moltype = DNA  length = 1608
FEATURE                 Location/Qualifiers
source                  1..1608
                        mol_type = genomic DNA
                        organism = Hypoxylon pulicicidum
SEQUENCE: 49
atggacaagc taccacagga aatcgtggac atcatcgtct tctttgccaa ctccaacgag    60
caagggaacc aatatcacat gcacggcccc gatgctaagc atcttgcgag acaattagtc   120
actgttccca agaaattcca gcgcgccatc gagtgtgata cattcaaggt acttcatctc   180
gacttggacc gggctcgtga tgctcgtgat atcctttccc ggttctctag atggtcgcat   240
ctgagactac tagaatttac tgctatcctg cccgactatg acgaagttgc gtgcactcga   300
tatgagaacg ctgcagagaa agcagagaat cgcggggtgt ttacgaaaaa catcacagag   360
```

```
ttgttccacc ttctctctca atgcccagtt gcatgtgctt ctagacctgt ggtattgagg    420
gtagagatat attccaagac ggatcgcatc tgtgtcagcc acagtcttca aggccgtgtg    480
actcaaaagg agacgcacgc caagccagtg tctggtgaca taaggaggtg gaggtggaag    540
cggtcaaaac tacagcttga caagtcagtt cgtcttgcct caatcaaaca cctaaatata    600
cctgtcttcc agatgcaaag gcgcccgtta ttattccgac atgttgctgc tgatagcatt    660
atgcgattaa tatcagcaat gcctccctcc ctcaagttta ccgtcaaccg gttttcagat    720
accgaaaaga acgatcttgc tcatcgaatt gcacatcgtg aggatatcgc caatgcaatc    780
gactctcttc ctaagctgat ctccccatac tttcatgtgg aatacttgcc cccctggat    840
cacaacttcc aaccacccgt actccacaat cacgatacgc agagcgattc ggtctccttg    900
gcaatacgca ggatcaccca gagatgcaaa agggtattcg tcacaggtgt cctaggctca    960
actgagctgt tctggccaaa tgtaaattcg gcccctgacc catactggca ctcgttggaa   1020
tttctggata tttggtacca tcccattacc ccgggtggca agtggctatt tggattagac   1080
ccatttctcc atttcgggtc ggcgcgaatg caggctcgcg atctctattc gcgtcctgag   1140
ccagtagagg ggcgtgcgga tgaagatcaa caagcatgtc aatttcgcta tacagcaatc   1200
cagcaactca tggatgagtt ctatgtagcg gcagcacgag ctgcggcaaa tatgccaaag   1260
ttgaagaggt tggcttttggt ggtaacccac caaccgagtt ggagaattga tggtgctccc   1320
ctacaccatt tcgagttccg ggcgtccaaa gacaatcatg cctcaattac ttggacctcc   1380
tcaccagtat ttactcctag tcaggctgtt atcgatgcct ggatgcgtgt atcctgcatt   1440
cgcggcttgt ctatgcgagt aaggctaacc ggacgtccat tcaacgacag aggtaatacg   1500
cgctatgtgg atcccaccga tgatgaccct gatagtgtgc atgaagagga ggaggatgac   1560
gaggagtatg acgaggggga tagcgaggag gatgaagggg aggaatga                1608

SEQ ID NO: 50          moltype = AA   length = 535
FEATURE                Location/Qualifiers
source                 1..535
                       mol_type = protein
                       organism = Hypoxylon pulicicidum
SEQUENCE: 50
MDKLPQEIVD IIVFFANSNE QGNQYHMHGP DAKHLARQLV TVSKKFQRAI ECDTFKVLHL     60
DLDRARDARD ILSRFSRWSH LRLLEFTAIL PDYDEVACTR YENAAEKAEN SRVFTENITE    120
LFHLLSQCPV ACASRPVVLR VEIYSKTDRI CVSHSLQGRV TQKETHAKPV SGDIRRWRWK    180
RSKLQLDKSV RLASIKHLNI PVFQMQRRPL LFRHVAADSI MRLISAMPPS LKFTVNRFSD    240
TEKNDLAHRI AHREDIANAI DSLPKLISPY FHVEYLPPLD HNFQPPVLHN HDTQSDSVSC    300
AIRRITQRCK RVFVTGVLGS TELFWPNVNS APDPYWHSLE FLDIWYHPIT PGGKWLFGLD    360
PFLHFGSARM QARDLYSRPE PVEGRADEDQ QACQFRYTAI QQLMDEFYVA AARAAANMPK    420
LKRLALVVTH QPSWRIDGAP LHHFEFRASK DNHASITWTS SPVFTPSQAV IDAWMRVSCI    480
RGLSMRVRLT GRPFNDRGNT RYVDPTDDDP DSVHEEEEDD EEYDEGDSEE DEGEE         535

SEQ ID NO: 51          moltype = DNA   length = 819
FEATURE                Location/Qualifiers
source                 1..819
                       mol_type = genomic DNA
                       organism = Penicillium paxilli
SEQUENCE: 51
tcaatttgct tttttcggcc cgcttatgcc aagtgacttt tcgttacggt cgacgtacca     60
gaaacaaatt ccataaaacc catcgattga taaaaacacc acaagactcc acagtaccaa    120
aggactattc agccaaccga atgcttccga ccaatacatc caacgtaagc cggcaaaccc    180
aactgtacat gttgatccta agaagcggga agcccatag tacagaagat gagtacttgt    240
atttctgtca ctttgggaa gaaattccga ttcatcgggc atgaaatgag atcagacata    300
ccatagagta taggatgcgc cacgcgtact gcctcgacac aacagttgac tcaatccacc    360
aacgcttaga agaagttgac aaatgacggc cccccatgaa tatgccagcg caggcccgat    420
ttcaagggcc aatgcaacat gcccagagag aaagcccatg gtcgcgacga aaatatcaa    480
ggaaatattg cgctcaacaa gcggcgcatg gccccactct cgggatgaaa acgttattgc    540
tgcgtacatg acaccaaagt tgatgaggag gcccatccag aatacacccc tctccaccgg    600
gcttttcgag ggaaagacca gacagtagac cagttccac gcgatgttgc aacagagggg    660
cataatcgac attccgtaag tttcatgttt gaacgagatg tagaccattc cgatcgtagtt    720
tatgatcat cctactccca tgccaacaac aaaaagatca gccaatggct taatcgcctg    780
gtactccgga ggagcttggg aaacatcaaa accgtccat                           819

SEQ ID NO: 52          moltype = DNA   length = 732
FEATURE                Location/Qualifiers
source                 1..732
                       mol_type = genomic DNA
                       organism = Penicillium paxilli
SEQUENCE: 52
tcaatttgct tttttcggcc cgcttatgcc aagtgacttt tcgttacggt cgacgtacca     60
gaaacaaatt ccataaaacc catcgattga taaaaacacc acaagactcc acagtaccaa    120
aggactattc agccaaccga atgcttccga ccaatacatc caacgtaagc cggcaaaccc    180
aactgtacat gttgatccta agaagcggga agcccataga gtataggatg cgccacgcgt    240
actgcctcga cacaacagtt gactcaatcc accaacgctt agaagaagtt gacaaatgac    300
ggccccccat gaatatgcca gcgcaggccc gatttcaagg ccaatgcaa catgcccaga    360
gagaaagccc atggtcgcga cgaaaaatat caaggaaata ttgcgctcaa caagcggcgc    420
atggccccac tctcgggatg aaaacgttat tgctgcgtac atgacaccaa agttgatgag    480
gaggcccatc cagaatacac ccctctccac gggcttttc gagggaaaga ccagacagta    540
gaccagttcc cacgcgatgt tgcaacagag gggcataatc gacattccgt aagtttcatg    600
tttgaacgag atgtagacca ttccgatgta gtttatgatc catcctactc ccatgccaac    660
aacaaaaaga tcagccaatg gcttaatcgc ctggtactcc ggaggagctt gggaaacatc    720
aaaaccgtcc at                                                        732
```

```
SEQ ID NO: 53          moltype = AA   length = 243
FEATURE                Location/Qualifiers
source                 1..243
                       mol_type = protein
                       organism = Penicillium paxilli
SEQUENCE: 53
MDGFDVSQAP PEYQAIKPLA DLFVVGMGVG WIINYIGMVY ISFKHETYGM SIMPLCCNIA     60
WELVYCLVFP SKSPVERGVF WMGLLINFGV MYAAITFSSR EWGHAPLVER NISLIFFVAT    120
MGFLSGHVAL ALEIGPALAY SWGAVICQLL LSVGGLSQLL CRGSTRGASY TLWASRFLGS    180
TCTVGFAGLR WMYWSEAFGW LNSPLVLWSL VVFLSIDGFY GICFWYVDRN EKSLGISGPK    240
KAN                                                                  243

SEQ ID NO: 54          moltype = DNA   length = 5083
FEATURE                Location/Qualifiers
source                 1..5083
                       mol_type = genomic DNA
                       organism = Hypoxylon pulicicidum
SEQUENCE: 54
atgggatatg gaccaggtac aagagcctct gcaggcgttt ctgattccgc attgaggggc     60
atgcaagaac tgacagcatt tttttcacca gagcttcata agacattaac tcgcgtacta    120
tctagctcta gatctgatgg cacgtcatta tttcacggtc gttcattgat ctctgaatcg    180
actccgtaa cctccgataa tgagactcac ggcgttcttg gcctatcaac tctttacgaa     240
ccctcatttc ctactagcgc tacggccgat atcgtcttcg tccatggatt aggcggaggt    300
agtcgaaaaa catggtccta ttccccgac cggtaccact actggcctca agcatggctt     360
gcgaacgact cggacttcgc agatatgcgc atccactcct tcggctataa gtccgactgg    420
gctgagcgac agcaaagcat cctcaatatt cgcgacttcg ccgaatcgtt agtcggagag    480
ctgaagaaca atcccggcat acgacgtagt aatacacgca tcatattcgt ttgccatagt    540
atgggcggat gcgtcgccaa aaaggcctac attatatcac gccaggatcc gacctgcaag    600
gacttagctg acagagtcca ctcgatattc tttctaggca ctccacacag gggcagtgat    660
cttcagtga tcctgaagag gttgtctgtc atcgcttggg gctccaagcc gttcgtctcc     720
gacctcctgc ccgaatcgtt tacattgaga gatatcaacg acacatttcg tcactatgcg    780
tcggatctgc gcctctggtc cttttacgag acgattcccg ccaagccagt gattttgaac    840
aaaatcgttg ttgagaggca ctcggcaacg cttggttacc caaacgaaga gattgttgct    900
atgaacgctg accacgcca gttgtgcaaa ttcaaaagtc cggctgaccc taattacaag     960
atattacgaa atgccctcca cacggctgcc gatatgctaa ggtcattacc acctttggcc   1020
ttagcccct tagaacctcg tatcaacttg gcttccacac aacagcattc gaaccaagag    1080
aacgcaagcc aacgcttgag gtcctttcta ggcgtcgttg atacgccaga ggatgaactc    1140
catattcttc aactgtttca ggagccggga tcttgccggt ggttctcgga atcgaaagac    1200
ttcgtgtctt gggaatcgga agggtccccg agcatactgt ggctcacggg gagaccagcg    1260
tccggtaaat ccgtccttc tagccacgtc atagagcaag tgaagtctct aggtgccttt    1320
tgcagttact ttttcttcaa gcaaagggag gctagcaagt ctacgctgag cgattgtttc    1380
cgctccattg ccttttcagat ggccatacaa gatagtgaag tgatgaataa gctacttcaa   1440
ctcgaaggcg aatggatgac ctgggatatg agcgacgagc tgagcgtctg aggaaggctt    1500
ttcgtcaatg ggatcttcaa gctgccatcc atctcacaga acttctggat aatcgacggt    1560
gtcgatgaat gttctaattt caactcccct tttactaaga gaatcctcgc tacgcttcct    1620
agaggtattc gccttttcgc cagcagccgc catctagaag aaatcggcg cggttttggca   1680
cctcttgagt cgcgtgtgaa cctgcagtcc gtgtctgaaa ccgacactct tggtgatatg    1740
cggattttcg tgacttcgaa gctcagaggg ctagatcgcc ttgaaaatga tgacagtatc    1800
aatacaatgt gcgagaaaat cctggggaag gcatccggtt cttctttatg ggtccgactc    1860
gtacttcaag agttcgaaaa tgcttggact agcgaagcca tggatgctgt cttggatgaa    1920
atacctgtag atcttcaaga catgtatcgc cggatgcttc tgttaatgga aaggatacg    1980
cgtacaatca agctcgccaa atccatcctg acgtgggccg ttctggcatg ccgaccgctc    2040
accgttgacg agctacgtct tgctgtgaag ctcgacgtta tgagacgct gcagagtgta    2100
agcaaggcga ttcctagttt atgccaccaa ctagtctttg tcgacagcgc taataggtgt    2160
cacatcttac atgcaaccgc ccgggaattt ctttctgacg aaactcttca gtcagagttt    2220
gctcttcatg gtgttgagaa gcacgcctct cttggctctc tactgcttcg gtatctcacc    2280
aacaccgcct taagttccg tgcgccaccg cggcggcagg gctcaggatt tcgcggttt    2340
gcgaagcccg ttcatagtgt ttctcctgat ctatccctat tggactacgc agcttgcttc    2400
ttctctgagc acatatacog aggcgcctcg agagatgata cctttgatgg cgaactgtgt    2460
gccttcctaa agggcagaac tatcctctca tggattgaac acatcgctag aaatggagat    2520
cttgaggta ttaccaggac ggcgacagac ttacgtggat atctcggccg gaaactggaa    2580
catcttcctc ccacagatcc ctcggcctac cttgttgact gctgggtggc tgatctaatc    2640
cggggttgctg ccaagtttcg atttcagttg ctgacctgtc catcgtctat tcattacatt    2700
atcccatcat tctgtccatc agacactatt atctcgagga ccttgccaa tggtactcga    2760
ccttcgacaa taacagtcaa gggtatccct caagccacgt gggacgactg cttaacccgt    2820
atcgattttg agcgaggtcg agctaccgcc ttgagctatg gtaccaatt cttcgctgtt    2880
ggtttgtcga ccgggcagat ttcgctcttc gatccgcact ctgtcagcc cgtggcgaac    2940
cttgtccatc ctgaaagggt caagatgctg gagtttagct ccgacggaga atatcttgcc    3000
tcctctggca ctagaacttt gcttgtttgg cagccgaact tgggatgca gttgtactcga   3060
ttcccattgc agtcggagct tatcgctttt gttttcttaa gcggtgacga atttcttgt    3120
gctttcgcat ctggtgagct aactaaatgg taagatcacc tattcagacc tcacgaatca    3180
caacgccgcc tttcaaagct tcgtctttag atacagtact gattcttgac aacttaggcg   3240
tcttgacacg ggcgaacatg aaacaatctc tggagaagc atgtgtgata cggatattac    3300
cggtactcg gatattcctg agcagccgcc aagctgcgcg gcgttctcta caggggtga    3360
gactgtgctg cttgctctgg gttaccgaaa atacccata ttcatctggg acgcattgga    3420
gctacaattg ctgggacaat gcggagctga cgaaaacaat gggatagatg acatgacatt    3480
taatccaaac cctgagatat ctgcgctagt ggtctcctac aatgacggca ggttatgcct    3540
cttcgattac acgaccatga tgccgacgtt tactcgacaa agcgtattcg cgaacagtat    3600
tgcctgttcc ccggacggtc gaagtctcgt taccggcagt gtcaggggta tcattgaggt    3660
```

```
attcaaattc gaccaggacc ataccgggaa cacggtgcta gtccctatat acaatatcca   3720
agctttagat gactcgatcc gcagcgtagc ctttagcgct gatggcctgc gcttcgttga   3780
ccttcacgac caacaatgcc gcatttgggc accgtgtctc ctgatgcgga aggataacga   3840
actgagagcg taagtggca ttgcgccgct tcctgccaaa atagtcacca tggccgacga    3900
ctccaatatc acagaaatca cgagtgcctt agctgtgtcc tctaacgacg gccgcgtcat   3960
tgcaggtaag agtaacggcg aggtctccgc gttttcggct gtcgatggga agaattagg    4020
agtgctctat tcgcatggac gttgcgtatc cgttgtcaac gtcacccag gagaagctcg    4080
taatttagtc atctcagcgg atgatgctgg cagggtgcta gtggtggaac tgacaacgtg   4140
cctgccagcc tcctcggccg cacagaagct gccagcggct catgttattc tagagcgcag   4200
attcggtgct gctgttgttg gtctactcgt taaccccctcg gtggaccgcc ttctaattag   4260
tgggcgacat gtgatgaac tctgtgatct gccgtcgggc cgggttttgg gttcgatatc    4320
tcatgtcgtc ggtaccgcta catcgacaag agccgtagcc ttccagcatc agccaacga    4380
ggcctggatc gtcttgatgc tcactaatac cgctcgggtt ttccgctggt ccgatttcca   4440
ggagttgact accgtgaacg gcatcctcct tcggaaacct tcgacagccg tagaggctcc   4500
tctcccacg cattcccggg cttttgaaaac accaaccacg ctcagctcat cgtatcatttt  4560
taggcaagat tttgtcctcg agttgctcag aatatcgccc tccgtagctc cacgactcta   4620
cgtttggccg gtgtcagcat ttgatccggc aacagcacag ccggatcacc gagcgcaggt   4680
tcctagggaa gtgaatcttg acgccatcaa tgccggaatc ttggctgtgc ttgaatcgt    4740
aggtcagtct acggttctcc ttatggacgc caatctttgg gtatacagca tggagctccg   4800
cccaacgcaa gccacaccac aggcccaccc tggctttccc cctgaaacga cgatagttca   4860
ggacggacct gagccaatca cgcaacaaat tctgccggtg tttacaagga cacttttt    4920
cgccctgagc gagtggcgca cagccggcga agagttgagg tggccggtag cgcagcattc   4980
tggtggcccg agtttcattt ttgccagtag gcagtacatc gtcgtcgttc aaggcggttt   5040
ggagttttcc gaggacatgg ctgtcggcca gcagagtgcg tag                     5083
```

```
SEQ ID NO: 55           moltype = DNA    length = 4995
FEATURE                 Location/Qualifiers
source                  1..4995
                        mol_type = genomic DNA
                        organism = Hypoxylon pulicicidum
SEQUENCE: 55
atgggatatg gaccaggtac aagagcctct gcaggcgttt ctgattccgc attgagggc     60
atgcaagaac tgcagcatt ttttcacca gagcttcata agacattaac tcgcgtacta     120
tctagctcta gatctgatgg cacgtcatta tttcacggtc gttcattgat ctctgaatcg    180
actcccgtaa cctccgataa tgagactcac ggcgttcttg gcctatcaac tctttacgaa    240
ccctcatttc ctactagcgc tacggccgat atcgtcttcg tccatggatt aggcggaggt    300
agtcgaaaaa catggtccta ttccccgac cggtaccact actggcctca agcatggctt     360
gcgaacgact cggacttcgc agatatgcgc atccactcct tcggctataa gtccgactgg    420
gctgagcgac agcaaagcat cctcaatatt cgcgacttcg tcgaatcgtt agtcggagag    480
ctgaagaaca atcccggcat acgacgtagt aatacacgca tcatattcgt ttgccatagt    540
atgggcggat gcgtcgccaa aaaggcctac attatatcac gccaggatcc gacctgcaag    600
gacttagctg acagagtcca ctcgatattc tttctaggca ctccacacag gggcagtgat    660
cttgcagtga tcctgaagag gttgtctgtc atcgcttggg gctccaagcc gttcgtctgc    720
gacctcctgc ccgaatcgtc tacattgaga gatatcaacg acacatttcg tcactatgcg    780
tcggatctgc gcctctggtc ctttttacgag acgattcccg ccaagcccag gatttttgaac   840
aaaatcgtgg ttgagaggca ctcggcaacg cttggttacc caaacgaaga gattgttgct    900
atgaacgctg accaaccgca gttgtgcaaa ttcaaaagtc cggctgaccc taattacaag    960
atattacgaa atgccctcca cacggctgcc gatatgctaa ggtcattacc accttttggcc  1020
ttagcccccct tagaacctcg tatcaacttg gcttccacac aacagcattc gaaccaagag  1080
aacgcaagcc aacgcttgag gtccttttcta ggcgtcgttg atacgccaga ggatgaactc   1140
catattcttc aactgtttca ggagccggga tcttgccggt ggttctcgga atcgaaagac   1200
ttcgtgtctt gggaatcgga aggtcccgg agcatactgt ggctcacggg gagaccagcg    1260
tccggtaaat ccgtccttc tagccacgtc atagagcaag tgaagtctct aggtgccttt    1320
tgcagttact ttttcttcaa gcaaaggag gctagcaagt ctacgctgag cgattgtttc    1380
cgctccattg ccttttcagat ggccatacaa gatagtgaag tgataataa gctactcaa    1440
ctcgaaggcg aatggatgac ctgggatatg agcgacgagc tgagcgtctg gagaaggctt   1500
ttcgtcaatg gatcttcaa gctgccatcc atctcacagc acttctggat aatcgacggt    1560
gtcgatgaat gttctaattt caactccctt tttactaaga gaatcctcgc tacgcttcct    1620
agaggtattc gccttttcgc cagcagccgc catctagaaa aaatccggcg cggtttggca   1680
cctcttgagt cgcgtgtgaa cctgcagtcc gtgtctgaaa ccgacactct tggtgatatg   1740
cggatttttcg tgacttcgaa gctcagaggg ctagatcgcc ttgaaaatga tgacagtatc  1800
aatacaatgt gcgagaaaat ccttgggaag gcatccggtt ctttcttatg ggtccgactc   1860
gtacttcaag agttcgaaaa tgcttggact agcgaagcca tggatgctgt cttgatgaa    1920
atacctgtag atcttcaaga catgtatcgc cggatgctgt tgttaatgga aaggatacg    1980
cgtacaatca agctcgccaa atccatcctg acgtgggccg ttctggcatg ccgaccgctc   2040
accgttgacg agctacgtct tgctgtgaag ctcgacgtta atgagacgct gcagagtgta   2100
agcaaggcga ttcctagttt atgccaccaa ctagtctttg tcgacagcgc taataggggtg  2160
cacatcttac atgcaaccgc ccgggaattt ctttctcgacg aaactcttca gtcagagttt   2220
gctcttcatg ctgttgagaa cacgcctctc cttggcttcg tactgcttcg gtatctcacc   2280
aacaccgcct ttaagttccg tgcgccaccg cggcggcagg ctcaggatt cgcggtttt     2340
gcgaagcccg ttcatagtgt ttctcctgat ctatccctat tggactacgc agcttgcttc   2400
ttctctgagc acatataccg aggcgcctcg agagatgata ccttgatggc cgaactgtgt   2460
gccttcctaa agggcagaac tatcctctca tggattgaac acatgctag aaatggagat   2520
cttggaggta ttaccaggac ggcgacagac ttacgtgat atctcggaccg gaaactggaa  2580
catcttcctc ccacagatcc ctcggcctac cttgttgact gctgggtggc tgatctaatc   2640
cgggttgctg ccaagtttcg atttcagttg ctgacctgtc catcgtctat tcattacatt    2700
atcccatcat tctgtccatc agacactatt atctcgagga cctttgccaa tggtactcga    2760
ccttcgacaa taacagtcaa gggtatccct caagccacgt gggacgactg cttaaccgt     2820
atcgattttg agcgaggtcg agctaccgcc ttgagctatg gtacccaatt cttcgctgtt   2880
```

```
ggtttgtcga ccgggcagat ttcgctcttc gatccgcact ctgtccagcc cgtggcgaac 2940
cttgtccatc ctgaaagggg caagatgctg gagtttagct ccgacggaga atatcttgcc 3000
tcctctggca ctagaacttt gcttgtttgg cagccgaaat gtgggatgca gaagttgtca 3060
ttcccattgc agtcggagct tatcgctttt gttttcttaa gcggtgacga atttctttgt 3120
gctttcgcat ctggtgagct aactaaatgg cgtcttgaca cgggcgaaca tgaaacaatc 3180
tcctggagaa gcatgtgtga tacggatatt accggtactc tggcttgtcc tgagcagccg 3240
ccaagctgcg cggcgttctc tacaggggg gagactgtgc tgcttgctgt gggttaccga 3300
aaatacccca tattcatctg ggacgcattg gagctacaat tgctgggaca atgcggagct 3360
gacgaaaaca atgggataga tgacatgaca tttaatccaa accctgagat atctgcgcta 3420
gtggtctcct acaatgacgg caggttatgc ctcttcgatt acacgaccat gatgccgacg 3480
tttactcgac aaagcgtatt cgcgaacagt attgcctgtt ccccgacgg tcgaagtctc 3540
gttaccggca gtgtcagggg tatcattgag gtattcaaat tcgaccagga ccatacggtg 3600
aacacggtgc tagtccctat atacaatatc caagctttag atgactcgat ccgcagcgta 3660
gcctttagcg ctgatggcct gcgcttcgtt gaccttcacg accaacaatg ccgcatttgg 3720
gcacccgtgt ctctgatgcg gaaggataac gaactggaga gcgtaagtgg cattgcgccg 3780
cttcctgcca aaatagtcac catggccgac gactccaata tcacagaaat cacgcagtgcc 3840
ttagctgtgt cctctaacgg cgtccgcgtc attgcaggta agagtaacgg cgaggtctcc 3900
gcgttttcgg ctgtcgatgg gaaagaatta ggagtgctct attcgcatgg acgttgcgta 3960
tccgttgtca acgtcaccct aggagaagct cgtaatttag tcatctcagc ggatgatgct 4020
ggcagggtgc tagtggtgga actgacaacg tgcctgccag cctcctcggc cgcacagaag 4080
ctgccagcgg ctcatgttat tctagagcgc cgattcggtg ctgctgttgt tggtctactc 4140
gttaacccct cggtggaccg cctttctaatt agtgggcgac atgtggatga actctgtgat 4200
ctgccgtcgg gccgggtttt gggttcgata tctcatgtcg tcggtaccgc tacatcgaca 4260
agagccgtag ccttccagca tccagccaac gaggcctgga tcgtcttgat gctcactaat 4320
accgctcggg ttttccgctg gtccgatttc caggagttga ctaccgtgaa cggcatcctc 4380
cttcggaaac cttcgacagc cgtagaggct cctctcccca cgcattcccg ggctttgaaa 4440
acaccaacca cgctcagctc atcgtatcat tttaggcaag attttgtcct cgagttgctc 4500
agaatatcgc cctccgtagc tccacgactc tacgtttggc cggtgtcagc atttgatccg 4560
gcaacagcac agccggatca ccgagcgcag gttcctaggg aagtgaatct tgacgccatc 4620
aatgccggaa tcttggctgt gcttggaatc gtaggtcagt ctacggttct ccttatggac 4680
gccaatcttt gggtatacag catggagctc cgcccaacgc aagccacacc acaggccac 4740
cctggctttc ccctgaaac gacgatagtt caggacggac ctgagccaat cacgcaacaa 4800
attctgccgg tgtttacaag gagacacttt ttcgccctga gcagtggcg cacagccggc 4860
gaagagttga ggtgcgcggt agcgcagcat tctggtggcc cgagtttcat ttttgccagt 4920
aggcagtaca tcgtcgtcgt tcaaggcggt ttggagtttt ccgaggacat ggctgtcggc 4980
cagcagagtg cgtag                                                  4995

SEQ ID NO: 56         moltype = AA   length = 1664
FEATURE               Location/Qualifiers
source                1..1664
                      mol_type = protein
                      organism = Hypoxylon pulicicidum
SEQUENCE: 56
MGYGPGTRAS AGVSDSALRG MQELTAFFSP ELHKTLTRVL SSSRSDGTSL FHGRSLISES  60
TPVTSDNETH GVLGLSTLYE PSFPTSATAD IVFVHGLGGG SRKTWSYSPD RYHYWPQAWL 120
ANDSDFADMR IHSFGYKSDW AERQQSILNI RDFAESLVGE LKNNPGIRRS NTRIIFVCHS 180
MGGCVAKKAY IISRQDPTCK DLADRVHSIF FLGTPHRGSD LAVILKRLSV IAWGSKPFVS 240
DLLPESSTLR DINDTFRHYA SDLRLWSFYE TIPAKPRILN KIVVERHSAT LGYPNEEIVA 300
MNADHRQLCK FKSPADPNYK ILRNALHTAA DMLRSLPPLA LAPLEPRINL ASTQQHSNQE 360
NASQRLRSFL GVVDTPEDEL HILQLFQEPG SCRWFSESKD FVSWESEGSP SILWLTGRPA 420
SGKSVLSSHV IEQVKSLGAF CSYFFFKQRE ASKSTLSDCF RSIAFQMAIQ DSEVMNKLLQ 480
LEGEWMTWDM SDELSVWRRL FVNGIFKLPS ISQHFWIIDG VDECSNFNSL FTKRILATLP 540
RGIRLFASSR HLEEIRRGLA PLESRVNLQS VSETDTLGDM RIFVTSKLRG LDRLENDDSI 600
NTMCEKILGK ASGSFLWVRL VLQEFENAWT SEAMDAVLDE IPVDLQDMYR RMLLLMEKDT 660
RTIKLAKSIL TWAVLACRPL TVDELRLAVK LDVNETLQSV SKAIPSLCHQ LVFVDSANRV 720
HILHATAREF LLDETLQSEF ALHGVEKHAS LGSLLLRYLT NTAFKFRAPP RRQGSGFRGF 780
AKPVHSVSPD LSLLDYAACF FSEHIYRGAS RDDTLMAELC AFLKGRTILS WIEHIARNGD 840
LGGITRTATD LRGYLGRKLE HLPPTDPSAY LVDCWVADLI RVAAKFRFQL LTCPSSIHYI 900
IPSFCPSDTI ISRTFANGTR PSTITVKGIP QATWDDCLTR IDFERGRATA LSYGTQFFAV 960
GLSTGQISLF DPHSVQPVAN LVHPERVKML EFSSDGEYLA SSGTRTLLVW QPKCGMQKLS 1020
FPLQSELIAF VFLSGDEFLC AFASGELTKW RLDTGEHETI SWRSMCDTDI TGTLDIPEQP 1080
PSCAAFSTGG ETVLLAVGYR KYPIFIWDAL ELQLLGQCGA DENNGIDDMT FNPNPEISAL 1140
VVSYNDGRLC LFDYTTMMPT FTRQSVFANS IACSPDGRSL VTGSVRGIIE VFKFDQDHTG 1200
NTVLVPIYNI QALDDSIRSV AFSADGLRFV DLHDQQCRIW APVSLMRKDN ELESVSGIAP 1260
LPAKIVTMAD DSNITEITSA LAVSSNGGRV IAGKSNGEVS AFSAVDGKEL GVLYSHGRCV 1320
SVVNVTLGEA RNLVISADDA GRVLVVELTT CLPASSAAQK LPAAHVILER RFGAAVVGLL 1380
VNPSVDRLLI SGRHVDELCD LPSGRVLGSI SHVVGTATST RAVAFQHPAN EAWIVLMLTN 1440
TARVFRWSDF QELTTVNGIL LRKPSTAVEA PLPTHSRALK TPTTLSSSYH FRQDFVLELL 1500
RISPSVAPRL YVWPVSAFDP ATAQPDHRAQ VPREVNLDAI NAGILAVLGI VGQSTVLLMD 1560
ANLWVYSMEL RPTQATPQAH PGFPPETTIV QDGPEPITQQ ILPVFTRRHF FALSEWRTAG 1620
EELRCAVAQH SGGPSFIFAS RQYIVVVQGG LEFSEDMAVG QQSA                 1664
```